US011623205B2

(12) United States Patent
Wyman et al.

(10) Patent No.: US 11,623,205 B2
(45) Date of Patent: Apr. 11, 2023

(54) METHOD AND SYSTEM FOR HYBRID CATALYTIC BIOREFINING OF BIOMASS TO METHYLATED FURANS AND DEPOLYMERIZED TECHNICAL LIGNIN

(71) Applicant: The Regents of the University California, Oakland, CA (US)

(72) Inventors: Charles E. Wyman, Riverside, CA (US); Charles Cai, Riverside, CA (US); Phillip Christopher, Santa Barbara, CA (US); Bhogeswararao Seemala, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/296,590

(22) Filed: Mar. 8, 2019

(65) Prior Publication Data
US 2019/0374929 A1 Dec. 12, 2019

Related U.S. Application Data

(60) Provisional application No. 62/640,406, filed on Mar. 8, 2018, provisional application No. 62/640,305, filed on Mar. 8, 2018.

(51) Int. Cl.
*B01J 23/755* (2006.01)
*B01J 23/72* (2006.01)
(Continued)

(52) U.S. Cl.
CPC ............ *B01J 23/755* (2013.01); *B01J 23/72* (2013.01); *B01J 37/04* (2013.01); *B01J 37/08* (2013.01);
(Continued)

(58) Field of Classification Search
CPC ......... B01J 23/755; B01J 23/72; B01J 21/063
See application file for complete search history.

(56) References Cited

U.S. PATENT DOCUMENTS 4,725,573 A * 2/1988 Mesters ................ C07C 1/0445
502/331
5,354,935 A * 10/1994 Van Buren ............... B01J 37/02
585/440
(Continued)

OTHER PUBLICATIONS

Aldosari et al., "Pd—Ru/Tio2 Catalyst—An Active and Selective Catalyst for Furfural Hydrogenation", Catalysis Science & Technology, vol. 6, No. 1, 2016, pp. 234-242.
(Continued)

*Primary Examiner* — Ellen M McAvoy
*Assistant Examiner* — Ming Cheung Po
(74) *Attorney, Agent, or Firm* — Viksnins Harris Padys Malen LLP

(57) ABSTRACT

A method is disclosed for converting biomass into a fuel additive, the method comprising: liquefying the biomass to form a liquor; neutralizing the liquor; precipitating lignin out of the liquor; extracting furfural (FF) and 5-hydroxymethylfurfural (HMF) from the liquor; and hydrodeoxygenating (HDO) the extracted furfurals over a Cu—Ni/TiO$_2$ catalyst. The catalyst for hydrodeoxygenating (HDO) furfural (FF) and 5-hydroxymethylfurfural (HMF) to methylated furans comprises copper-nickel (Cu—Ni) particles supported on titanium dioxide (TiO$_2$), and wherein the copper-nickel particles form core-shell structures in which copper (Cu) is enriched at a surface of the catalyst.

14 Claims, 53 Drawing Sheets

(51) Int. Cl.
| | |
|---|---|
| C07D 307/50 | (2006.01) |
| B01J 37/04 | (2006.01) |
| C07D 307/36 | (2006.01) |
| C10L 1/185 | (2006.01) |
| B01J 37/08 | (2006.01) |
| B01J 21/06 | (2006.01) |
| B01J 35/12 | (2006.01) |

(52) U.S. Cl.
CPC ......... *C07D 307/36* (2013.01); *C07D 307/50* (2013.01); *C10L 1/1855* (2013.01); *B01J 21/063* (2013.01); *B01J 35/12* (2013.01)

(56) References Cited

U.S. PATENT DOCUMENTS

| | | | | |
|---|---|---|---|---|
| 8,435,915 | B2 * | 5/2013 | Prochazka, Jr. | ....... B01J 35/023 977/773 |
| 2010/0137650 | A1 * | 6/2010 | Wolk | ................... B01J 23/8892 585/270 |
| 2010/0187650 | A1 * | 7/2010 | Poveda | ............... H01L 27/0814 257/506 |

OTHER PUBLICATIONS

Antolini et al., "The Stability of Pt-M (M = First Row Transition Metal) Alloy Catalysts and its Effect on the Activity in Low Temperature Fuel Cells a Literature Review and Tests on a Pt—Co Catalyst", Journal of Power Sources, vol. 160, Apr. 18, 2006, pp. 957-968.
Assary et al., "Mechanistic Insights into the Decomposition of Fructose to Hydroxy Methyl Furfural in Neutral and Acidic Environments Using High-Level Quantum Chemical Methods", The Journal of Physical Chemistry B, vol. 115, No. 15, Mar. 28, 2011, pp. 4341-4349.
Baker et al., "On The Characterization and Spinning of an Organic-Purified Lignin Toward The Manufacture of Low-Cost Carbon Fiber", Journal of Applied Polymer Science, vol. 124, No. 1, 2012, pp. 227-234.
Biesinger et al., "X-Ray Photoelectron Spectroscopic Chemical State Quantification of Mixed Nickelmetal, Oxide and Hydroxide Systems", Surface and Interface Analysis, vol. 41, 2009, pp. 324-332.
Biswas et al., "Vapor Phase Hydrogenation of 2-Methylfuran over Noble and Basemetal Catalysts", Applied Catalysis A: General, vol. 475, 2014, pp. 379-385.
Bohre et al., "Upgrading Furfurals to Drop-in Biofuels: An Overview", ACS Sustainable Chemistry & Engineering, vol. 3, No. 7, May 26, 2015, pp. 1263-1277.
Bond et al., "Production of renewable jet fuel range alkanes and commodity chemicals from integrated catalytic processing of biomass", Energy & Environmental Science, vol. 7, No. 4, 2014, pp. 1500-1523.
Bonet et al., "Synthesis and Characterization of Bimetallic Ni—Cu Particles", Journal of Solid State Chemistry, vol. 172, 2003, pp. 111-115.
Boucher et al., "Single Atom Alloy Surface Analogs in Pd0.18Cu15 Nanoparticles for Selective Hydrogenation Reactions", Physical Chemistry Chemical Physics, vol. 15, No. 29, Aug. 7, 2013, pp. 12187-12196.
Bozell JosephJ. , "Connecting Biomass and Petroleum Processing with a Chemical Bridge", Science, vol. 329, Jul. 30, 2010, pp. 522-523.
Bozell et al., "Technology Development for the Production of Biobased Products from Biorefinery Carbohydrates—The US Department of Energy's "Top 10" Revisited", Green Chemistry, vol. 12, No. 4, Apr. 2010, pp. 539-554.
Brongersma et al., "Surface Segregation in Cu—Ni And Cu—Pt Alloys; A Comparison of Low-Energy Ion-Scattering Results with Theory", Surface Science, vol. 71, Iss. 3, Feb. 2, 1978, pp. 657-678.

Cai Charlesm., "Chemical and Environmental Engineering", Dissertation, University of California Riverside, 2014, 237 pages.
Cai et al., "Coupling Metal Halides with a Co-solvent to Produce Furfural and 5-HMF at High Yields Directly from Lignocellulosic Biomass as an Integrated Biofuels Strategy", Green Chemistry, vol. 16, No. 8, 2014, pp. 3819-3829.
Cai et al., "Integrated Furfural Production as a Renewable Fuel and Chemical Platform From Lignocellulosic Biomass", Journal of Chemical Technology & Biotechnology, vol. 89, 2014, pp. 2-10.
Cai et al., "THF Co-Solvent Enhances Hydrocarbon Fuel Precursor Yields From Lignocellulosic Biomass", Green Chemistry, vol. 15, No. 11, Oct. 2013, pp. 3140-3145.
Calderone et al., "Bimetallic Catalysts for the Fischer-Tropsch Reaction†", Green Chemistry, vol. 13, No. 8, Apr. 26, 2011, pp. 1950-1959.
Carrero et al., "Hydrogen Production by Ethanol Steam Reforming over Cu—Ni/SBA-15 Supported Catalysts Prepared by Direct Synthesis and Impregnation", Applied Catalysis A: General, vol. 327, 2007, pp. 82-94.
Chen et al., "The Ethanol Steam Reforming over Cu—Ni/Sio2 Catalysts: Effect of Cu/Ni Ratio", Applied Catalysis B: Environmental, vol. 106, 2011, pp. 639-649.
Clarke J.K.A. , "Selectivity in Catalysis by Alloys", Chemical Reviews, vol. 75, No. 3, Jun. 1, 1975, pp. 291-305.
Cleve et al., "Nanoscale Engineering of Efficient Oxygen Reduction Electrocatalysts by Tailoring the Local Chemical Environment of Pt Surface Sites", ACS Catalysis, vol. 7, Nov. 16, 2016, pp. 17-24.
Climent et al., "Converting Carbohydrates to Bulk Chemicals and Fine Chemicals over Heterogeneous Catalysts", Green Chemistry, vol. 13, No. 3, 2011, pp. 520-540.
Danon et al., "Mechanistic and Kinetic aspects of Pentose Dehydration Towards Furfural in Aqueous Media Employing Homogeneous Catalysis", Green Chemistry, vol. 16, 2014, pp. 39-54.
De et al., "Ni-Based Bimetallic Heterogeneous Catalysts for Energy and Environmental Applications", Energy & Environmental Science, vol. 9, 2016, pp. 3314-3347.
Ding et al., "Synthesis and Catalytic Performance of Ni/SiO2 for Hydrogenation of 2-Methylfuran to 2-Methyltetrahydrofuran", Journal of Nanomaterials, vol. 2015, Article No. 791529, Jan. 27, 2015, 6 pages.
Dong et al., "Highly Dispersed Cu Nanoparticles as an Efficient Catalyst for the Synthesis of the Biofuel 2-Methylfuran†", Catalysis Science & Technology, vol. 6, 2016, pp. 767-779.
Dong et al., "One-step Conversion of Furfural into 2-Methyltetrahydrofuran under Mild Conditions", ChemSusChem, vol. 8, No. 9, 2015, pp. 1534-1537.
Dunlop et al., "Thermal Stability of Furfural", Industrial & Engineering Chemistry, vol. 32, No. 12, Dec. 1940, pp. 1639-1641.
Egelhoff W.F. , "Thermochemical Values for Cu—Ni Surface and Interface Segregation Deduced from Core-Level Binding-Energy Shifts", Physical Review Letters, vol. 50, No. 8, Feb. 21, 1983, pp. 587-590.
El Hage et al., "Characterization of Milled Wood Lignin and Ethanol Organosolv Lignin from Miscanthus", Polymer Degradation and Stability, vol. 94, No. 10, 2009, pp. 1632-1638.
Ferrando et al., "Nanoalloys: From Theory to Applications of Alloy Clusters and Nanoparticles", Chemical Reviews, vol. 108, No. 3, 2008, pp. 845-910.
Gallo et al., "Production and Upgrading of 5-Hydroxymethylfurfural Using Heterogeneous Catalysts and Biomass-Derived Solvents", Green Chemistry, vol. 15, 2013, pp. 85-90.
Gao et al., "Pd—Au Bimetallic Catalysts: Understanding Alloy Effects from Planar Models and (Supported) Nanoparticles", Chemical Society Reviews, vol. 41, No. 24, Jul. 23, 2012, pp. 8009-8020(12 pages).
Garcia-Olmo et al., "Insights into the Activity, Selectivity and Stability of Heterogeneous Catalysts in the Continuous Flow Hydroconversion of Furfural", Catalysis Science & Technology, vol. 6, No. 13, 2016, pp. 4705-4711.
Gawande et al., "Cu and Cu-Based Nanoparticles: Synthesis and Applications in Catalysis", Chemical Reviews, vol. 116, No. 6, Mar. 23, 2016, pp. 3722-3811.

(56) References Cited

OTHER PUBLICATIONS

Ghasemi et al., "Enhanced Photocatalytic Degradation and Mineralization of Furfural Using UVC/TiO2/GAC Composite in Aqueous Solution", International Journal of Photoenergy, vol. 2016, Article ID 2782607, 2016, pp. 1-10.
Gong et al., "Highly Selective Liquid-Phase Hydrogenation of Furfural over N-doped Carbon Supported Metallic Nickel Catalyst under Mild Conditions", Journal of Molecular Catalysis A:Chemical, vol. 429, Dec. 2016, pp. 51-59.
Greeley et al., "Alloy Catalysts Designed from First Principles", Nature Materials, vol. 3, Nov. 2004, pp. 810-815.
Guo et al., "Efficient Hydrogenolysis of 5-Hydroxymethylfurfural to 2,5-Dimethylfuran over a Cobalt and Copper Bimetallic Catalyst on N-Graphene-Modified Al2O3†", Green Chemistry, vol. 18, 2016, pp. 6222-6228.
Gürbüz et al., "Reactive Extraction of Levulinate Esters and Conversion to γ-valerolactone for Production of Liquid Fuels", ChemSusChem, vol. 4, No. 3, Mar. 21, 2011, pp. 357-361.
Hallac et al., "Chemical Transformations of Buddleja davidii Lignin during Ethanol Organosolv Pretreatment", Energy & Fuels, vol. 24, 2010, pp. 2723-2732.
Han et al., "Transient Behavior of Ni@NiOx Functionalized SrTiO3 in Overall Water Splitting", ACS Catalysis, vol. 7, No. 3, Jan. 24, 2017, pp. 1610-1614.
Holewinski et al., "High-Performance Ag—Co Alloy Catalysts for Electrochemical Oxygen Reduction", Nature Chemistry, vol. 6, No. 9, Sep. 2014, pp. 828-834.
Hu et al., "Selective Transformation of 5-Hydroxymethylfurfural into the Liquid Fuel 2,5-Dimethylfuran over Carbon-Supported Ruthenium", Industrial & Engineering Chemistry Research Article, vol. 53, Feb. 2, 2014, pp. 3056-3064.
Hu et al., "Structural Characterization of Switchgrass Lignin after Ethanol Organosolv Pretreatment", Energy Fuels, vol. 26, No. 1, Dec. 22, 2011, pp. 740-745.
Huang et al., "Nickel-Tungsten Carbide Catalysts for the Production of 2,5-Dimethylfuran from Biomass-Derived Molecules", ChemSusChem, vol. 7, No. 4, Apr. 2014, pp. 1068-1072.
Huang et al., "Weighting Variation of Water-Gas Shift in Steam Reforming of Methane over Supported Ni and Ni—Cu Catalysts", Industrial & Engineering Chemistry Research, vol. 45, No. 1, 2006, pp. 150-156.
Huber et al., "Production of Liquid Alkanes by Aqueous-Phase Processing of Biomass-Derived Carbohydrates", Science, vol. 308, Jun. 3, 2005, pp. 1446-1450.
Huber et al., "Synthesis of Transportation Fuels from Biomass: Chemistry, Catalysts, and Engineering", Chemical Reviews, vol. 106, No. 9, 2006, pp. 4044-4098.
Jossens et al., "Fouling of a Platinum-Rhenium Reforming Catalyst Using Model Reforming Reactions", Journal of Catalysis, vol. 76, No. 2, 1982, pp. 265-273.
Kong et al., "Rational Design of Ni-Based Catalysts Derived from Hydrotalcite for Selective Hydrogenation of 5-Hydroxymethylfurfural†", Green Chemistry, vol. 17, 2015, pp. 2504-2514.
Kunkes et al., "Catalytic Conversion of Biomass to Monofunctional Hydrocarbons and Targeted Liquid-fuel Classes", Science, vol. 322, Iss. 5900, Oct. 17, 2008, pp. 417-421.
Kyriakou et al., "Isolated Metal Atom Geometries as a Strategy for Selective Heterogeneous Hydrogenations", Science, vol. 335, Mar. 9, 2012, pp. 1209-1212.
Lange et al., "Furfural—A Promising Platform for Lignocellulosic Biofuels", ChemSusChem, vol. 5, 2012, pp. 150-166.
Larsson et al., "Combustion of CO and Toluene; Characterisation of Copper Oxide Supported on Titania and Activity Comparisons with Supported Cobalt, Iron, and Manganese Oxide", Journal of Catalysis, vol. 163, 1996, pp. 279-293.
Larsson et al., "Complete Oxidation of CO, Ethanol, and Ethyl Acetate over Copper Oxide Supported on Titania and Ceria Modified Titania", Journal of Catalysis, vol. 179, No. 1, Oct. 1998, pp. 72-89.

Li et al., "Acid Reactions of Lignin Models of β5 Type", Holzforschung, vol. 53, No. 1, 1999, pp. 39-42.
Li et al., "Furfural: A Promising Platform Compound for Sustainable Production of C4 and C5 Chemicals", ACS Catalysis, vol. 6, No. 11, Sep. 28, 2016, pp. 7621-7640.
Li et al., "Self-Regenerative Activity of Ni/Mg(Al)O Catalysts with Trace Ru during Daily Start-up and Shut-down Operation of CH4 Steam Reforming", Journal of Catalysis, vol. 250, No. 2, 2007, pp. 299-312.
Li et al., "Synthesis of Diesel or Jet Fuel Range Cycloalkanes with 2-Methylfuran and Cyclopentanone from Lignocellulose", Energy Fuels, vol. 28, No. 8, Jul. 9, 2014, pp. 5112-5118.
Li et al., "Synthesis of Renewable Diesel with Hydroxyacetone and 2-methyl-furan", Chemical Communications, vol. 49, No. 51, 2013, pp. 5727-5729.
Lin et al., "High Performance of Ir-Promoted Ni/Tio2 Catalyst toward the Selective Hydrogenation of Cinnamaldehyde", Journal of Catalysis, vol. 303, 2013, pp. 110-116.
Lin et al., "Hydrogen production by Water-Gas Shift Reaction over Bimetallic Cu—Ni Catalysts Supported on La-doped Mesoporous Ceria", Applied Catalysis A: General, vol. 387, 2010, pp. 87-94.
Lin et al., "The Critical Role of Heterogeneous Catalysis in Lignocellulosic Biomass Conversion", Energy & Environmental Science, vol. 2, No. 1, 2009, pp. 68-80.
Liu et al., "Tackling CO Poisoning with Single-Atom Alloy Catalysts", Journal of the American Chemical Society, vol. 138, No. 20, May 25, 2016, pp. 6396-6399.
Luo et al., "Comparison of HMF Hydrodeoxygenation over Different Metalcatalysts in a Continuous Flow Reactor", Applied Catalysis A: General, vol. 508, 2015, pp. 86-93.
Luo et al., "Mechanisms for High Selectivity in the Hydrodeoxygenation of 5-Hydroxymethylfurfural over PtCo Nanocrystals", ACS Catalysis, vol. 6, May 20, 2016, pp. 4095-4104.
Luo et al., "The H2 Pressure Dependence of Hydrodeoxygenation Selectivities for Furfural Over Pt/C Catalysts", Catalysis Letters, vol. 146, No. 4, Apr. 2016, pp. 711-717.
Lynd et al., "Fuel Ethanol from Cellulosic Biomass", Science, vol. 251, Mar. 15, 1991, pp. 1318-1323.
Lynd et al., "How Biotech can Transform Biofuels", Nature Biotechnology, vol. 26, No. 2, Feb. 2008, pp. 169-172.
Marino et al., "Hydrogen from Steam Reforming of Ethanol Characterization and Performance of Copper-Nickel Supported Catalysts", International Journal of Hydrogen Energy, vol. 23, No. 12, 1998, pp. 1095-1101.
Mariño et al., "Cu—Ni—K/Gamma Al2O3 Supported Catalysts for Ethanol Steam Reforming Formation of Hydrotalcite-Type Compounds as a Result of Metal-Support Interaction", Applied Catalysis A: General, vol. 238, 2003, pp. 41-54.
Mariscal et al., "Furfural: A Renewable and Versatile Platform Molecule for the Synthesis of Chemicals and Fuels", Energy & Environmental Science, vol. 9, No. 4, 2016, pp. 1144 1189.
Matson et al., "One-Pot Catalytic Conversion of Cellulose and of Woody Biomass Solids to Liquid Fuels", Journal of the American Chemical Society, vol. 133, No. 35, Aug. 1, 2011, pp. 14090-14097.
Matsubu et al., "Adsorbate-Mediated Strong Metal-Support Interactions in Oxide-Supported Rh Catalysts", Nature Chemistry, vol. 9, Sep. 2016, pp. 120-127.
Michaelides et al., "Identification of General Linear Relationships Between Activation Energies and Enthalpy Changes for Dissociation Reactions at Surfaces", Journal of the American Chemical Society, vol. 125, No. 13, Mar. 5, 2003, pp. 3704-3705.
Mostofian et al., "Local Phase Separation of Co-Solvents Enhances Pretreatment of Biomass for Bioenergy Applications", Journal of the American Chemical Society, vol. 138, No. 34, 2016, pp. 10869-10878.
Nagaraja et al., "Vapor Phase Selective Hydrogenation of Furfural to Furfuryl Alcohol over Cu—MgO Coprecipitated Catalysts", Journal of Molecular Catalysis A: Chemical, vol. 265, 2007, pp. 90-97.
Naghash et al., "Coprecipitation of Nickel-Copper-Aluminum Takovite as Catalyst Precursors for Simultaneous Production of Carbon Nanofibers and Hydrogen", Chemistry of Materials, vol. 17, No. 4, 2005, pp. 815-821.

(56) References Cited

OTHER PUBLICATIONS

Naghash et al., "XRD and XPS Study of Cu—Ni Interactions on Reduced Copper-Nickel-Aluminum Oxide Solid Solution Catalysts", Chemistry of Materials, vol. 18, No. 10, May 2006, pp. 2480-2488.
Nagpure et al., "Efficient Preparation of Liquid Fuel 2,5-Dimethylfuran from Biomass-Derived 5-Hydroxymethylfurfural over Ru—NaY Catalyst", ACS Sustainable Chemistry & Engineering, vol. 3, No. 11, Oct. 12, 2015, pp. 2909-2916.
Nakagawa et al., "Catalytic Reduction of Biomass-Derived Furanic Compounds with Hydrogen", ACS Catalysis, vol. 3, Iss. 12, Oct. 6, 2013, pp. 2655-2668.
Nelson et al., "Experimental and Theoretical Insights into the Hydrogen-Efficient Direct Hydrodeoxygenation Mechanism of Phenol over Ru/TiO2", ACS Catalysis, vol. 5, Sep. 17, 2015, pp. 6509-6523.
Nerlov et al., "Promotion Through Gas Phase Induced Surface Segregation: Methanol Synthesis from CO, CO2 and H2 over Ni/Cu(100)", Catalysis Letters, vol. 54, 1998, pp. 171-176.
Nikolla et al., "Promotion of the Long-Term Stability of Reforming Ni Catalysts by Surface Alloying", Journal of Catalysis, vol. 250, No. 1, Aug. 2007, pp. 85-93.
Nørskov et al., "Universality in Heterogeneous Catalysis", Journal of Catalysis, vol. 209, No. 2, 2002, pp. 275-278.
O'Neill et al., "Control of Thickness and Chemical Properties of Atomic Layer Deposition Overcoats for Stabilizing Cu/g—Al2O3 Catalysts", ChemSusChem, vol. 7, 2014, pp. 3247-3251.
O'Neill et al., "Operando X-ray Absorption Spectroscopy Studies of Sintering for Supported Copper Catalysts during Liquidphase Reaction", ChemCatChem, vol. 6, 2014, pp. 2493-2496.
O'Neill et al., "Stabilization of Copper Catalysts for Liquid-Phase Reactions by Atomic Layer Deposition", Angewandte Chemie International Edition, vol. 52, 2013, pp. 13808-13812.
Oh et al., "Platinum-rhodium synergism in three-way automotive catalysts", Journal of Catalysis, vol. 98, No. 1, Mar. 1986, pp. 178-190.
Olcay et al., "Production of Renewable Petroleum Refinery Diesel and Jet Fuel Feedstocks From Hemicellulose Sugar Streams", Energy & Environmental Science, vol. 6, No. 1, 2013, pp. 205-216.
Omotoso et al., "Understanding the Role of Tio2 Crystal Structure on the Enhanced Activity and Stability of Ru/Tio2 Catalysts for the Conversion of Lignin-Derived Oxygenates†", Green Chemistry, vol. 16, 2014, pp. 645-652.
Padama et al., "CO-Induced Pd Segregation and The Effect of Subsurface Pd on CO Adsorption on Cupd Surfaces", Journal of Physics: Condensed Matter, vol. 29, No. 2, 2017, 8 pages.
Pan et al., "Determination of Atomic Ni Interaction with TiO2 by XPS †", Surface and Interface Analysis, vol. 42, 2010, pp. 878-881.
Pan et al., "Regioselective Atomic Rearrangement of Ag—Pt Octahedral Catalysts by Chemical Vapor-Assisted Treatment", Nano Letters, vol. 16, Nov. 28, 2016 Letter pubs.acs.org/NanoLett© , pp. 7988-7992.
Pang et al., "Synergistic Effects of Alloying and Thiolate Modification in Furfural Hydrogenation over Cu-Based Catalysts", The Journal of Physical Chemistry Letters Letter, vol. 5, Nov. 11, 2014 Letter pubs.acs.org/JPCL © , pp. 4110-4114.
Park et al., "Chemical reaction of Sputtered Cu Film with PI Modified by Low Energy Reactive Atomic Beam", Applied Surface Science, vol. 252, 2006, pp. 5877-5891.
Pei et al., "Ag Alloyed Pd Single-Atom Catalysts for Efficient Selective Hydrogenation of Acetylene to Ethylene in Excess Ethylene", ACS Catalysis, vol. 5, Iss. 6, May 5, 2015, pp. 3717-3725.
Perlack et al., "U.S. Billion-Ton Update: Biomass Supply for a Bioenergy and Bioproducts Industry", United States Department of Energy, 2011, 235 pages.
Wu et al., "Efficient and Versatile CuNi Alloy Nanocatalysts for the Highly Selective Hydrogenation of Furfural", Applied Catalysis B: Environmental, vol. 203, Apr. 2017, pp. 227-236.
Wu et al., "In Situ Observation of Cu—Ni Alloy Nanoparticle Formation by X-Ray Diffraction, X-Ray Absorption Spectroscopy, and Transmission Electron Microscopy: Influence of Cu/Ni Ratio", ChemCatChem, vol. 6, 2014, pp. 301-310.
Wyman Charlese. , "Research and Development Needs for a Fully Sustainable Biocommodity Industry", Advancing Sustainability through Green Chemistry, Chapter 3, Jul. 19, 2002, 18 pages.
Wyman et al., "What Could Be Possible With Mature Biofuels Technologies?", Biofuels, Bioproducts and Biorefining, vol. 3, No. 2, 2009, pp. 105-107.
Xia et al., "Efficient Conversion of Wheat Straw into Furan Compounds, Bio-Oils, and Phosphate Fertilizers by a Combination of Hydrolysis and Catalytic Pyrolysis", RSC Advances, vol. 7, 2017, pp. 1200-1205.
Xin et al., "Predictive Structure-Reactivity Models for Rapid Screening of Pt-Based Multimetallic Electrocatalysts for the Oxygen Reduction Reaction", ACS Catalysis, vol. 2, No. 1, Nov. 16, 2011, pp. 12-16.
Xiong et al., "Reaction Pathways of Furfural, Furfuryl Alcohol and 2-Methylfuran on Cu(111) and Nicu Bimetallic Surfaces", Surface Science, vol. 652, Feb. 2016, pp. 91-97.
Yamaguchi et al., "Nitrogen Dissociation via Reaction with Lithium Alloys", Acs Omega, vol. 2, No. 3, Mar. 22, 2017, pp. 1081-1088.
Yan et al., "Selective Hydrogenation of Furfural and Levulinic acid to Biofuels on the Ecofriendly Cu—Fe Catalyst", Fuel, vol. 115, 2014, pp. 101-108.
Yang et al., "Aqueous Phase Hydrogenation of Furfural to Tetrahydrofurfuryl Alcohol on Alkaline Earth Metal Modified Ni/Al2O3", RSC Advances, vol. 6, 2016, pp. 51221-51228.
Yao et al., "In situ IR Spectroscopic Studies of Ni Surface Segregation Induced by CO Adsorption on Cu—Ni/SiO2 Bimetallic Catalysts", Physical Chemistry Chemical Physics, vol. 16, No. 8, Feb. 28, 2014, pp. 3823-3829.
Yi et al., "The Composition and Structure of Pd—Au Surfaces", The Journal of Physical Chemistry B, vol. 109, No. 39, Oct. 9, 2005, pp. 18535-18540.
Zhang et al., "Ethanol Steam Reforming over Ni—Cu/Al2O3-MyOz (M= Si, La, Mg, and Zn ) Catalysts", Journal of Natural Gas Chemistry, vol. 18, No. 1, 2009, pp. 55-65.
Zhang et al., "Sugar Yields from Dilute Oxalic Acid Pretreatment of Maple Wood Compared to those with Other Dilute Acids and Hot Water", Carbohydrate Polymers, vol. 92, No. 1, 2013, pp. 334-344.
Zheng et al., "Towards Understanding the Reaction Pathway in Vapour Phase Hydrogenation of Furfural to 2-Methylfuran", Journal of Molecular Catalysis A: Chemical, vol. 246, 2006, pp. 18-23.
Zhu et al., "Efficient Synthesis of 2,5-Dihydroxymethylfuran and 2,5-Dimethylfuran from 5-Hydroxymethylfurfural using Mineral-Derived Cu Catalysts as Versatile Catalysts", Catalysis Science & Technology, vol. 5, 2015, pp. 4208-4217.
Perret et al., "Catalytic Response and Stability of Nickel/Alumina for the Hydrogenation of 5-Hydroxymethylfurfural in Water", ChemSusChem, vol. 9, Feb. 12, 2016, pp. 521-531.
Ponec Vladimir, "Alloy Catalysts: The Concepts", Applied Catalysis A: General, vol. 222, Iss. 1-2, Dec. 20, 2001, pp. 31-45.
Pu et al., "Application of Quantitative 31P NMR in Biomass Lignin and Biofuel Precursors Characterization", Energy & Environmental Science, vol. 4, 2011, pp. 3154-3166.
Ragauskas et al., "Lignin Valorization: Improving Lignin Processing in the Biorefinery", Science, vol. 344, May 16, 2014, 11 pages.
Rao et al., "Furfural Hydrogenation over Carbon-Supported Copper", Catalysis Letters, vol. 60, 1999, pp. 51-57.
Rao et al., "Nature and Catalytic Activity of Bimetallic CuNi Particles on CeO2 Support", Catalysis Today, vol. 198, 2012, pp. 140-147.
Rao et al., "Properties of Copper Chromite Catalysts in Hydrogenation Reactions", Journal of Catalysis, No. 171, Article No. CA971832, 1997, pp. 406-419.
Rasser et al., "Characterization and Performance of Platinum-Iridium Reforming Catalysts", Journal of Catalysis, vol. 59, No. 2, Oct. 15, 1979, pp. 211-222.
Robertson et al., "Study of Copper-Nickel Alloy Formation on Silica Supports by the Magnetostatic and Other Methods", Journal of Catalysis, vol. 39, No. 2, Aug. 1975, pp. 234-248.

(56) References Cited

OTHER PUBLICATIONS

Rogatis et al., "NixCuy/Al2O3 Based Catalysts for Hydrogen Production", Energy & Environmental Science, vol. 1, 2008, pp. 501-509.
Roman-Leshkov et al., "Production of Dimethylfuran for Liquid Fuels from Biomass-Derived Carbohydrates", Nature, vol. 447, Jun. 21, 2007, pp. 982-985 (5 pages).
Ruban et al., "Surface Segregation Energies in Transition-Metal Alloys", Physical Review B, vol. 59, No. 24, Jun. 15, 1999, pp. 15990-16000.
Sadeghifar et al., "Fractionation of Organosolv Lignin Using Acetone: Water and Properties of the Obtained Fractions", ACS Sustainable Chemistry & Engineering, vol. 5, Nov. 7, 2016, pp. 580-587.
Sannigrahi et al., "Lignin Structural Modifications Resulting from Ethanol Organosolv Treatment of Loblolly Pine", Energy Fuels, vol. 24, 2010, pp. 683-689.
Schmidt et al., "Chemical Engineering: Hybrid Routes to Biofuels", Nature, vol. 447, Jun. 21, 2007, pp. 914-915.
Scholz et al., "Catalytic Transfer Hydrogenation/Hydrogenolysis for Reductive Upgrading of Furfural and 5-Hydroxymethyl)furfural", ChemSusChem, vol. 7, No. 1, Jan. 2014, pp. 268-275.
Seemala et al., "Effects of Cu—Ni Bimetallic Catalyst Composition and Support on Activity, Selectivity, and Stability for Furfural Conversion to 2-Methyfuran", ACS Sustainable Chemistry & Engineering, vol. 6, No. 2, Dec. 5, 2017, 11 pages.
Seemala et al., "Levulinic Acid as a Catalyst for the Production of 5-Hydroxymethylfurfural and Furfural from Lignocellulose Biomass", ChemCatChem, vol. 8, No. 3, Feb. 2016, pp. 640-647.
Seemala et al., "Support Induced Control of Surface Composition in Cu—Ni/TiO2 Catalysts Enables High Yield Co-Conversion of HMF and Furfural to Methylated Furans", ACS Catalysis, vol. 7, No. 6, May 8, 2017, pp. 4070-4082.
Shan et al., "Tuning Catalytic Performance through a Single or Sequential Post-Synthesis Reaction(s) in a Gas Phase", ACS Catalysis, vol. 7, Oct. 28, 2016, pp. 191-204.
Sheng et al., "Iron-Promotion of Silica-Supported Copper Catalysts for Furfural Hydrodeoxygenation", ChemCatChem, vol. 8, No. 21, Nov. 8, 2016, pp. 3402-3408.
Sinfelt JohnH., "Catalysis by Alloys and Bimetallic Clusters", Accounts of Chemical Research, vol. 10, Iss.1, Jan. 1, 1977, pp. 15-20.
Sinfelt et al., "Catalytic Hydrogenolysis and Dehydrogenation over Copper-Nickel Alloys", Journal of Catalysis, vol. 24, Iss 2, Feb. 1972, pp. 283-296.
Sitthisa et al., "Hydrodeoxygenation of Furfural Over Supported Metal Catalysts: A Comparative Study of Cu, Pd and Ni", Catalysis Letters, vol. 141, Jun. 2011, pp. 784-791.
Sitthisa et al., "Kinetics and Mechanism of Hydrogenation of Furfural on Cu/SiO2 Catalysts", Journal of Catalysis, vol. 277, No. 1, 2011, pp. 1-13.
Sitthisa et al., "Selective Conversion of Furfural to Methylfuran over Silica-Supported Ni—fe Bimetallic Catalysts", Journal of Catalysis, vol. 284, 2011, pp. 90-101.
Sluiter et al., "Determination of Structural Carbohydrates and Lignin in Biomass", National Renewable Energy Laboratory/TP-510-42618, 2012, 18 pages.
Smith et al., "Cosolvent Pretreatment in Cellulosic Biofuel Production: Effect of Tetrahydrofuran-Water on Lignin Structure and Dynamics", Green Chemistry, vol. 18, No. 5, 2016, pp. 1268-1277.
Srivastava et al., "A Versatile Bi-Metallic Copper-Cobalt Catalyst For Liquid Phase Hydrogenation of Furfural To 2-Methylfuran", RSC Advances, vol. 6, Iss. 2, 2016, pp. 1649-1658.
Srivastava et al., "Kinetics and Mechanism of Deactivation of PdAl2O3 Catalyst in the Gaseous Phase Decarbonylation of Furfural", Journal of Catalysis, vol. 91, No. 2, 1985, pp. 254-262.
Stevens et al., "Real-Time Product Switching Using a Twin Catalyst System for the Hydrogenation of Furfural in Supercritical CO2", Angewandte Chemie International Edition, vol. 49, 2010, pp. 8856-8859.
Studt et al., "CO Hydrogenation to Methanol on Cu—Ni Catalysts: Theory and Experiment", Journal of Catalysis, vol. 293, 2012, pp. 51-60.
Swift et al., "Investigation of the Metallic Phases in Reduced, Impregnated Nickel and Nickel-Copper Silica-Alumina Catalysts", The Journal of Physical Chemistry, vol. 69, No. 10, Oct. 1, 1965, pp. 3268-3274.
Tao et al., "Reaction-Driven Restructuring of Rh—Pd and Pt—Pd Core-Shell Nanoparticles", Science, vol. 322, Nov. 7, 2008, pp. 932-934 (5 pages).
Tauster S.J., "Strong Metal-Support Interactions", Accounts of Chemical Research, vol. 20, No. 11, Nov. 1, 1987, pp. 389-394.
Tauster et al., "Strong Metal-Support Interactions. Group 8 Noble Metals Supported on TiO2", Journal of the American Chemical Society, vol. 100, No. 1, Jan. 1978, pp. 170-175.
Thananatthanachon et al., "Efficient Production of the Liquid Fuel 2,5-Dimethylfuran from Fructose Using Formic Acid as a Reagent", Angewandte Chemie International Edition, vol. 49, 2010, pp. 6616-6618.
Tolbert et al., "Characterization and Analysis of The Molecular Weight of Lignin For Biorefining Studies", Biofuels, Bioproducts and Biorefining, vol. 8, No. 6, 2014, pp. 836-856.
Uchiyama et al., "Production of Higher Alcohols from Synthesis Gas over Nickel Containing Catalysts: Effects of Adding Copper and Sodium to Coprecipitated Nio Tio2 Catalysts", Applied Catalysis, vol. 42, Iss. 1, Aug. 15, 1988, pp. 143-152.
Ungureanu et al., "Synthesis of Highly Thermostable Copper-Nickel Nanoparticles Confined in the Channels of Ordered Mesoporous SBA-15 Silica", Journal of Materials Chemistry, vol. 21, 2011, pp. 12529-12541.
Vargas-Hernández et al., "Furfuryl alcohol from Furfural Hydrogenation over Copper Supported on SBA-15 Silica Catalysts", Journal of Molecular Catalysis A: Chemical, vol. 383-384, Mar. 2014, pp. 106-113.
Vu et al., "Pt—Sn Alloy Phases and Coke Mobility over Pt—Sn/Al2O3 and Pt—Sn/Znal2o4 Catalysts for Propane Dehydrogenation", Applied Catalysis A: General, vol. 400, Apr. 29, 2011, pp. 25-33.
Wandelt et al., "Evidence for Crystal-Face Specificity in Surface Segregation of CuNi Alloys", Physical Review Letters, vol. 46, No. 23, Jun. 8, 1981, pp. 1529-1532.
Wang et al., "Decomposition of Methane over a Ni—Cu—MgO Catalyst to Produce Hydrogen and Carbon Nanofibers", The Journal of Physical Chemistry B, vol. 108, No. 52, 2004, pp. 20273-20277.
Wang et al., "Efficient Catalytic Conversion of Lignocellulosic Biomass into Renewable Liquid Biofuels Via Furan Derivatives", RSC Advances, vol. 4, 2014, pp. 31101-31107.
Wang et al., "Ethanol Steam Reforming over Ni and Ni—Cu Catalysts", Catalysis Today, vol. 146, 2009, pp. 31-36.
Webber et al., "A Combined XPS/AES Study of Cu Segregation to the High and Low Index Surfaces of a Cu—Ni Alloy", Surface Science, vol. 105, 1981, pp. 20-40.
Wen et al., "Characterization and Catalytic Properties of the Ni/Al2O3 Catalysts for Aqueous-phase Reforming of Glucose", Catalysis Letters, vol. 129, No. 1, Apr. 2009, pp. 250-257.
Wolfbeisser et al., "Surface Composition Changes of CuNi—ZrO2during Methane Decomposition: An Operando NAP-XPS and Density Functional Study", Catalysis Today, vol. 283, Apr. 1, 2017, pp. 134-143.
Wolfbeisser et al., "Surface Modification Processes During Methane Decomposition on Cu-Promoted Ni—Zro2 Catalysts", Catalysis Science & Technology, vol. 5, 2015, pp. 967-978.

\* cited by examiner

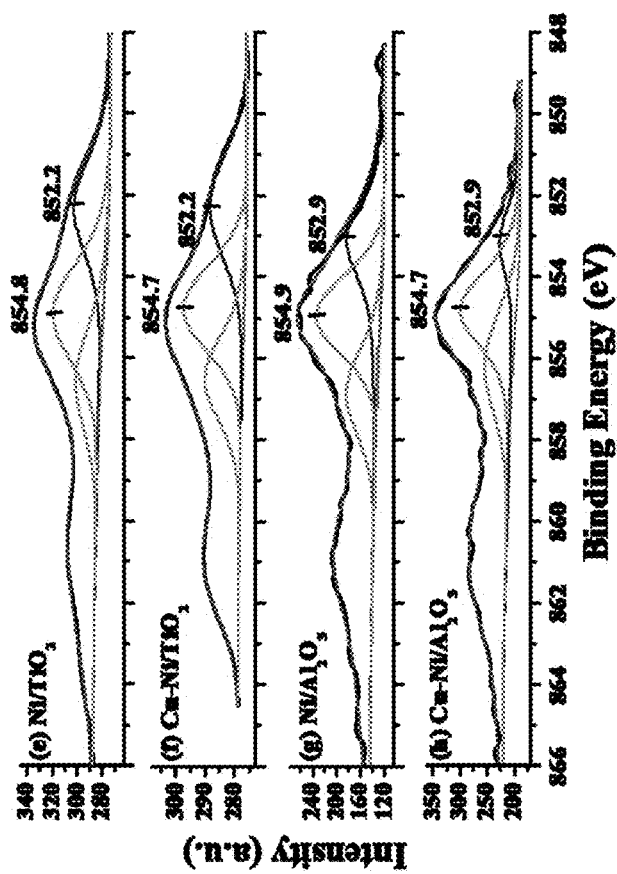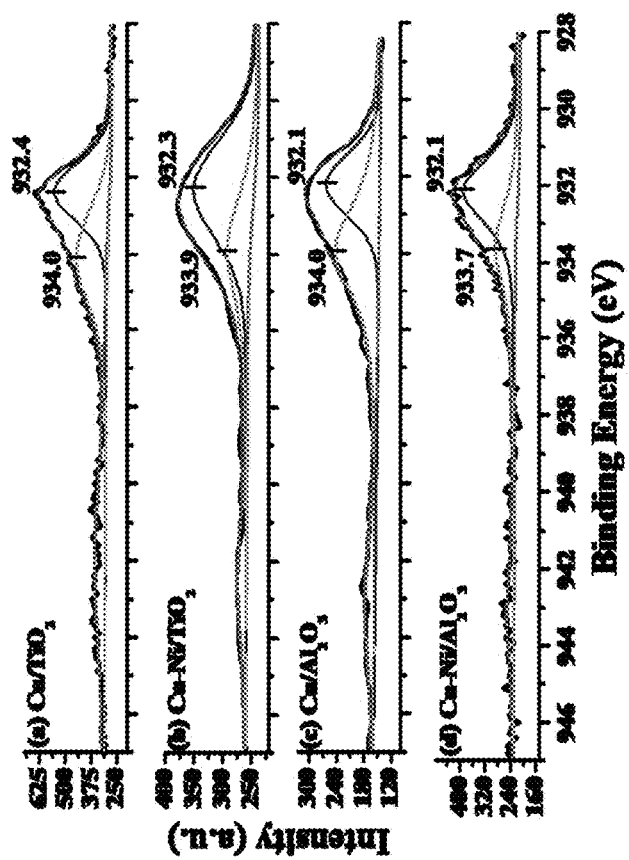
FIGS. 2(a)-2(h)

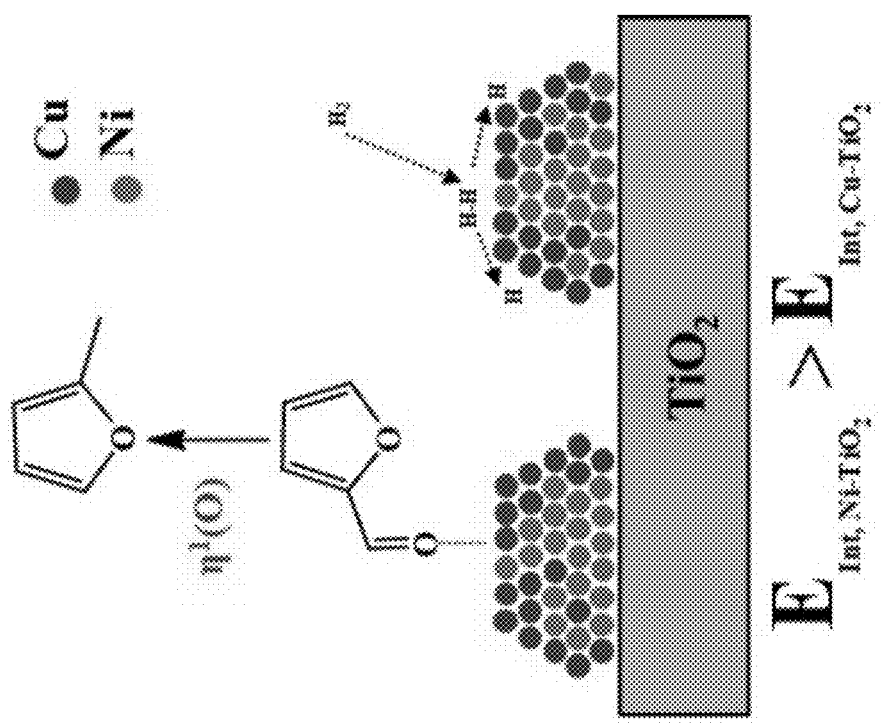
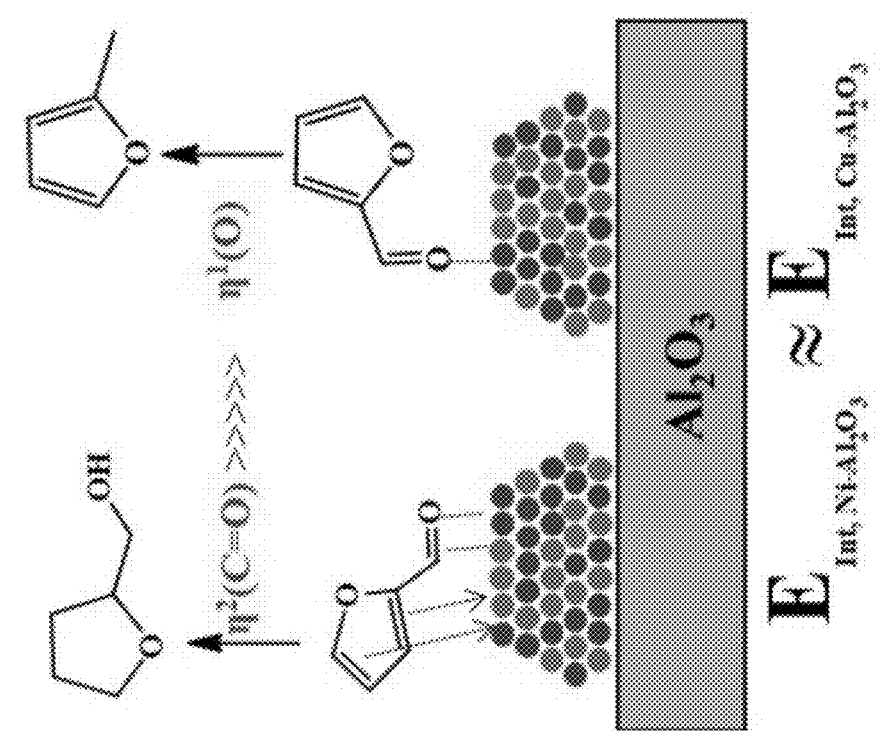
FIG. 10

Table 1. Physicochemical properties of monometallic Cu, Ni and bimetallic Cu-Ni catalysts supported on $Al_2O_3$ and $TiO_2$

| Sample | Specific surface area ($S_{BET}$, m²/g) | Particle size distribution from TEM (nm) | $H_2$-Uptake (TPR; mmol/g) | Cu/Ni Surface Composition $Cu^{2+}/Cu^0$ | $Ni^{2+}/Ni^0$ | Cu/Ni $(Cu^0+Cu^{+2})/(Ni^0+Ni^{+2})$ |
|---|---|---|---|---|---|---|
| θ-$Al_2O_3$ | 79.7 | - | - | - | - | - |
| $TiO_2$(P25) | 54.3 | - | - | - | - | - |
| Cu(10 wt%)/$Al_2O_3$ | 64.0 | 7.0±1.6 | 1.29 | 37.6/62.4 | - | - |
| Cu(10 wt%)/$TiO_2$ | 43.4 | 8.0±3.5 | 1.48 | 47.8/52.2 | - | - |
| Ni(10 wt%)/$Al_2O_3$ | 64.8 | 6.4±5.1 | 1.68 | - | 52.4/47.7 | - |
| Ni(10 wt%)/$TiO_2$ | 47.2 | 9.9±2.6 | 1.75 | - | 57.5/42.7 | - |
| Cu(5 wt%)-Ni(5 wt%)/$Al_2O_3$ | 67.4 | 4.9±1.6 | 1.62 | 38.6/61.4 | 73.7/26.3 | 48.7/51.3[b] |
| Cu(5 wt%)-Ni(5 wt%)/$TiO_2$ | 45.9 | 7.5±3.9 | 1.56 | 33.1/66.9 | 57.5/42.5 | 82.4/17.6[b] |
| Cu(5 wt%)-Ni(5 wt%)/$Al_2O_3$[a] | - | - | - | - | - | 47.2/52.8 |
| Cu(5 wt%)-Ni(5 wt%)/$TiO_2$[a] | - | - | - | - | - | 82.4/17.6 |

FIG. 13

Table 2. Hydrodeoxygenation of FF to methyl furan over Ni & Cu-supported over $\gamma$-$Al_2O_3$ and $TiO_2$ (P25)

| Run no. | Catalyst | Conv. | Yield % | | | | |
|---|---|---|---|---|---|---|---|
| | | | FOL | MF | furan | THFOL | 1, 2 pent diol |
| 1 | Ni(10 wt%)/$Al_2O_3$ | 26.5 | 12.3 | 2.8 | 0.0 | 1.2 | 4.1 |
| 2 | Ni(10 wt%)/$TiO_2$ | 21.5 | 7.5 | 1.1 | 0.0 | 3.1 | 5.2 |
| 3 | Cu(10 wt%)/$Al_2O_3$ | 16.3 | 8.9 | 0 | 0.0 | 0 | 0.8 |
| 4 | Cu(10 wt%)/$TiO_2$ | 7.5 | 4.1 | 1.3 | 0.0 | 0 | 1.1 |
| 5 | Ni(5wt%)–Cu(5wt%)/$Al_2O_3$ | 30.4 | 11.3 | 4.4 | 9.4 | 0.2 | 2.2 |
| 6 | Ni(5 wt%)–Cu(5 wt%)/$TiO_2$ | 16.2 | 8.5 | 1.7 | 0.0 | 0 | 2.9 |

*Reaction conditions: Furfural (FF) = 1 g, Catalyst = 0.050 g, Iso-propanol = 25 ml, $H_2$-pressure = 25 bar, Temp. = 180 °C, Reaction time = 1 h*

FIG. 22

Table 3. Activity of bimetallic Ni-Cu/$\gamma$-$Al_2O_3$ catalysts to FF hydrogenation compared to Ni-Cu/ $TiO_2$

| Run No. | Time (h) | Conv. | Yield % | | | | |
|---|---|---|---|---|---|---|---|
| | | | FOL/(sel. FOL+ MF) | MF | Furan | THFOL | 1, 2 pent diol |
| 1 | 1 | 30.4 | 11.3(51.6) | 4.4 | 9.4 | 0.1 | 2.2 |
| 2 | 2 | 54.9 | 25.7(53.6) | 3.7 | 10.7 | 0.5 | 4.3 |
| 3 | 4 | 69.6 | 37.9(62.9) | 5.9 | 8.9 | 2.1 | 5.1 |
| 4 | 6 | 77.4 | 42.7(65.4) | 7.9 | 10.4 | 1.9 | 6.5 |
| 5 | $^a$6 | 50.6 | 32.4(78.7) | 7.4 | 0 | 0.4 | 6.7 |

*Reaction conditions: Furfural (FF) = 1 g, Catalyst [Ni (5wt%)-Cu(5wt%)/$Al_2O_3$] = 0.050 g, Iso-propanol = 25 ml, Reaction temperature = 180°C.*
*$^a$ Catalyst [Ni (5wt%)-Cu(5wt%)/$TiO_2$] = 0.050 g*

FIG. 23

Table 4. Effect of temperature on FF hydrogenation over Ni/γ-Al$_2$O$_3$

| Run no. | Temp.(°C)/H$_2$-pressure (bar) | Conv. | Yield % | | | | |
|---|---|---|---|---|---|---|---|
| | | | FOL | MF | furan | THFOL | 1, 2 pent diol |
| 1 | 180/25 | 26.5 | 12.3 | 2.8 | 0 | 1.2 | 4.1 |
| 2 | 210/25 | 50.3 | 16.1 | 5.6 | 22.8 | 1.9 | 3.4 |
| 3 | 240/25 | 83.9 | 25.9 | 7.3 | 39.0 | 3.6 | 2.3 |
| 4 | 240/15 | 43.2 | 15.4 | 3.8 | 20.8 | 0 | 0.9 |

*Reaction conditions: Furfural (FF) = 1 g, Catalyst [Ni (10 wt%)/Al$_2$O$_3$] = 0.050 g, Iso-propanol = 25 ml, Reaction time = 1 h.*

FIG. 24

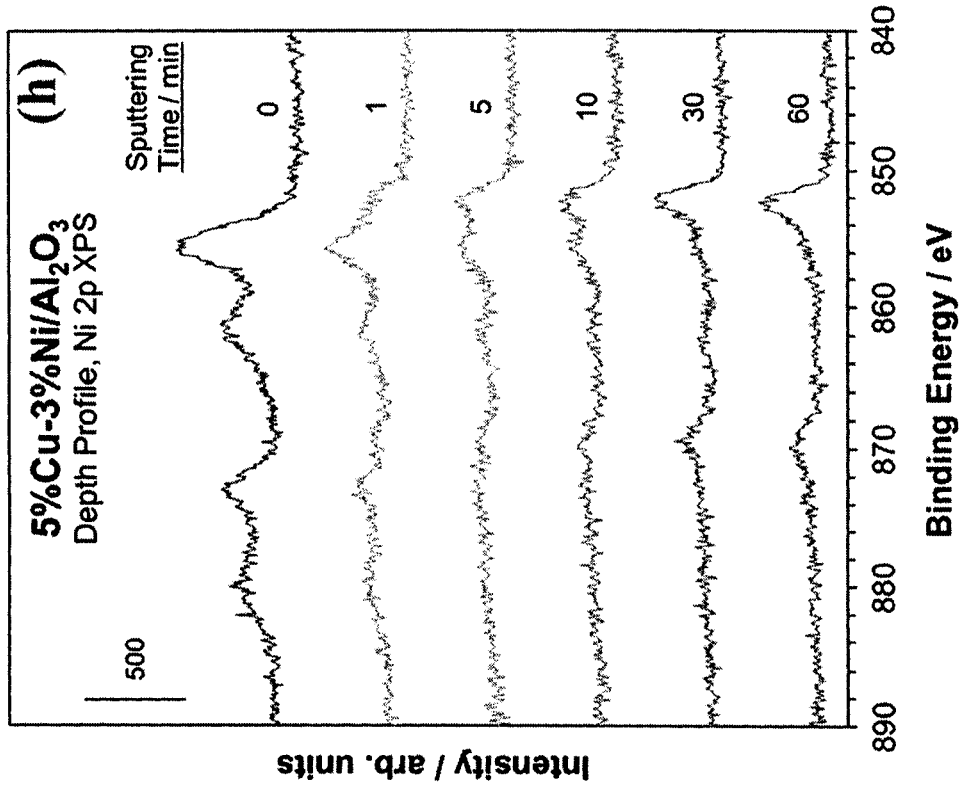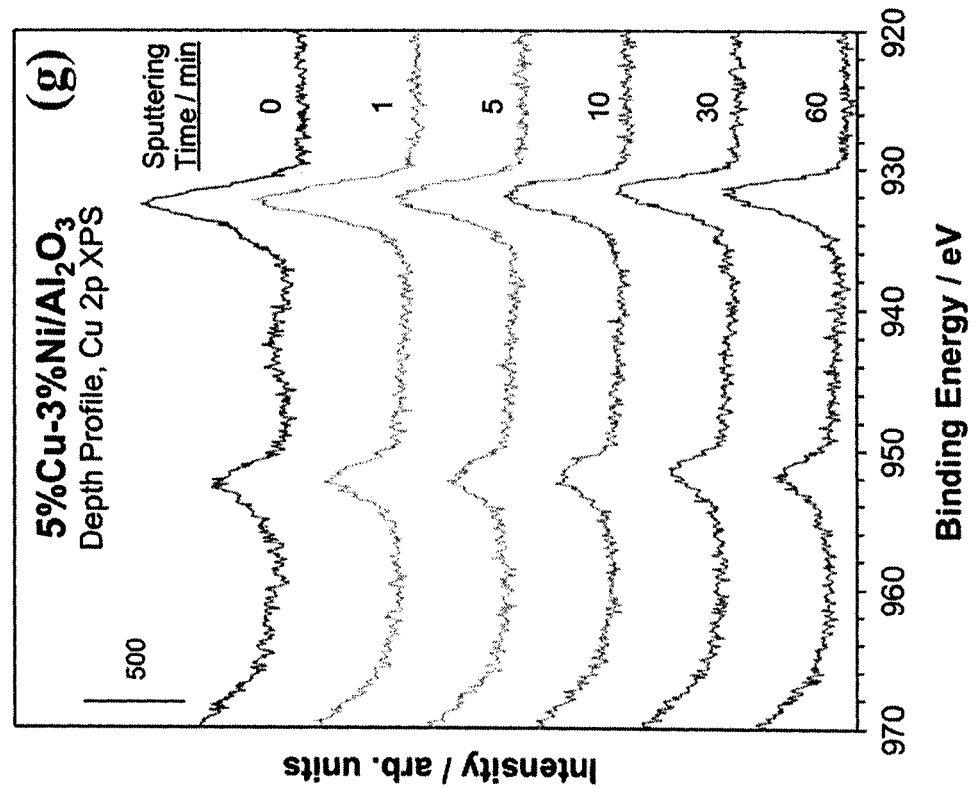
FIG. 37

Table 5. XPS Binding energy values derived from 2p3/2 peaks of $Cu^0$ and $Ni^0$ for catalysts of various composition and support.

| Catalyst | XPS Binding Energy (eV) | |
|---|---|---|
| | $Cu^0$ | $Ni^0$ |
| Cu(5%)-Ni(1.5%)/$TiO_2$ | 931.8 | 851.8 |
| Cu(5%)-Ni(3%)/$TiO_2$ | 932.2 | 852.3 |
| Cu(5%)-Ni(5%)/$TiO_2$ | 932.3 | 852.2 |
| Cu(5%)-Ni(1.5%)/$Al_2O_3$ | 932.2 | 852.5 |
| Cu(5%)-Ni(3%)/$Al_2O_3$ | 932.3 | 852.8 |
| Cu(5%)-Ni(5%)/$Al_2O_3$ | 923.1 | 852.9 |

FIG. 42

Table 6. The influence of $H_2$ pressure on FF conversion and product yields over Cu(5%)-Ni(0.5%)/$TiO_2$ catalyst. Reaction conditions: FF = 1 g, catalyst = 0.3 g, solvent (1, 4 dioxane) = 25 ml, reaction time = 8 h, reaction temperature = 200 °C.

| Run no. | $H_2$-Pressure (bar) | FF Conv. | FOL yield | MF yield |
|---|---|---|---|---|
| 1 | 25 | 85 | 2.5 | 43.4 |
| 2 | 35 | 100 | 0.0 | 91.1 |
| 3 | 45 | 100 | 0.0 | 90.3 |

FIG. 43

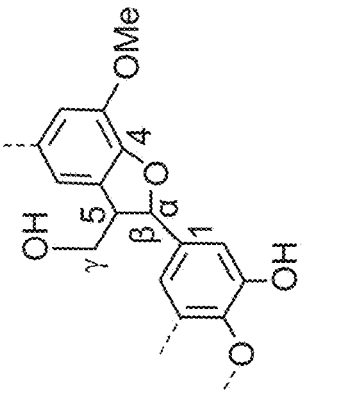
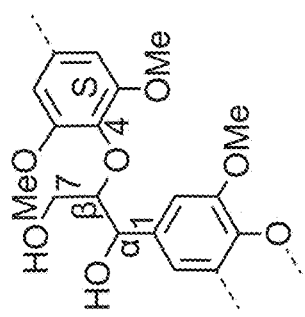
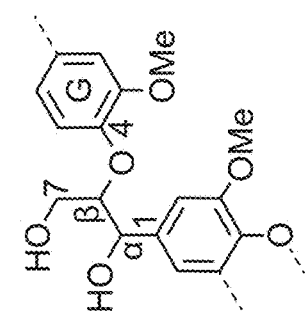
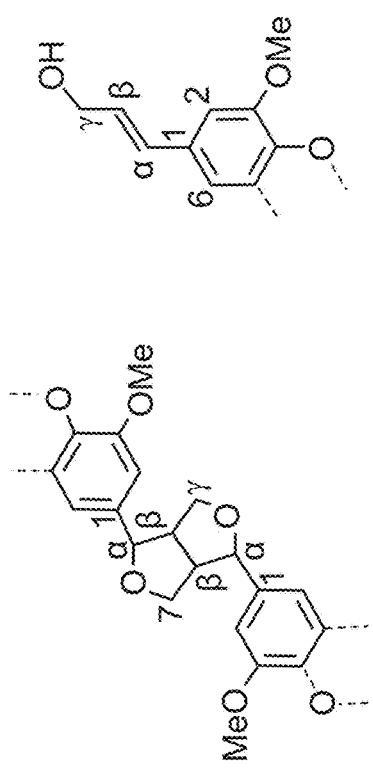
FIG. 53 (Cont.)

METHOD AND SYSTEM FOR HYBRID CATALYTIC BIOREFINING OF BIOMASS TO METHYLATED FURANS AND DEPOLYMERIZED TECHNICAL LIGNIN

CROSS-REFERENCE TO RELATED APPLICATION

This application claims priority to U.S. Provisional Application No. 62/640,305, filed on Mar. 8, 2018, and U.S. Provisional Application No. 62/640,406, filed on Mar. 8, 2018, the entire contents of both of which is incorporated herein by reference.

FIELD OF THE INVENTION

The disclosure relates to support induced control of surface composition in Cu—Ni/$TiO_2$ catalysts enabling high yield co-conversion of HMF and furfural to methylated furans, and hybrid catalytic biorefining of biomass to methylated furans and depolymerized technical lignin

BACKGROUND

Lignocellulosic biomass is one of the most abundant and inexpensive renewable resource that can potentially displace petroleum as a carbon neutral alternative for the production of fungible liquid transportation fuels and commodity chemicals. Examples of biomass can include but are not limited to biomass derived from corn, soy beans, tubers (e.g., potatoes, sweet potatoes), sugarcane, sorghum, cassava, grasses (e.g., switchgrass, Miscanthus, wheat, rice, barley, oats, millet, cassava), legumes, wood (e.g., maple, oak, poplar, pine) and other cellulose substrates, such as agricultural wastes (e.g., sugarcane bagasse, corn fiber, corn stover, wheat husk, rice husk). However, the production of target chemicals and gasoline range fuels from lignocellulosic biomass has been economically challenging due to the need for multiple processing steps and associated high product yields required in each step. Biomass is rich in both $C_6$ (glucan) and $C_5$ (xylan) polymeric sugars that can be converted by acid-catalyzed dehydration into 5-(hydroxymethyl)furfural (HMF) and furfural (FF), respectively, with relatively high yields. As such, HMF and FF have been identified as valuable fuel precursors suitable for the production of dimethyl furan (DMF) and methyl furan (MF), respectively, through selective hydrodeoxygenation (HDO) (hydrogenation followed by hydrogenolysis). Due to their high octane numbers, these methylated furans (DMF and MF) have been deemed as valuable target fuel products from biomass suitable for blending with gasoline. DMF and MF can also be selectively converted into $C_6$ and $C_5$ alcohols as direct gasoline replacements, or further converted into long chain hydrocarbons for diesel or jet fuel applications by condensation followed by deoxygenation. However, catalytic production of DMF and MF from biomass derived HMF and FF requires high yields and process simplicity.

Supported noble metal catalysts have been thoroughly studied for HDO of HMF and FF. To reduce costs and control toxicity from catalyst wastes, heterogeneous base metal catalysts, particularly first row transition metals such as Ni, Cu, Co, and Fe, are excellent choices. Undesired reactions such as decarbonylation and ring hydrogenation are common when using base metal catalysts (particularly Ni, Co and Fe), and the stability of these materials under reaction conditions is low at relatively high temperatures (e.g., >200° C.). FF conversion to MF occurs through hydrogenation to furfuryl alcohol (FOL) as an intermediate product, followed by hydrogenolysis to MF. Unwanted side reactions include ring hydrogenation of MF or FOL to form methyl tetrahydrofuran (MTHF), or tetrahydrofurfural alcohol (THFOL) and decarbonylation of FF to form furan, see Scheme 1 (FIG. 11). Cu catalysts minimize decarbonylation and ring hydrogenation due to their full valence d-band and effectively hydrogenate FF to FOL at relatively low temperatures (e.g., <200° C.). However, the low activity of Cu for $H_2$ activation and stronger interaction of Cu with FF, as compared to FOL, make conversion of FOL to MF on pure Cu catalysts slow. Cu-based bimetallic catalysts have been proposed to overcome the low reactivity of monometallic Cu for hydrogenation reactions. Various formulations have been proposed, such as Cu—Fe, Cu—Pd, Cu—Cr, and Cu—Ni, to increase reactivity or selectivity, but further enhancements in reactivity, selectivity towards MF, and catalyst stability are needed for economical implementation.

HMF conversion to DMF is known to occur through hydrogenation and hydrogenolysis of the alcohol and carbonyl groups, but undesirable products are formed through decarbonylation and ring hydrogenation reactions, see Scheme 2 (FIG. 12). Noble metals catalysts such as Ru, Pt, Pd, and their combination with Cu, Fe and Co in bimetallic catalysts have been reported for HMF conversion to DMF, although the requirement of Pt group metal catalysts is economically challenging for an industrial process. Limited reports exist on the successful use of solely first row transitions metals or non-noble metal catalyst systems for high yield conversion of HMF to DMF. Recently, it has been demonstrated that modifying Cu catalysts with Zn or Co and graphene enabled high selectivity for DMF production. However, in these reports low reactivity and stability, or expensive catalyst formulations (graphene) limit their commercial viability. Bi-functional Ni catalysts combining dispersed Ni species and acidic supports have also been demonstrated for HMF conversion to DMF with high yields, although these reports are limited by catalyst stability or require high $H_2$ pressures.

Base metal catalysts are generally most suitable for HDO of FF and HMF to methyl furans due to their low costs, but limited demonstrations of these catalysts are reported to achieve high reactivity, selectivity, and stability. Furthermore, it has recently been demonstrated that high yield co-production of HMF and FF can be achieved directly from biomass in a single step process using THF as a co-solvent, thereby enabling integrated downstream catalytic strategies to process a single product stream containing both HMF and FF to reduce overall processing costs. However, most previous reports on HMF and FF HDO have considered their catalytic conversion separately. It is expected that coupling base metal catalysts capable of simultaneously converting HMF and FF to methylated furans with recently developed biomass pre-treatment technologies could realize significant cost savings for an integrated processing strategy that avoids separating biomass sugar streams.

SUMMARY 5-(hydroxymethyl)furfural (HMF) and furfural (FF) have been identified as valuable biomass-derived fuel precursors suitable for catalytic hydrodeoxygenation (HDO) to produce high octane fuel additives such dimethyl furan (DMF) and methyl furan (MF), respectively. In order to realize economically viable production of DMF and MF from biomass, catalytic processes with high yields, low catalyst costs, and process simplicity are needed.

In accordance with an exemplary embodiment, a method and system for simultaneous co-processing of HMF and FF over Cu—Ni/TiO$_2$ catalysts is disclosed, achieving 87.5% yield of DMF from HMF and 88.5% yield of MF from FF in a one pot reaction. The Cu—Ni/TiO$_2$ catalyst also exhibited improved stability and regeneration compared to Cu/TiO$_2$ and Cu/Al$_2$O$_3$ catalysts for FF HDO, exhibiting an approximate 7% loss in FF conversion over 4 sequential recycles, compared to an approximate 50% loss in FF conversion for Cu/Al$_2$O$_3$ and an approximately 30% loss in conversion for Cu/TiO$_2$.

In accordance with an exemplary embodiment, characterization of the Cu—Ni/TiO$_2$ catalyst by X-ray Photoelectron Spectroscopy, Scanning Transmission Electron Microscopy, and H$_2$-Temperature Programmed Reduction and comparison to monometallic Cu and Ni on Al$_2$O$_3$ and TiO$_2$ and bimetallic Cu—Ni/Al$_2$O$_3$ catalysts suggest that the unique reactivity and stability of Cu—Ni/TiO$_2$ derives from support-induced metal segregation in which Cu is selectively enriched at the catalyst surface, while Ni is enriched at the TiO$_2$ interface. These results demonstrate that Cu—Ni/TiO$_2$ catalysts promise to be a catalyst system capable of integrating directly with a combined HMF and FF product stream from biomass processing to realize lower cost production of liquid fuels from biomass.

In accordance with an aspect, a catalyst is disclosed for hydrodeoxygenating (HDO) furfural (FF) and 5-hydroxymethylfurfural (HMF) to methylated furans, the catalyst comprising: copper-nickel (Cu—Ni) particles supported on titanium dioxide (TiO$_2$), and wherein the copper-nickel particles form core-shell structures in which copper (Cu) is enriched at a surface of the catalyst.

In accordance with another aspect, a method is disclosed of synthesizing a catalyst for hydrodeoxygenating furfural (FF) and 5-hydroxymethylfurfural (HMF) to methylated furans, the method comprising: synthesizing monometallic copper (Cu) catalysts and monometallic nickel (Ni) catalysts; mixing the monometallic Cu and Ni catalysts in deionized water (DI-water) to form a bimetallic Cu—Ni catalyst; drying the mixture of the bimetallic Cu—Ni catalyst; calcining the dried mixture of the bimetallic Cu—Ni catalyst; and synthesizing the bimetallic Cu—Ni catalyst onto titanium dioxide (TiO$_2$) to form a Cu—Ni/TiO$_2$ catalyst, and wherein the copper-nickel particles form core-shell structures in which copper (Cu) is enriched at a surface of the catalyst.

In accordance with a further aspect, a method is disclosed for converting biomass into a fuel additive, the method comprising: liquefying the biomass to form a liquor; neutralizing the liquor; precipitating lignin out of the liquor; extracting furfural (FF) and 5-hydroxymethylfurfural (HMF) from the liquor; and hydrodeoxygenating (HDO) the extracted furfurals over a Cu—Ni/TiO$_2$ catalyst.

In accordance with an aspect, neutralizing the liquor comprises: adding calcium dihydroxide (Ca(OH)$_2$), calcium carbonate (CaCO$_3$), or ammonium hydroxide (NH$_4$OH) to the liquor to neutralize the acidic moieties and precipitate iron hydroxide ions and a portion of lignin.

In accordance with an aspect, the method further comprises extracting furfural (FF) and 5-hydroxymethylfurfural (HMF) from the liquor using an organic solvent treated with Ca(OH)$_2$.

In accordance with an aspect, the organic solvent contains one or more of methanol, ethanol, butanol, isopropyl alcohol, butanediol, pentanediol, toluene, dioxane, methyl-tetrahydrofuran (MTHF), tetrahydrofuran, hexane, decane, nonane, and methyl-isobutylketone (MIBK).

BRIEF DESCRIPTION OF THE DRAWINGS

FIGS. 2(a)-2(h) illustrate XPS spectra of monometallic and bimetallic catalysts in the Cu 2p3/2 energy window for (a) Cu/TiO$_2$, (b)Cu—Ni/TiO$_2$, (c) Cu/Al$_2$O$_3$, and (d) Cu—Ni/Al$_2$O$_3$, and in the Ni 2p3/2 energy window for (e) Ni/TiO$_2$, (f)Cu—Ni/TiO$_2$, (g) Ni/Al$_2$O$_3$, and (h)Cu—Ni/Al$_2$O$_3$. Metallic peaks (Cu$^0$ & Ni$^0$) represented with blue colour and metal oxide peaks (CuO & NiO) peaks represented with green colour. Orange colour represents Ni(OH)x peak.

FIG. 10 is a schematic diagram of the proposed operating states of Cu—Ni bimetallic catalysts on Al$_2$O$_3$ and TiO$_2$. For Cu—Ni/Al$_2$O$_3$ significant exposure of extended Ni domains drive efficient ring hydrogenation to form THFOL, whereas the segregated structure of Cu—Ni on TiO$_2$ facilitate MF formation. $E_{INT}$: Energy of interaction between metal (either Ni or Cu) and support (Al$_2$O$_3$ and TiO$_2$).

FIG. 13 is a table (Table 1) illustrating physicochemical properties of monometallic Cu, Ni and bimetallic Cu—Ni catalysts supported on $Al_2O_3$ and $TiO_2$.

FIG. 22 is a table (Table 2) illustrating hydrodeoxygenation of FF to methyl furan over Ni & Cu-supported over γ-$Al_2O_3$ and $TiO_2$ (P25)

FIG. 23 is a table (Table 3) illustrating activity of bimetallic Ni—Cu/γ-$Al_2O_3$ catalysts to FF hydrogenation compared to Ni—Cu/$TiO_2$ FIG. 24 is a table (Table 4) illustrating effect of temperature on FF hydrogenation over Ni/γ-$Al_2O_3$.

FIG. 37 illustrates XPS depth profiling of Cu(5%)-Ni(3%)/$Al_2O_3$ catalyst. Data derived by Argon sputtering at different time intervals such as 0, 1, 5, 10, 30 and 60 min.

FIG. 42 is a table (Table 5) illustrating XPS Binding energy values derived from 2p3/2 peaks of $Cu^0$ and $Ni^0$ for catalysts of various composition and support. Surface metal-to-metal oxide ratios were calculated from area under the curves of 2p3/2 peaks of Cu and Ni peaks.

FIG. 43 is a table (Table 6) illustrating hydrogen pressure effect on FF hydrogenation over Cu(5%)-Ni(0.5%)/$TiO_2$ catalyst. Reaction Conditions: FF=1 g, catalyst=0.3 g, solvent (1,4 dioxane)=25 ml, reaction time=8 h, reaction temperature=200° C.

DETAILED DESCRIPTION

Figures 1A, 1B, 1C, 1D, 1E, 1F, 1G, 1H:
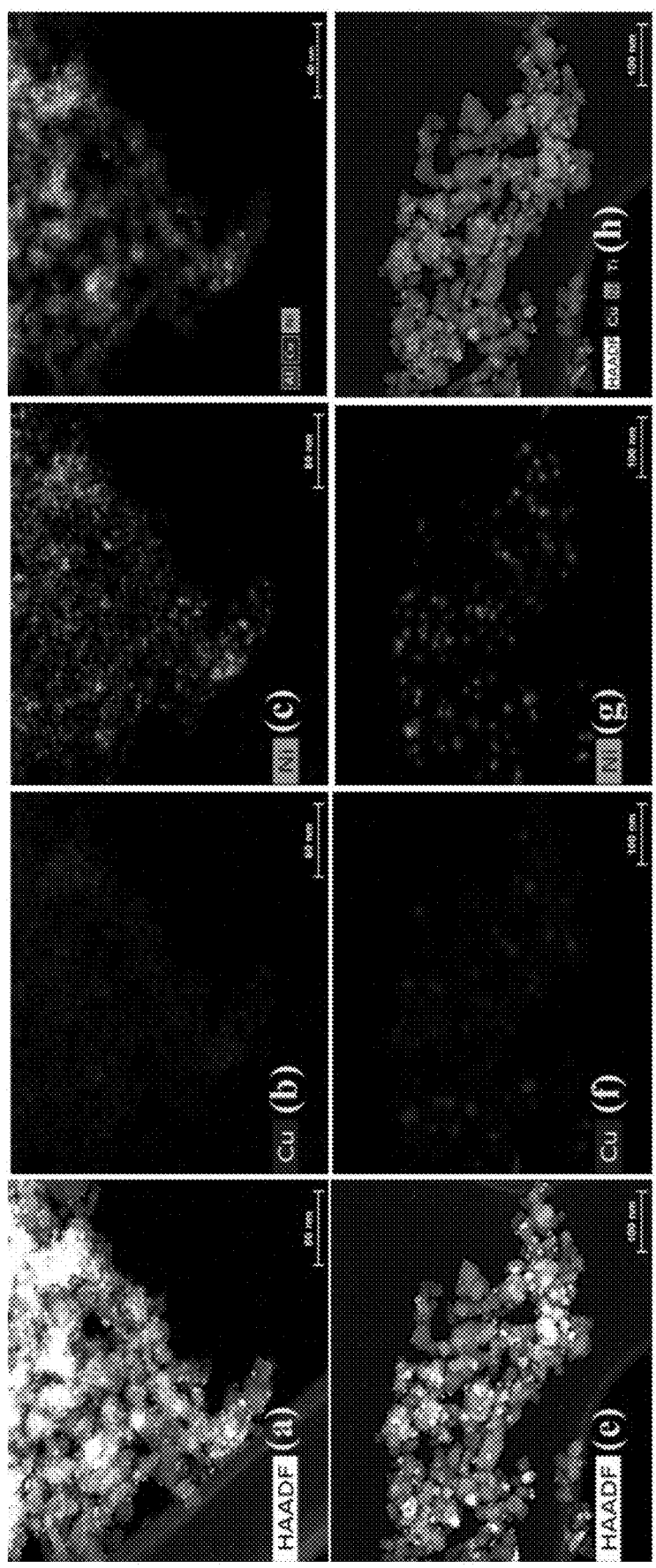
FIGS. 1(a)-1(h) are (a) representative STEM image of the Cu—Ni/Al$_2$O$_3$ catalyst and associated (b) Cu, (c) Ni, and (d) overlayed Cu/Ni/Al elemental mapping. (e) Representative STEM image of the Cu—Ni/TiO$_2$ catalyst and associated (f) Cu, (g) Ni, and (h) overlayed Cu/Ni/Ti elemental mapping.

Support Induced Control of Surface Composition in Cu—Ni/$TiO_2$ Catalysts Enables High Yield Co-Conversion of HMF and Furfural to Methylated Furans In accordance with an exemplary embodiment, a system and method are disclosed for catalyst and process for simultaneous conversion of Hydroxymethyl furfural and furfural to methylated furans, which can demonstrate approximately 90% yields, high reactivity, good stability, and re-generatable behaviour for $TiO_2$ supported Cu—Ni bimetallic catalysts in individual and co-processing of FF and HMF to MF and DMF, respectively. In some embodiments, Cu—Ni bimetallic catalysts can comprise Cu—Ni particles that are between between 2.5 wt %, 5 wt %, 10 wt %, 15 wt %, to 20 wt % Cu or any combination thereof and are between 0.5 wt %, 1.5 wt %, 3 wt %, 5 wt %, 10 wt %, 15 wt %, to 20 wt % Ni or any combination thereof. In some embodiments, Cu—Ni particles can be 2.5 wt % Cu-0.5 wt % Ni, 2.5 wt % Cu-1.5 wt % Ni, 5 wt % Cu-3 wt % Ni, 5 wt % Cu-5 wt % Ni, 10 wt % Cu-5 wt % Ni, 10 wt % Cu-10 wt % Ni, 15 wt % Cu-5 wt % Ni, 15 wt % Cu-10 wt % Ni, 15 wt % Cu-15 wt % Ni, 20 wt % Cu-15 wt % Ni, or 20 wt % Cu-20 wt % Ni.

Detailed characterization and reactivity comparison of monometallic Cu and Ni and bimetallic Cu—Ni supported on $TiO_2$ and $Al_2O_3$ demonstrate that for Cu—Ni/$TiO_2$, core-shell structures form in which Cu is enriched at the catalyst surface. It is proposed that this structure forms due to strong and preferential interactions between Ni and $TiO_2$ that reduce the concentration of Ni at the catalyst surface, thereby allowing Ni to promote Cu reactivity without compromising selectivity. In accordance with an exemplary embodiment, the use of metal-support interactions to control the exposed metal composition in bimetallic catalysts should be useful for enhancing selectivity, reactivity and stability in variety of catalytic processes.

Materials and Methods

Synthesis of Monometallic Cu and Ni Catalysts

In a typical synthesis, copper (II) nitrate trihydrate ($Cu(NO_3)_2 3H_2O$, Aldrich, purity 99%, CAS: 10031-43-3, New Jersey, USA) was dissolved in 50 mL deionized (DI)-water and added to 5 g of 6-$Al_2O_3$(Inframat Advanced Materials, Catalogue no: 26R-0804UPG, Manchester CT 06042, USA) or $TiO_2$ (P25, NIPPON AEROSIL Co., LTD, Evonik, Degussa GmbH, Batch No. 4161060398) contained in a round bottom flask to obtain a 10 wt % loading of Cu. In accordance with an exemplary embodiment, the solution was mixed and dried at 80° C. in a rotary evaporator. Supported Ni catalysts were prepared similarly to Cu catalysts, where nickel (II) nitrate hexahydrate ($Ni(NO_3)_2 6H_2O$, Aldrich, purity 99.99%, Louis, Mo. 63103, USA) was used as a precursor in desired quantities to achieve 10 wt % loadings on $TiO_2$ and θ-$Al_2O_3$. The resulting solids were dried at 100° C. for 12 hours in an oven and calcined at 450° C. for 5 hours. Prior to reactivity experiments, catalysts were reduced by a pure $H_2$ flow rate of 50 mL $min^{-1}$ at 450° C. for 3 hours and cooled to 25° C. under the same environment.

Synthesis of Bimetallic Cu—Ni Catalysts

Required amounts of Ni and Cu precursors to achieve 5 wt % loadings of each metal were mixed simultaneously in 50 mL of DI-water and added to 5 g of $TiO_2$ or $\theta$-$Al_2O_3$ in a round bottom flask. These materials were then mixed and dried at 80° C. in a rotary evaporator. The solid was collected and dried at 100° C. for 12 hours in an oven followed by calcining at 450° C. for 5 hours. Prior to reactivity experiments, catalysts were reduced by pure $H_2$ at a flow rate of 50 mL min$^{-1}$ at 450° C. for 3 hours and cooled to 25° C. under the same environment.

Catalyst Characterization Techniques

X-Ray Diffraction (XRD):

XRD spectra of reduced catalysts were recorded in the 2θ range of 20° to 90° using an X'pert Pro PANalytical diffractometer equipped with a Nickel filtered Cu-Kα radiation source.

Surface Area:

The total accessible surface area ($S_{BET}$) of the catalysts was measured by $N_2$ physisorption using a Micromeritics ASAP 2020 instrument.

Scanning Transmission Electrom Microscopy (STEM):

STEM imaging was performed at 300 kV accelerating voltage on an FEI Titan Themis 300 instrument fitted with X-FEG electron source, 3 lens condenser system, and S-Twin objective lens. STEM images were recorded with a Fischione Instruments Inc. M3000 High Angle Annular Dark Field (HAADF) Detector at a probe current of 0.2 nA, frame size of 2048×2048, dwell time of 15 sec/pixel, camera length of 195 mm, and convergence angle of 10 mrad. Elemental X-ray microanalysis and mapping were performed utilizing FEI Super-X EDS system with four symmetrically positioned SDD detectors of 30 mm$^2$ each resulting in effective collection angle of 0.7 srad. Elemental maps were collected in STEM mode with beam current of 0.4 to 0.25 nA with 512×512 pixel frame, dwell time of 30 μs, and acquisition time of up to 10 mins. Specimens prepared from suspension in distilled water were deposited on copper grids coated with a lacey carbon. Average metal particle sizes were measured based on the diameter of 100 particles from corresponding TEM images each catalyst.

X-Ray Photoelectron Spectroscopy (XPS):

XPS characterization was carried out using a Kratos AXIS ULTRADLD XPS system equipped with an Al Kα monochromated X-ray source and a 165-mm mean radius electron energy hemispherical analyzer. Vacuum pressure was kept below 3×10$^{-9}$ torr during analysis. Binding energy calibrations were done with reference to the carbon is peak by adjusting spectra to 284.8 eV. Depth profiling experiments were conducted by Argon sputtering samples for 0, 1, 5, 10, 30 and 60 min with beam voltage of 4 kV, current of 2.35 A, spot size of 3×3 mm$^2$ and vacuum pressure of 3×10-9 Torr during acquisition. XPS Peak fitting for Cu and Ni components was optimized for each support, and parameters of the fit were kept constant. A FWHM of 2 eV (2.15 eV) and a Gaussian/Lorenzian line shape ratio of 30% (60%) was used for all Cu and Ni peak fitting on $Al_2O_3$($TiO_2$). Surface composition of bimetallic Cu/Ni catalysts was calculated using sensitivity factors of 5.321 and 4.044 for Cu and Ni, respectively.

Temperature Programmed Reduction (TPR):

TPR experiments were carried out on a Micromeritics AutoChem 2920 instrument. In each experiment, 0.1 g of catalyst was placed in a quartz tube and treated with pure Ar flowing at 30 mL min$^{-1}$ and 150° C. for 1 hour. A gas mixture of $H_2$ (10%)—Ar (90%) was passed through the quartz reactor at 25° C. for 1 hour with a 50 mL min$^{-1}$ flow rate. The temperature was raised to 800° C. at a linear heating rate of 5° C. min$^{-1}$. A standard CuO powder was used to calibrate $H_2$ consumption.

Reactivity Measurements:

Prior to each reaction, Ni, Cu, and Cu—Ni catalysts were reduced at 450° C. for 3 hours. Without exposure to air, 0.3 g of reduced catalysts were transferred into a 100-mL stainless-steel Parr micro bench-top reactor containing 1 g of FF (Sigma Aldrich, 99.9% pure) with 25 ml of either isopropyl alcohol (Fischer Chemical, HPLC grade) or 1,4 dioxane (Fisher Chemicals, HPLC Grade) as a solvent. The reactor was initially flushed with $H_2$ and then pressurized under pure $H_2$ environments. Next, the reactor temperature was raised to 25° C. to 240° C., and the reaction was conducted for 1-8 hours. An identical protocol was used for the HMF and FF/HMF co-processing reactions, except in HMF conversion reactions, 0.5 g of HMF was used as a reactant and for FF/HMF co-processing reactions, 0.5 g of FF and 0.25 g of HMF were used.

Product Analysis:

Liquid products were analyzed by gas chromatography (Agilent Technologies 7890A; column: DB-WAX Ultra Inert, 30 m long×0.320 mm internal diameter×0.5 micron) via FID according to the following program: hold for 1 min at 30° C., increase from 30 to 100° C. at a ramp rate of 10° C. min-, 2 min hold at 100° C., increase from 100 to 250° C. at a ramp rate of 25° C./min, 0 min hold, increase from 250 to 325° C. at a ramp rate of 25° C. min$^{-1}$, and 1 min hold at 325° C. Mass yields of the final product were quantified by using calibration curves of standard samples in the gas chromatograph. Mass balances accounting for >95% of the carbon content were obtained in all experiments. Reactant conversion and product yield were calculated as follows:

$$HMF \text{ (or) } FF \text{ conversion } \% = \left(1 - \frac{\text{moles of unreacted } FF}{\text{moles of } FF \text{ before reaction}}\right) \times 100$$

$$Yields = \frac{\text{moles of the product prodcued}}{\text{moles of } HMF \text{ (or) } FF \text{ before reaction}}$$

Catalyst Recyclability

In accordance with an exemplary embodiment, 0.3 g of freshly reduced catalysts were transferred into a 100 mL stainless-steel Parr reactor containing 1 g of FF and 25 mL of 1,4-dioxane. The reactor was pressurized with $H_2$ to 25 bar, and the reaction was conducted for 2 hours at 200° C. The reactor was cooled by quickly lowering it into a room temperature water bath (25° C.) and then depressurized. The catalyst was separated by filtration, dried at 100° C. for 3 hours, and then reused in four recycle experiments without reduction or re-activation. Regeneration was executed via calcination at 450° C. for 5 hours followed by reduction with pure $H_2$ at 450° C. for 3 hours.

Results

Catalyst Characterization

Figures 14A, 14B:
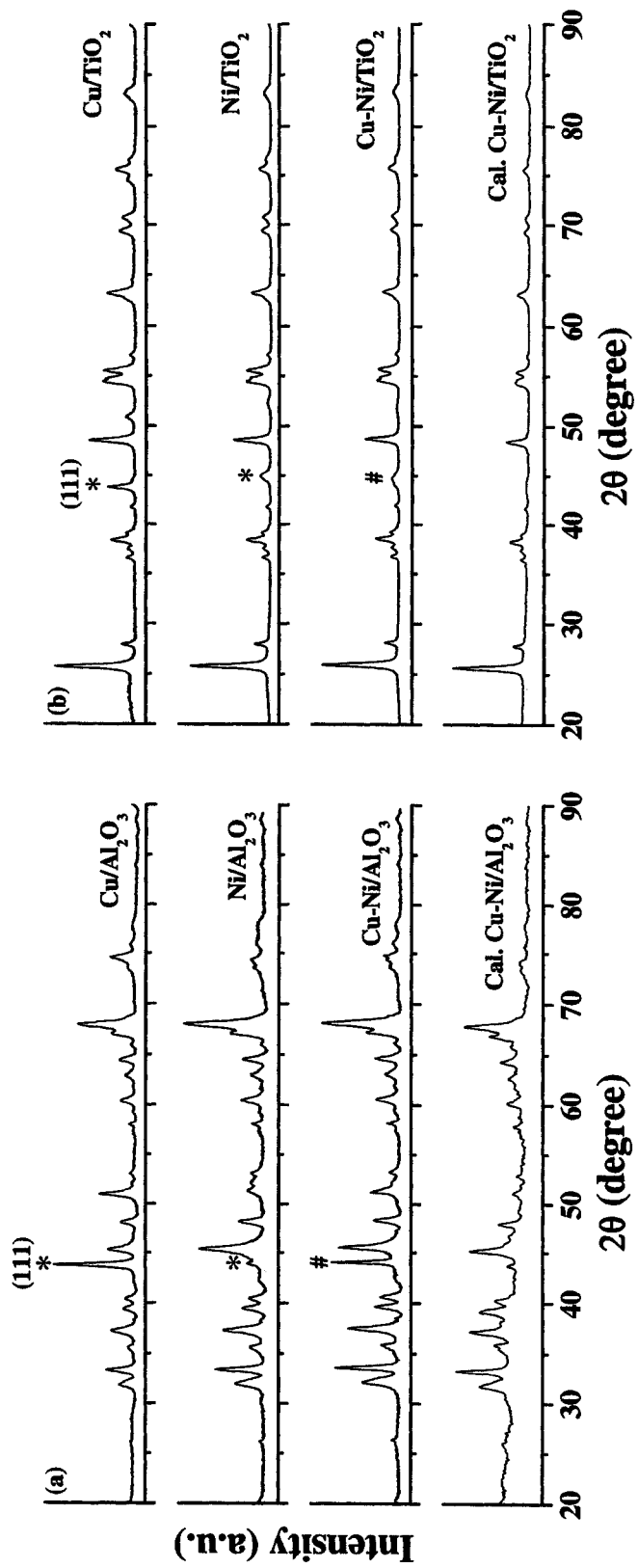
FIGS. 14(a) and 14(b) are illustrations of XRD spectra of mono Cu, Ni and bimetallic Cu—Ni on $TiO_2$ and $Al_2O_3$ catalysts

To explore the influence of support, and the formation of bimetallic particles on HDO performance, monometallic Cu (10% weight loading) and Ni (10% weight loading) catalysts and bimetallic Cu—Ni catalysts (5% Cu-5% Ni weight loading) on $TiO_2$ and $\theta$-$Al_2O_3$ were synthesized via an impregnation approach. XRD spectra of reduced monometallic (Cu and Ni) and bimetallic (Cu—Ni) catalysts are shown in FIG. 14. Reduced monometallic Cu catalysts showed distinct peaks at 43.3° and 50.4° that correspond to the (111) and (200) reflections of metallic Cu, respectively. The reduced monometallic Ni catalysts exhibited clear peaks associated with the (111) reflection of metallic Ni at 44.90, although in the case of the Ni/Al$_2$O$_3$ catalyst this peak overlapped with Al$_2$O$_3$ reflections. The Cu—Ni/Al$_2$O$_3$ catalyst exhibited a diffraction peak at 43.90, and the Cu—Ni/TiO$_2$ catalyst exhibited a diffraction peak at 44.10 and a shoulder at 44.60. The existence of diffraction peaks between the Cu (111) and Ni (111) reflections for the bimetallic catalysts are evidence of the formation of Cu—Ni alloy phases. However, in accordance with an exemplary embodiment, using these peak positions to draw conclusions about the nature of the Cu—Ni alloy was refrained, as the diffraction peaks are predominantly derived from the largest particles in each catalyst and are not representative of the composition of all particles in each sample.

Figures 15A, 15B, 15C, 15D:
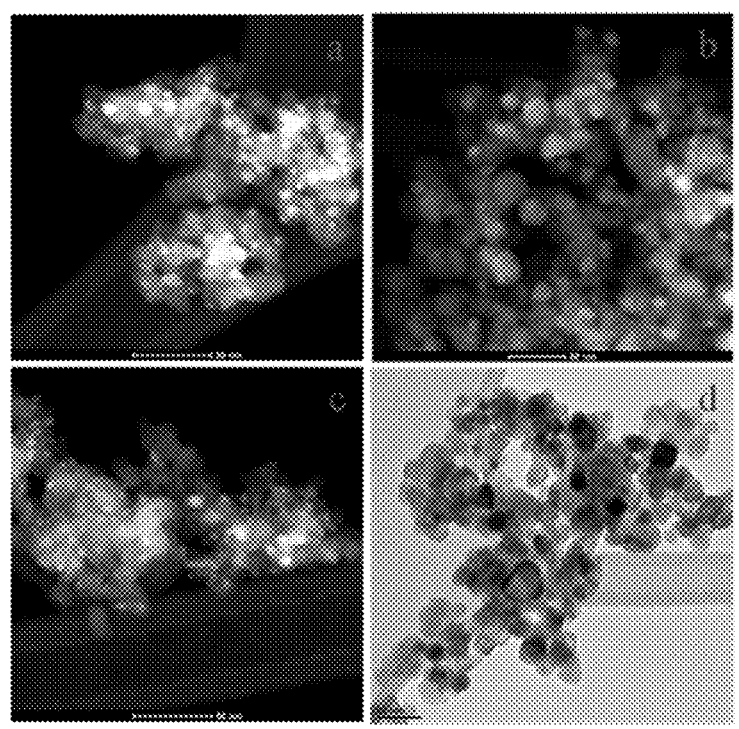
FIGS. 15(a)-(d) is an illustration of particle size distributions from TEM images of mono (a) $Ni/Al_2O_3$, (b) $Ni/TiO_2$, (c) $Cu/Al_2O_3$, and (d) $Cu/TiO_2$ catalysts.
Figures 1, 16:
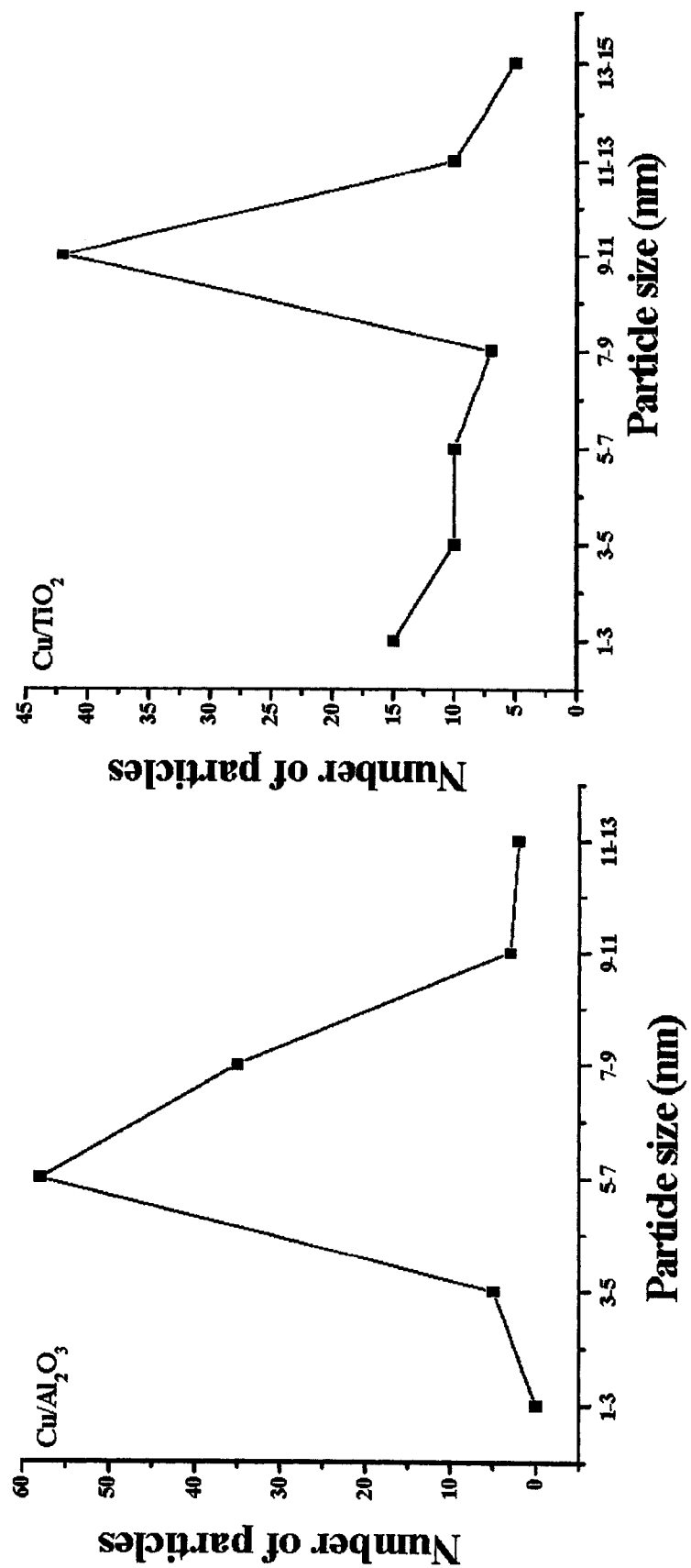
FIG. 16 is an illustration of particle size distributions from TEM images of mono Cu, Ni and bimetallic Cu—Ni on $TiO_2$ and $Al_2O_3$ catalysts.

Representative TEM images of the monometallic and bimetallic catalysts are shown in FIGS. 1(a), 1(b), and 15, with corresponding particle size distributions shown FIG. 16 and average particle sizes reported in Table 1 (FIG. 13). The average metallic particle diameter in all catalysts was relatively consistent, with values between 4.9 and 9.9 nm. It was observed that for a given metal composition, the Al$_2$O$_3$ supported catalysts exhibited an approximately 1 nm to 2 nm smaller average particle diameter compared to the TiO$_2$ supported catalysts. In accordance with an exemplary embodiment, this could be due to the approximately 20 m$^2$/g greater total surface area of the Al$_2$O$_3$ supported catalysts compared to the TiO$_2$ supported catalysts, see Table 1 (FIG. 13). From the TEM analysis, it was concluded that the active metal particle sizes in all catalysts are relatively consistent and significant differences in catalyst performance as a function of support for a given metal composition are not expected to be derived from particle size effects. Elemental mapping executed for the Cu—Ni/TiO$_2$ and Cu—Ni/Al$_2$O$_3$ catalysts shown in FIGS. 2(b)-2(d) and 2(f)-2(h) demonstrated that Cu and Ni signals co-existed for all observed metal particles. This is consistent with the XRD results, providing evidence that bimetallic Cu—Ni particles formed on both Al$_2$O$_3$ and TiO$_2$.

XPS was used to characterize the oxidation state and surface composition of the monometallic and bimetallic catalysts by analyzing the Cu and Ni 2p3/2 peaks. Because these experiments were performed ex-situ, the exposure to air when catalysts were transferred from the reduction reactor to the XPS chamber caused partial metal oxidation. FIG. 2(a)-2(d) shows the Cu 2p3/2 spectra for pre-reduced monometallic Cu and bimetallic Cu—Ni catalysts on Al$_2$O$_3$ and TiO$_2$. All reduced Cu containing catalysts show signatures of Cu$^0$ with binding energies of 932.1-932.4 eV and Cu$^{2+}$ with binding energies of 933.7-934.0, and the associated shake-up satellite peak at approximately 943 eV, consistent with literature. In accordance with an exemplary embodiment, it was noted that the Cu$^{1+}$ peak was not included in this analysis due to overlap with the position of the Cu$^0$ peak, although this is not expected to significantly influence any conclusions. Comparing the monometallic Cu catalysts on TiO$_2$ and Al$_2$O$_3$, it was observed that the relative fraction of Cu$^0$ species, with respect to Cu$^{2+}$, is lower on TiO$_2$ (52.2% for TiO$_2$ versus 62.4% for Al$_2$O$_3$, Table 1) and that the binding energy of Cu$^0$ is shifted down from 932.4 eV for TiO$_2$ to 932.1 eV for Al$_2$O$_3$. The increased fraction of oxidized Cu$^{2+}$ and the shift in energy of the Cu$^0$ peak on the TiO$_2$ support were likely caused by Cu$^0$ catalyzed reduction of TiO$_2$, with subsequent formation of CuO$_x$ species and charge transfer from Cu$^0$ to CuO$_x$ or TiO$_2$. For Cu—Ni/TiO$_2$, the relative fraction of Cu$^0$ compared to Cu$^{2+}$ increased to values consistent with those observed for Cu/Al$_2$O$_3$ and Cu—Ni/Al$_2$O$_3$, and the binding energy of the Cu$^0$ species also shifted down slightly, suggesting weaker interactions between Cu and TiO$_2$ in Cu—Ni/TiO$_2$ compared to Cu/TiO$_2$.

In FIGS. 2(e)-2(h), the Ni 2p3/2 XPS spectra is shown for monometallic Ni and bimetallic Cu—Ni supported on Al$_2$O$_3$ and TiO$_2$. All supported Ni catalysts showed three peaks between 852.2 to 853.0 eV, 854.5 to 854.8 eV, and 856.2 to 856.6 eV that are assigned to metallic Ni$^0$, NiO, and Ni(OH)$_2$, respectively. Binding energies for the Ni$^0$ 2p3/2 peaks were in the order Ni—Cu/Al$_2$O$_3$≈Ni/Al$_2$O$_3$>Ni/TiO$_2$≈Ni—Cu/TiO$_2$, with the well-known strong interactions between Ni and TiO$_2$ driving charge transfer from Ti$^{+3}$ to Ni d-states. The shift in binding energy of the Ni$^0$ 2p3/2 peak when comparing the monometallic Ni catalysts on Al$_2$O$_3$ and TiO$_2$ was more significant than that observed for the Cu$^0$ 2p3/2 peak in the monometallic Cu catalysts (0.7 eV versus 0.3 eV), demonstrating stronger interactions and increased charge transfer at the Ni/TiO$_2$ interface.

Figure 17:
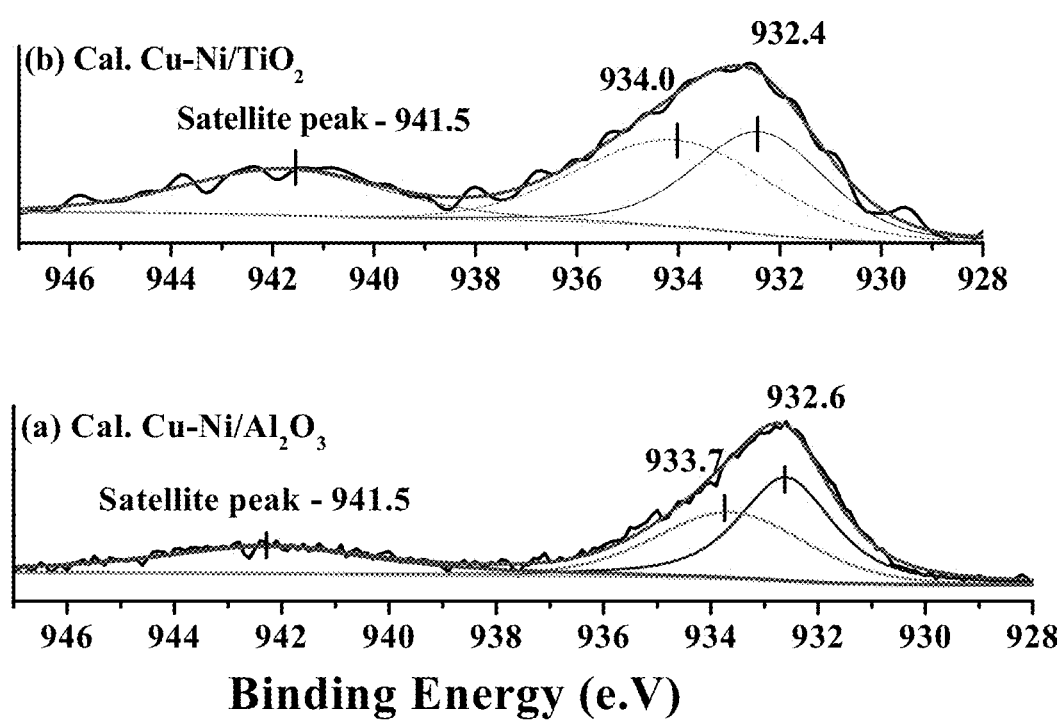
FIG. 17 is an illustration of XPS of calcined Cu(2p3/2) peaks of bimetallic catalysts
Figure 18:
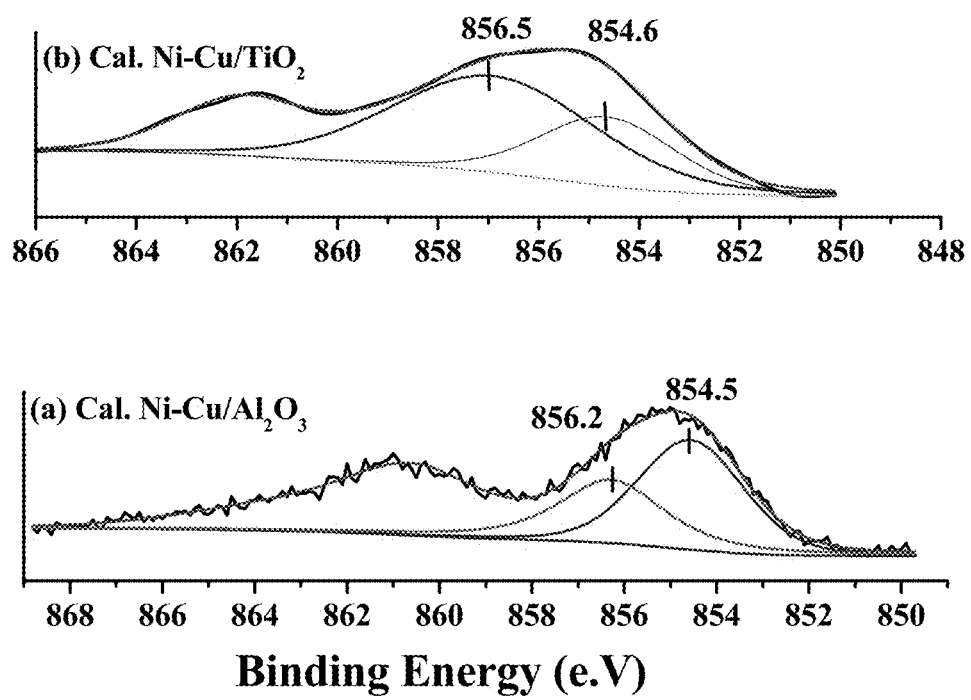
FIG. 18 is an illustration of XPS of calcined Ni(2p3/2) peaks of bimetallic samples

In accordance with an exemplary embodiment, the Cu/Ni surface composition ratio was calculated for bimetallic catalysts after reduction and calcination by summing all contributions to the Cu and Ni 2p3/2 spectra and correction for XPS sensitivity factors. For the Al$_2$O$_3$ supported bimetallic catalyst, an almost equal Cu/Ni surface composition ratio of 48.7/51.3 (Table 1) was observed for the reduced catalyst, consistent with the equal weight loadings of Cu and Ni, the miscibility of Cu and Ni, and their expected non-specific interactions with Al$_2$O$_3$. Interestingly, the surface composition for the TiO$_2$ supported bimetallic catalyst was significantly enriched in Cu, with a Cu/Ni ratio of 82.4/17.6. As shown in Table 1 and FIGS. 17 and 18, the bimetallic catalyst surface compositions were almost identical after reduction and calcination. The surface enrichment of Cu and weaker Cu—TiO$_2$ interactions observed by XPS in the Cu—Ni/TiO$_2$ catalyst compared to monometallic Cu/TiO$_2$, combined with the observed and well-known stronger interactions between Ni and TiO$_2$ compared to Cu and TiO$_2$, suggest that preferential interactions between Ni and TiO$_2$ drive formation of core-shell type structures on Cu—Ni/TiO$_2$ catalysts where Cu is preferentially exposed at the surface.

Figure 3:
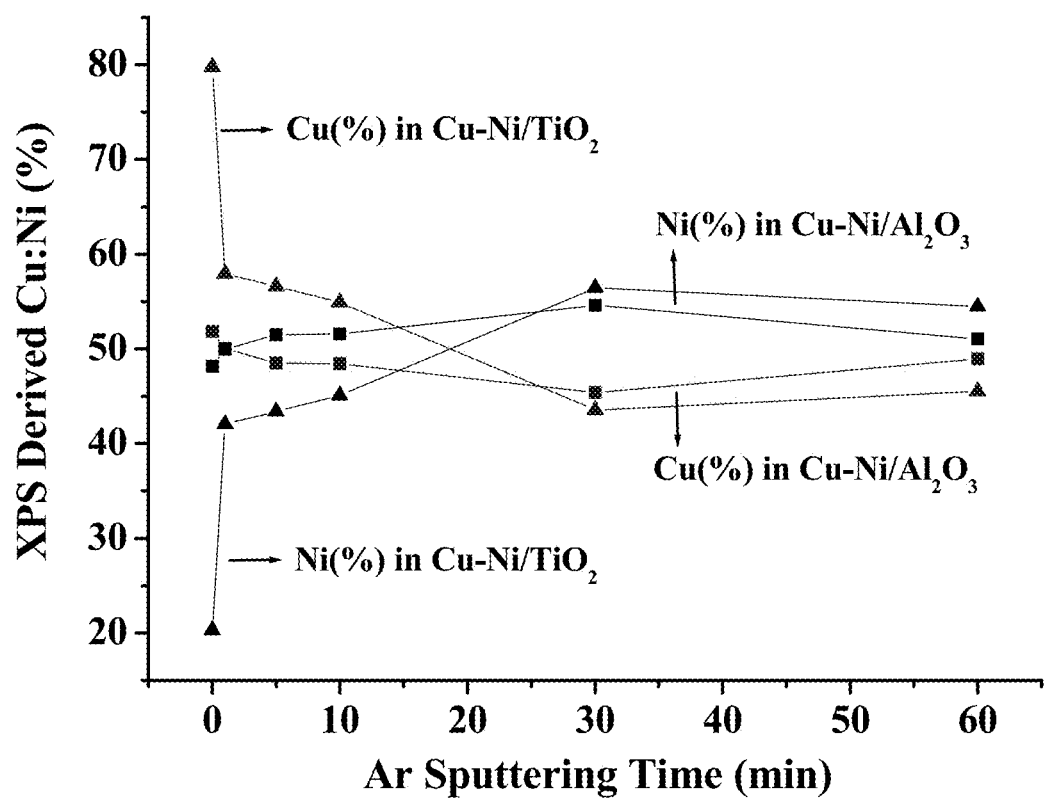
FIG. 3 illustrates relative Cu:Ni surface concentration (%) for pre-reduced Cu—Ni/TiO$_2$ and Cu—Ni/Al$_2$O$_3$ catalysts measured by XPS during depth profiling experiments as a function or Ar sputtering time.
Figure 4:
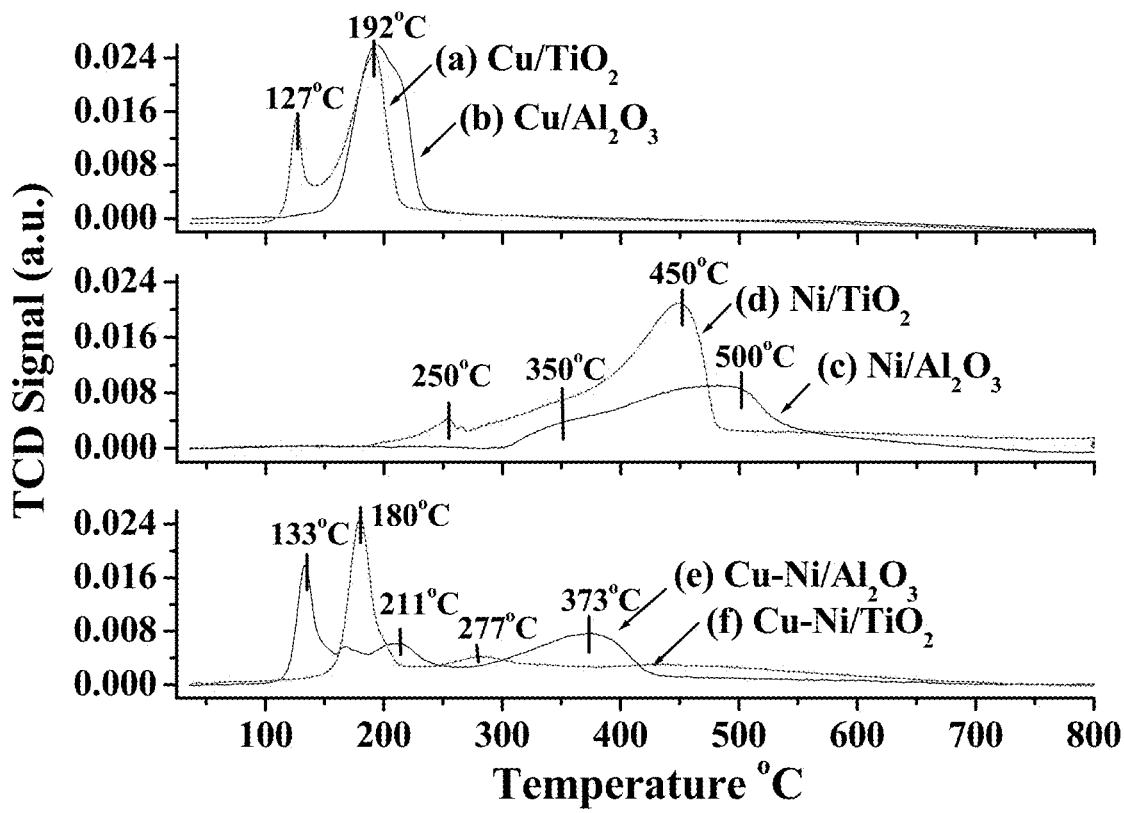
FIG. 4 illustrates H$_2$-TPR spectra for (a) Cu/TiO$_2$, (b) Cu/Al$_2$O$_3$, (c) Ni/TiO$_2$, (d) Ni/Al$_2$O$_3$, (e) Cu—Ni/Al$_2$O$_3$ and (f), Cu—Ni/TiO$_2$.
Figure 5:
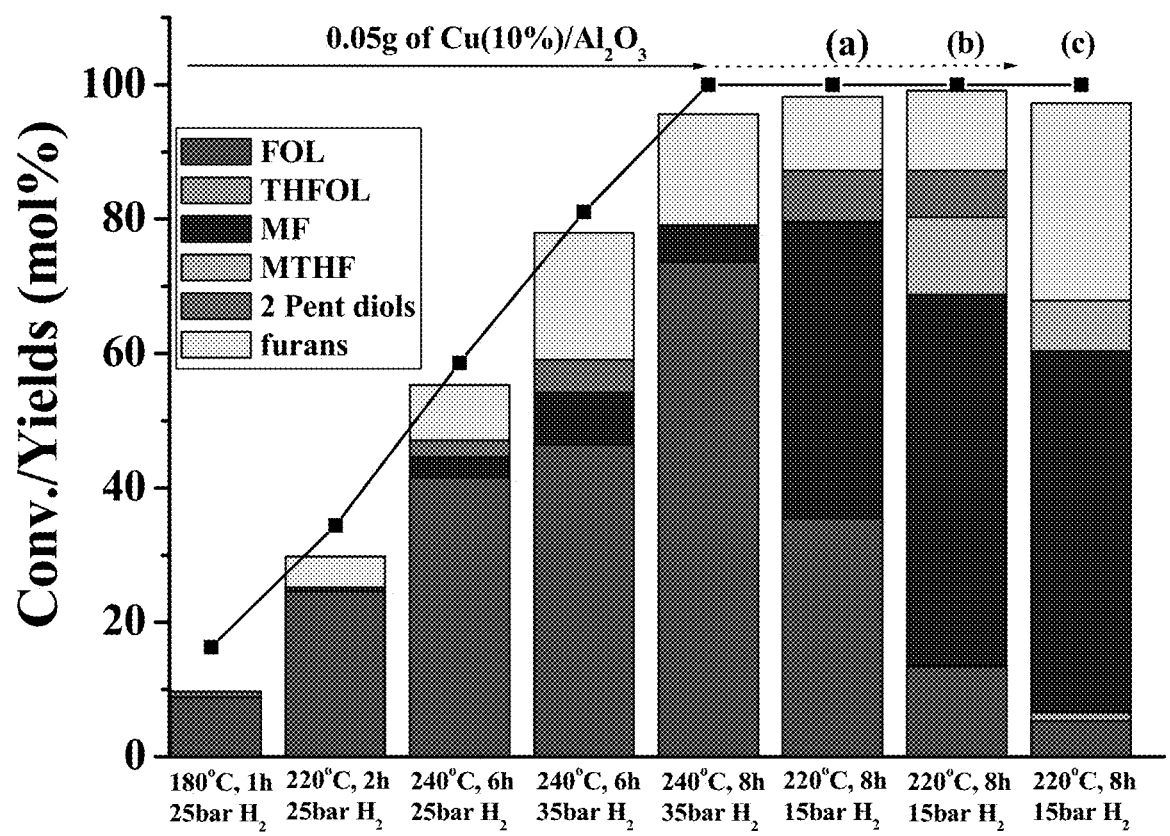
FIG. 5 illustrates FF conversion and product yields for Cu/A$_2$O$_3$ catalysts for the reaction conditions shown along the x-axis at four catalyst loadings. All reactions except those noted by a, b, and c were executed at a FF loading of 1 g, 25 mL IPA solvent, and Cu(10 wt %)/Al$_2$O$_3$ catalyst loading of 0.05 g. The catalyst loadings for the other three were (a) 0.15 g for Cu(10 wt %)/Al$_2$O$_3$], (b) 0.3 g for Cu(10 wt %)/Al$_2$O$_3$, and (c) 0.3 g for Cu(25 wt %)/Al$_2$O$_3$.
Figure 19:
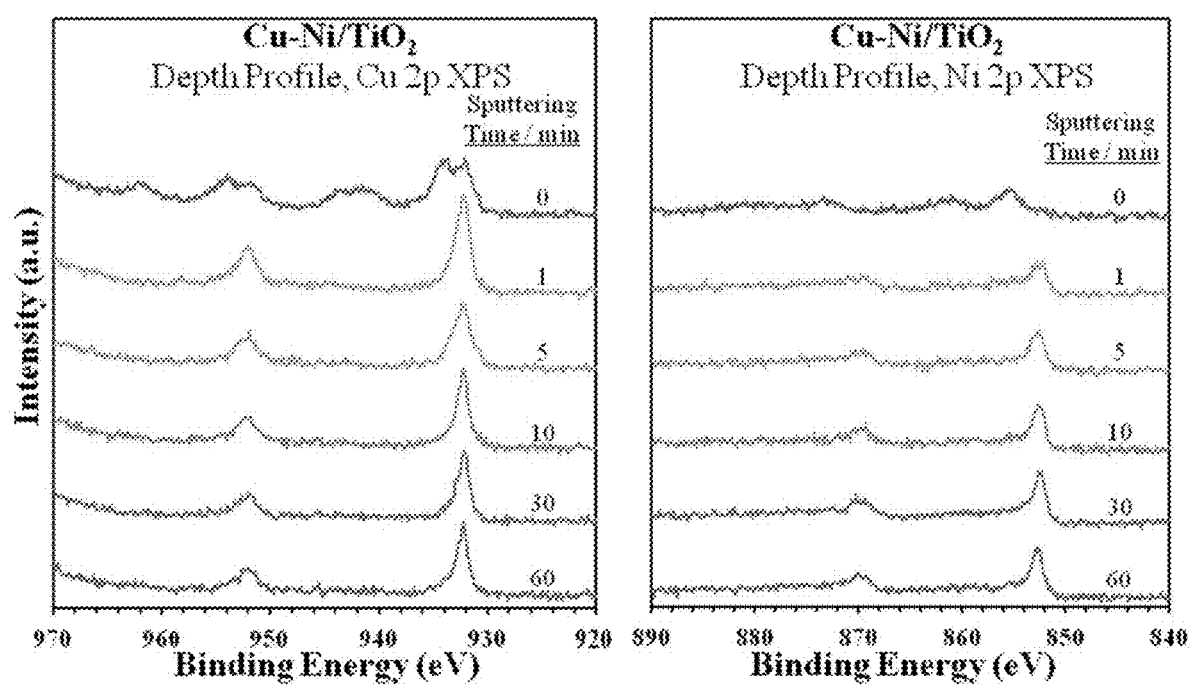
FIG. 19 is an illustration of XPS depth profiling of Cu—Ni/$TiO_2$ catalyst. Cu—Ni/$TiO_2$ data derived by Argon sputtering at different time intervals such as 0, 1, 5, 10, 30 and 60 min.
Figure 20:
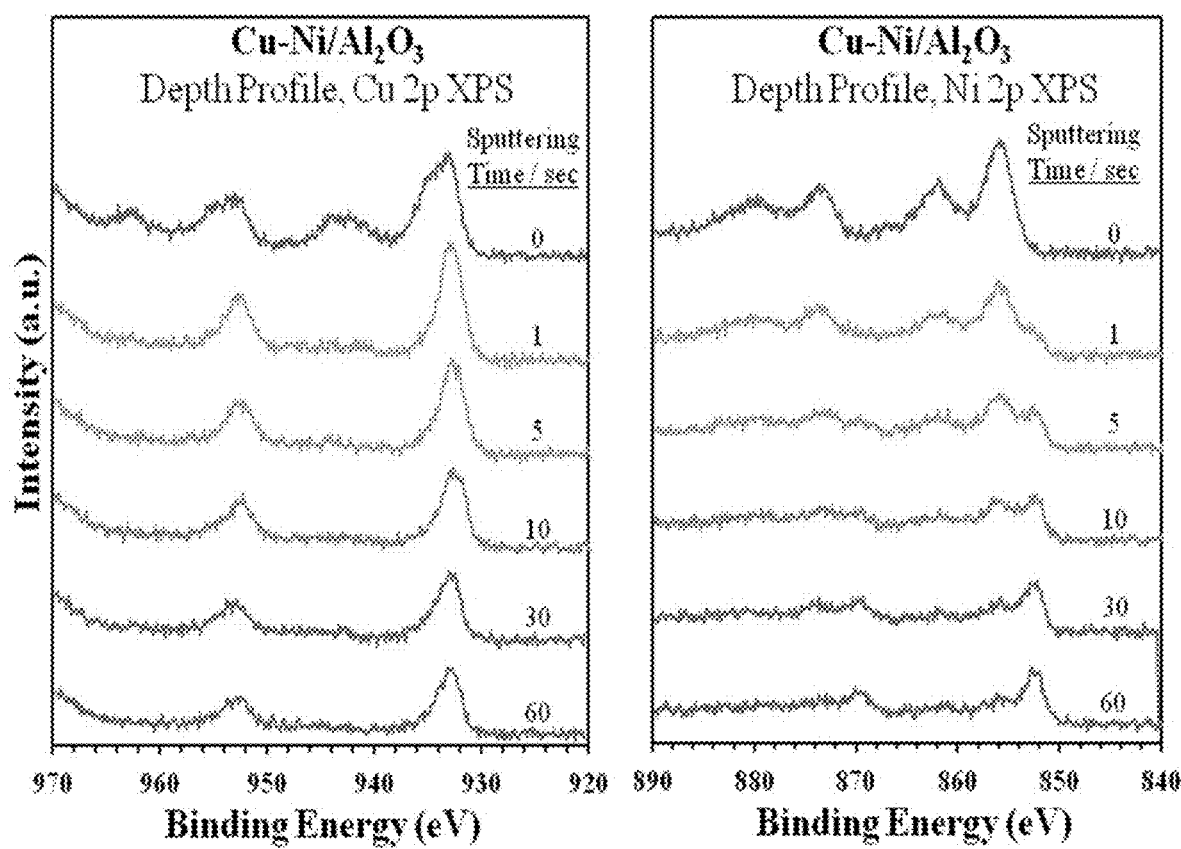
FIG. 20 is an illustration of XPS depth profiling of Cu—Ni/$Al_2O_3$ catalyst. Cu—Ni/$Al_2O_3$ data derived by Argon sputtering at different time intervals such as 0, 1, 5, 10, 30 and 60 min.

To further substantiate the conclusion that TiO$_2$ induced the formation of core-shell type structures for the bimetallic catalysts, depth profiling XPS experiments were conducted for reduced Cu—Ni/TiO$_2$ and Cu—Ni/Al$_2$O$_3$ catalysts by using Ar ion bombardment, FIGS. 3, 19, and 20. For the Cu—Ni/Al$_2$O$_3$ catalyst an almost constant 50%-50% composition ratio was observed at increasing Ar sputtering times, which suggests an even distribution of Cu and Ni throughout the bimetallic particles. For the Cu—Ni/TiO$_2$ catalyst, the relative Cu composition decreased from 79.1% to 45.5% as the Ar sputtering time was increased. The switch in composition from predominantly Cu to slightly Ni enriched with increasing Ar sputtering time (and thus depth) is direct evidence of core-shell like structure for the TiO$_2$ supported bimetallic catalysts. Because these catalysts are high surface area materials it is difficult to relate Ar sputtering time to sputtering depth, which would provide a quantitative compositional structure of the particles. Regardless of this limitation, contrast between the relative Cu and Ni compositions as a function of Ar sputtering time for the Al$_2$O$_3$ and TiO$_2$ catalysts is strong evidence that TiO$_2$ induced the formation of core-shell structures where the catalytic surface is Cu enriched and the TiO$_2$ interface is Ni enriched.

To corroborate inferences regarding metal-support interactions and Cu surface enrichment in Cu—Ni/TiO$_2$, temperature programmed reduction (TPR) spectra were measured as shown in FIG. 3. The amount of $H_2$ consumption in the TPR experiments was calculated for all samples, showing relatively consistent values between 1.3-1.7 mmol/g catalyst, Table 1, which corresponds to approximately 8% to 10% of the catalyst mass. In accordance with an exemplary embodiment, this was in agreement with the nominal approximately 10% metal weight loading in all samples, suggesting that nominal weight loadings well represent the actual weight loadings and that most Cu and Ni species were reduced in the TPR experiments.

FIGS. 3(a) and 3(b) show that the TPR spectra of $Cu/Al_2O_3$ exhibited a single reduction peak at 191° C., whereas two peaks were observed for $Cu/TiO_2$ at 127 and 192° C. The low temperature reduction peak for $Cu/TiO_2$ is attributed to $CuO_x$ species directly interacting with the $TiO_2$ support, whereas the approximately 190° C. reduction peak is assigned to bulk-like $CuO_x$. In the case of $Ni/Al_2O_3$, FIG. 3(c) shows that two reduction peaks were observed at 350° C. and 500° C. The former is assigned to the reduction of amorphous NiO species, while the latter is assigned to reduction of crystalline NiO. Depending on synthesis procedure and calcination temperature, non-stoichiometric and stoichiometric Ni-aluminates may also form, although these species (TPR peaks>500° C.) were not observed here. The TPR spectra of $Ni/TiO_2$ in FIG. 3(d) showed three peaks at 250° C., 350° C., and 450° C. The peaks at 250° C. and 350° C. are assigned to strongly interacting amorphous and crystalline NiO on $TiO_2$, due to their significant shift down in temperature compared to $Ni/Al_2O_3$, and the peak at 450° C. is assigned to the onset of $TiO_2$ reduction. TPR results from the monometallic catalysts are in agreement with XPS results, providing evidence for significant $TiO_2$ interactions with Cu and Ni and that this interaction is stronger for Ni—$TiO_2$.

For Cu—$Ni/Al_2O_3$, the reduction peaks associated with Cu and Ni in FIG. 3(e) both shifted to lower temperatures, as compared to the monometallic catalysts supported on $Al_2O_3$. This result suggests an intimate interaction between Ni and Cu species, consistent with the TEM and the XPS analyses that showed similar surface concentrations of Cu and Ni. For Cu—$Ni/TiO_2$, the sharp reduction peak observed at 180° C. in FIG. 3(f) was assigned to $CuO_x$ reduction, and the very weak reduction peak at 277° C. was assigned to amorphous NiO reduction. The dominant signature of $CuO_x$ reduction coupled with the lack of peak associated with reduction of $CuO_x$ species that are directly interacting with $TiO_2$ (seen previously at 127° C. for $Cu/TiO_2$) are strong evidence of the core-shell structure for Cu—$Ni/TiO_2$, where Cu is exposed at the surface due to strong Ni—$TiO_2$ interactions.

To summarize catalyst characterization, monometallic Cu and Ni catalysts on $Al_2O_3$ and $TiO_2$ exhibited clear signatures of metal-support charge transfer on $TiO_2$, and the strength of this interaction was greater for Ni compared to Cu. For the bimetallic catalysts, STEM imaging and elemental mapping showed that all metal particles observed on $TiO_2$ and $Al_2O_3$ contained Cu and Ni, demonstrating the formation of bimetallic particles. For Cu—$Ni/Al_2O_3$ it was observed that the bimetallic particles contained a homogeneous mixture of Cu and Ni throughout the particles. However, for Cu—$Ni/TiO_2$ strong Ni—$TiO_2$ interactions induced the formation of core-shell like structures enriched in Cu at the catalytic surface. While it is known that surface segregation in bimetallic catalysts can be driven by reactant adsorption, the use of preferential metal-support interactions to control surface compositions in bimetallic catalysts is much less common.

Catalytic Activity

Hydrogenation of Furfural:

The conversion of FF to MF follows a consecutive reaction pathway with many parallel reactions that can drive formation of undesired products. In addition to catalyst composition, it has been observed that reaction selectivity (and ultimately yields) is sensitive to reaction temperature, time, $H_2$ pressure, and catalyst/reactant loading. In accordance with an exemplary embodiment, reaction conditions of 180° C. to 240° C., 15 to 55 bar $H_2$, and 5 to 30% catalyst/reactant mass loading ratios were screened to identify the conditions at which both Ni and Cu metals produced the highest MF yields shown in FIGS. 5 and 22-24 (Table S1-3). It was identified that at a temperature of 200° C., 25 bar $H_2$ pressure and catalyst/reactant loading of 30%, decarbonylation and ring opening reactions were significantly suppressed and the reactions on all catalysts were mostly by hydrogenation and hydrogenolysis of FF. All subsequent reactions were performed at these conditions. It is also worth noting that for initial catalyst screening, isopropyl alcohol was used as a solvent. However, because of significant solvent conversion, all subsequent reactivity comparisons with 1,4-dioxane as the solvent due to its stability at optimized reaction conditions.

Figure 6:
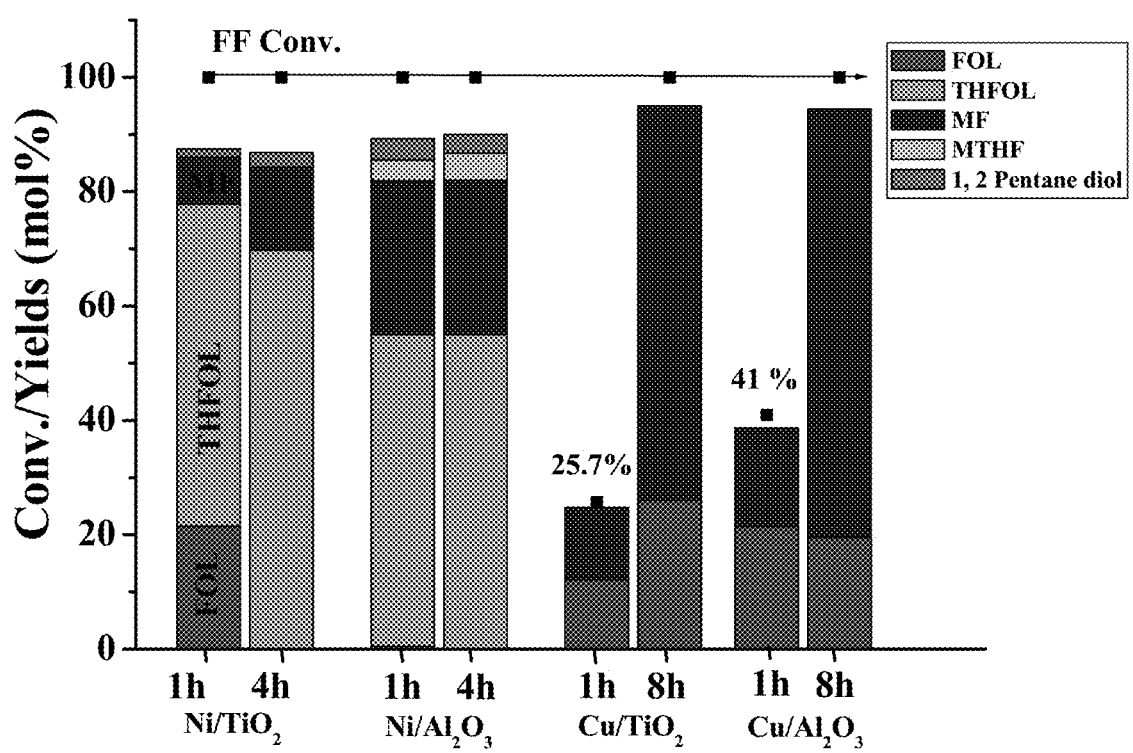
FIG. 6 illustrates FF conversion and product yields over monometallic Ni and Cu supported on Al$_2$O$_3$ and TiO$_2$ catalysts at different reaction times. All reactions were run with FF loading of 1 g, catalyst loading of 0.3 g, 25 mL of 1,4 Dioxane as solvent, temperature of 200° C., and H$_2$ pressure of 25 bar.

The conversion of FF and yield of various products over monometallic Ni and Cu on $Al_2O_3$ and $TiO_2$ catalysts at 1 and 8 (4 for Ni) hour reaction times is shown in FIG. 6. Generally, monometallic Cu catalysts were selective for MF production, while Ni catalysts were selective for production of THFOL. The Ni catalysts were significantly more reactive than Cu catalysts, as evidenced by the approximately 1 order of magnitude longer reaction time required for full FF conversion on Cu. On the $Ni/Al_2O_3$ catalyst, FF was completely converted with a 54.5% yield of THFOL and 30.5% yield of MF after 1 hour, and the product selectivity did not change after 4 hours. The $Ni/TiO_2$ catalyst was less active than $Ni/Al_2O_3$, with some FOL remaining after 1 hour and the product selectivity stabilizing after approximately 4 hours with 70% yield of THFOL and approximately 15% yield of MF. THFOL as the primary product over the Ni catalyst is consistent with the known strong interactions between the furan ring in FF and Ni surfaces, which drives ring hydrogenation. The strong interactions between Ni and $TiO_2$ observed by XPS and TPR and the enhanced THFOL yields on $Ni/TiO_2$ compared to $Ni/Al_2O_3$ indicate that Ni sites near the $TiO_2$ interface coordinate more selectively with the furan ring in FF rather than the carbonyl (or subsequently produced alcohol) group, thus promoting ring hydrogenation rather than carbonyl hydrogenolysis.

Figures 21A, 21B:
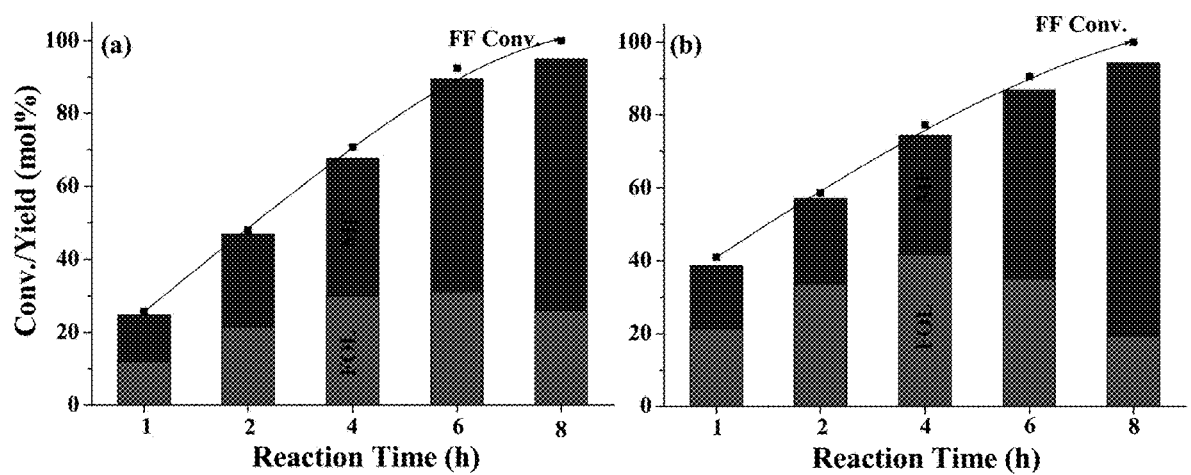
FIGS. 21(a) and 21(b) are illustrations of furfural conversion as function of time over (a) Cu(10 wt %)/$TiO_2$ and (b) Cu(10 wt %)/$Al_2O_3$ catalysts.

In accordance with an exemplary embodiment, Cu catalysts were much less active than Ni catalysts and required approximately 8 hours to achieve complete FF conversion, likely due to their weak ability to activate $H_2$. Similar to the Ni catalysts, $Cu/Al_2O_3$ was more active than $Cu/TiO_2$. FIG. 6 shows that for $Cu/Al_2O_3$ 41% of FF was converted to yield 21.5% FOL and 17.2% MF at 1 hour, while for $Cu/TiO_2$, 25.7% of FF was converted to yield 12.1% FOL and 12.7% MF at 1 hour. Further extending reaction times to 8 hours resulted in complete FF conversion for both catalysts with similar final MF yields of 74.9% for $Cu/Al_2O_3$ and 75.9% for $Cu/TiO_2$. THFOL yields were suppressed on Cu catalysts compared to Ni, due to repulsive interactions between the Cu 3d band and the aromatic furan ring. In accordance with an exemplary embodiment, to more effectively compare FF conversion on the monometallic Cu catalysts, FIG. 21 shows FF conversion and product yields over time on both the $Cu/Al_2O_3$ and $Cu/TiO_2$ catalysts. In both cases, the time dependent yield profile of FOL strongly suggests that this species is an intermediate in the production of MF, as previously reported. There were slight differences in the time dependent yields of FOL and MF for the Cu/TiO$_2$ and Cu/Al$_2$O$_3$ catalysts, particularly at all times less than (<) 6 hours for which higher yields of FOL are realized on Cu/Al$_2$O$_3$ than on Cu/TiO$_2$. These results suggest that the initial hydrogenation of FF to FOL occurs more effectively on Cu/Al$_2$O$_3$, whereas the hydrogenolysis of FOL to form MF occurs more readily on Cu/TiO$_2$. Although Cu/Al$_2$O$_3$ is more active than Cu/TiO$_2$, small amounts of undesired products such as diols and pentanols were obtained at an 8 hour reaction time on Cu/Al$_2$O$_3$. Differences in reactivity of the monometallic Cu catalysts were likely caused by interactions between Cu and the support, which can change the charge state of the active metal or introduce interfacial reaction pathways and the inherent acidity of the support. Comparing Ni and Cu catalysts, in accordance with an exemplary embodiment, it was clear that Ni promotes ring hydrogenation to form THFOL, while Cu is selective for hydrogenolysis to form the desired product MF and that the support composition only mildly influenced catalyst performance.

Figures 7A, 7B:
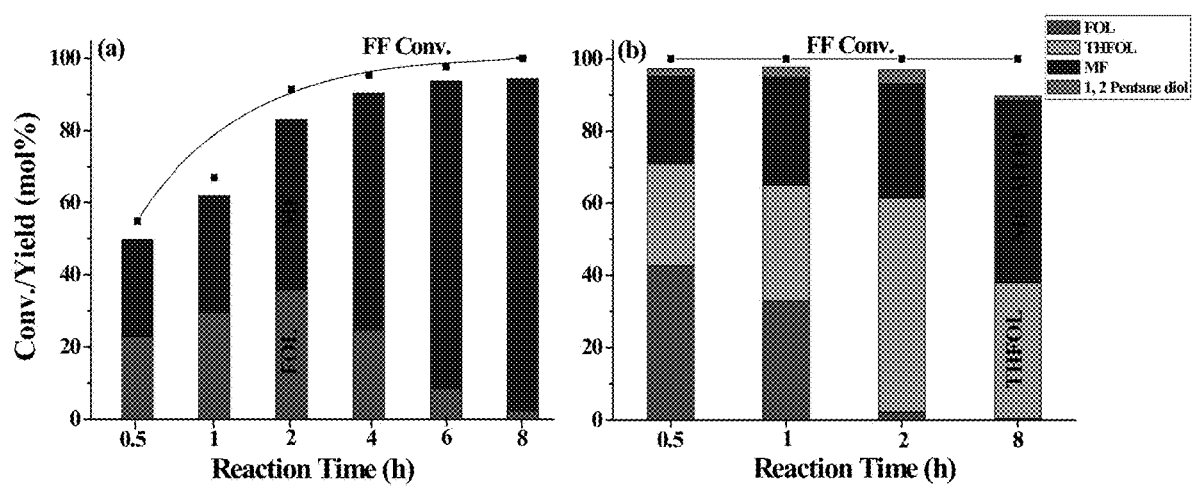
FIGS. 7(a)-7(b) illustrate FF conversion and product yields as function of reaction time over (a) Cu—Ni/TiO$_2$ and (b) Cu—Ni/Al$_2$O$_3$ catalysts. All reactions were run at a FF loading of 1 g, catalyst loading of 0.3 g, 25 mL of 1,4 Dioxane as solvent, temperature of 200° C., and H$_2$ pressure of 25 bar.

While the nature of the support induced relatively small changes in the reactivity of monometallic Cu and Ni catalysts, the support significantly influenced the selectivity and reactivity of FF conversion for the Cu—Ni bimetallic catalysts, as shown in FIG. 7. Cu—Ni/Al$_2$O$_3$ was more active than Cu—Ni/TiO$_2$ with 100% FF conversion achieved in 0.5 hour reaction time for Cu—Ni/Al$_2$O$_3$, whereas 8 hours was required for complete FF conversion on Cu—Ni/TiO$_2$. On Cu—Ni/TiO$_2$, MF and FOL were the primary products, with MF selectivity increasing with reaction time to ultimately achieve a 92.1% yield of MF at 8 hours. Conversely, the Cu—Ni/Al$_2$O$_3$ catalysts favoured furan ring hydrogenation which resulted in increasing THFOL yields with subsequent loss of FOL, as reaction time was extended. When comparing results with Cu—Ni/Al$_2$O$_3$ to those with monometallic Ni and Cu catalysts, both the reactivity (time for complete FF conversion) and product distribution (primarily THFOL, MF and at short times FOL) strongly resembled the behaviour of the monometallic Ni catalysts. Cu—Ni/TiO$_2$ showed reactivity behaviour that was more similar to Cu, with only MF and FOL as significant products. However, Cu—Ni/TiO$_2$ exhibited about 2-fold higher conversion at the same reaction time compared to monometallic Cu/TiO$_2$ and significantly enhanced MF yields at longer reaction times (92% vs. 75.9%).

Figures 8A, 8B, 8C:
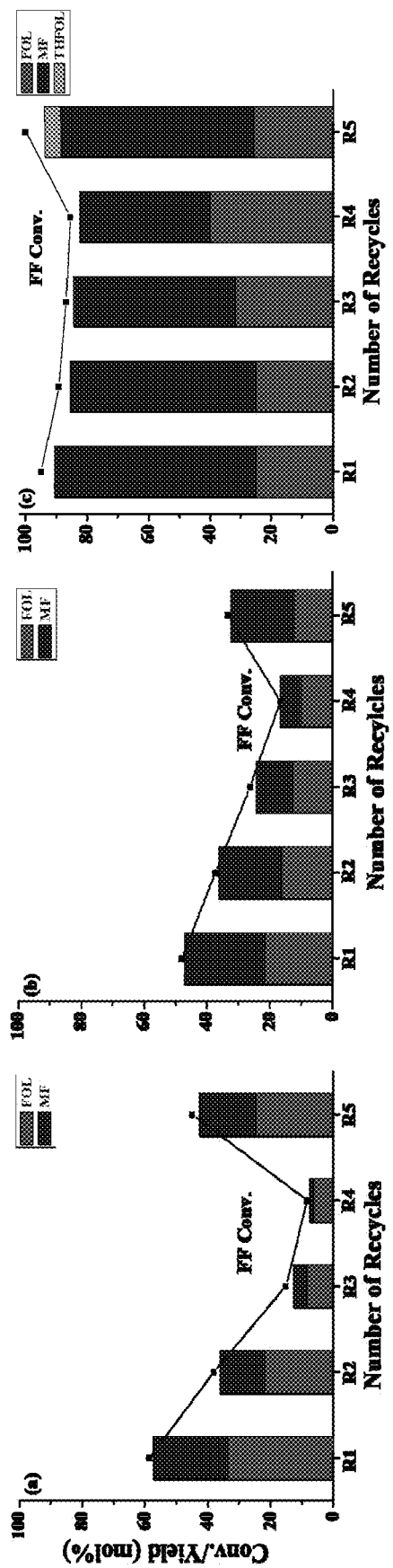
FIGS. 8(a)-8(c) illustrate FF conversion and product yields as a function of number of catalyst recycles, R, for (a) Cu/Al$_2$O$_3$, (b) Cu/TiO$_2$, and (c) Cu—Ni/TiO$_2$ catalysts. After R4, catalysts were calcined at 450° C. for 5 hours and reduced at 450° C. for 3 hours prior to R5. Reaction conditions were a FF loading of 1 g, catalyst loading of 0.3 g, 25 mL of 1,4 Dioxane as solvent, temperature of 200° C., H$_2$ pressure of 25 bar, and 2 hour run time.

Issues previously identified for the application of Cu-based catalysts to FF HDO are the potential for Cu sintering or carbon deposition affecting stability at reaction conditions. To examine these effects, recycle and regeneration experiments were performed where four sequential reactivity experiments were executed without treating the catalyst between experiments, followed by calcination and reduction of the catalysts prior to a final reactivity experiment. In accordance with an exemplary embodiment, it was expected that loss in reactivity during the four sequential experiments could be due to carbon deposits and Cu sintering, while regeneration should predominantly remove carbonacious deposits, allowing differentiation of the catalyst degradation mechanisms. As shown in FIG. 8(a), using the Cu/Al$_2$O$_3$ catalyst, FF conversion dropped from 56% to 10% by the fourth reactivity experiment (R4) and then increased to approximately 47% after a regeneration step (R5), whereas MF selectivity was relatively similar in the first (R1) and fifth (R5) experiment, FIG. 8(a). The results are consistent with previous studies of Cu/Al$_2$O$_3$ catalysts showing low stability under FF HDO conditions. For Cu/TiO$_2$, the FF conversion decreased from 47% to 18% by R4, but increased to 37% following regeneration (R5), with a similar selectivity to R1, FIG. 8 (b). The decreased reactivity degregadation during the 4 sequential experiments (R1-R4) for Cu/TiO$_2$ compared to Cu/Al$_2$O$_3$ suggests that the amount of carbonacious deposits is decreased by the use of TiO$_2$ as a support. However, the similar change in reactivity compare R1 and R5 for Cu/TiO$_2$ and Cu/Al$_2$O$_3$ suggests that Cu sintering similarly occurs for both catalysts.

For the Cu—Ni/TiO$_2$ catalyst, FF conversion decreased from 93.5 to 85.1% from R1 to R4, demonstrating enhanced stability compared to the monometallic Cu catalysts, FIG. 8(c). Regeneration of Cu—Ni/TiO$_2$ restored the MF and FOL yields seen in the initial experiment, although a small amount of THFOL formation was also observed. The results demonstrate that Cu—Ni/TiO$_2$ catalysts exhibit significantly increased resistance to reactivity degradation caused by carbon deposition and sintering compared to Cu/TiO$_2$ and Cu/Al$_2$O$_3$. However, it was also observed that a combination of exposure to reaction conditions and regeneration of the Cu—Ni/TiO$_2$ catalyst resulted in the exposure of small amounts of surface Ni domains that drive ring hydrogenation.

Figures 9A, 9B:
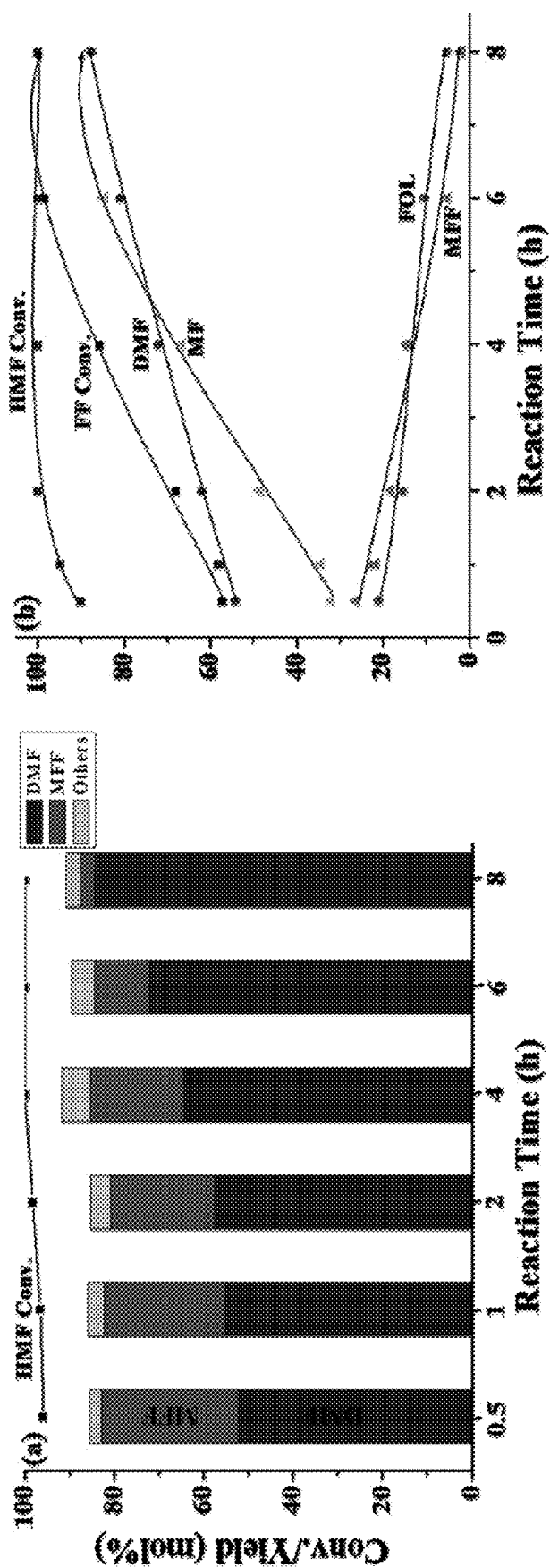
FIGS. 9(a) and 9(b) illustrate (a) HMF and (b) HMF+FF conversion and product yields as a function of reaction time over the Cu—Ni/TiO$_2$ catalyst. For (a), reactions were run at a HMF loading of 0.5 g, catalyst loading of 0.3 g, 25 mL of 1,4 Dioxane as solvent, temperature of 200° C., and H$_2$ pressure of 25 bar. For (b), reactions were run at a FF loading of 0.5 g, HMF loading of 0.25 g, catalyst loading of 0.3 g, 25 mL of 1,4 Dioxane as solvent, temperature of 200° C., and H$_2$ pressure of 25 bar.
Figure 11:
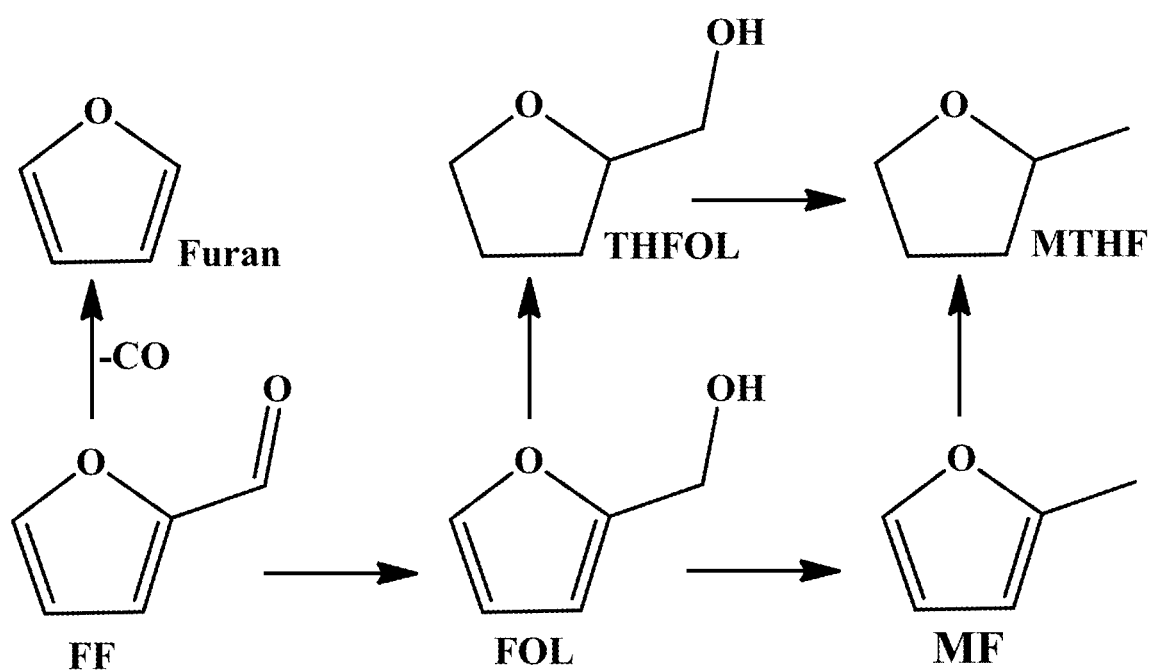
FIG. 11 illustrates a scheme (Scheme 1) for a reaction pathway for FF conversion. FF=Furfural, FOL=Furfuryl alcohol, MF=Methyl furan, THFOL=Tetrahydrofurfuryl alcohol, and MTHF=Methyl tetrahydrofuran.
Figure 12:
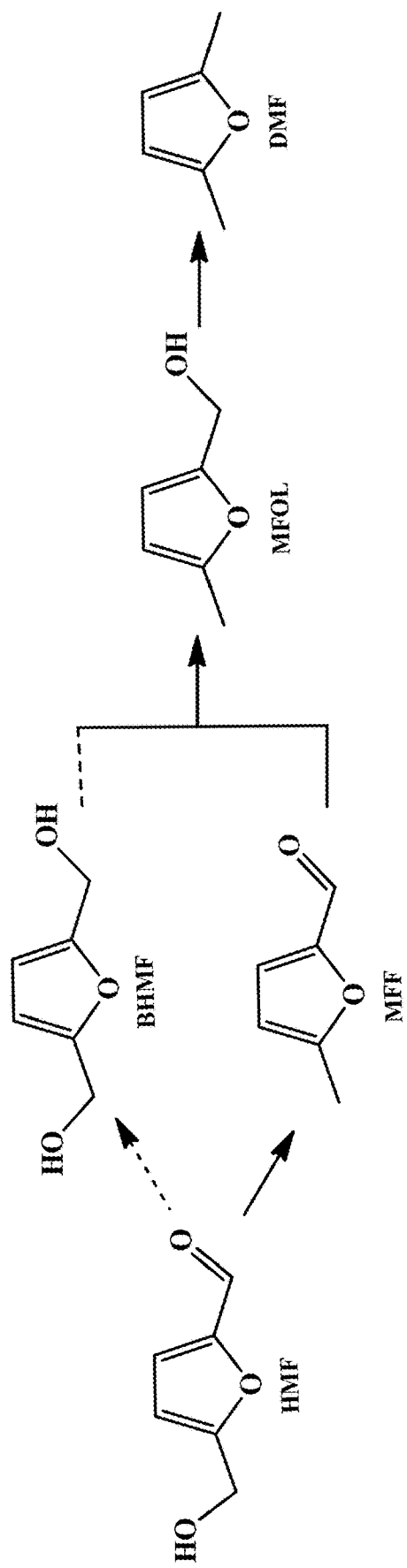
FIG. 12 illustrates a scheme (Scheme 2) for a reaction pathway for HDO of HMF to DMF. HMF=5-Hydroxymethyl furfural, MFF=Methyl furfural, BHMF=Bis hydroxymethyl furan, MFOL=Methyl furfuryl alcohol, and DMF=Dimethyl furan.

HDO of HMF and Co-Processing of FF and HMF:

Because Cu—Ni/TiO$_2$ showed excellent reactivity, MF selectivity, and stability for FF conversion, this catalyst was further tested for reactivity in HMF conversion to DMF and simultaneous co-processing of HMF and FF to DMF and MF, respectively. The measured time dependent conversion of HMF and HMF with FF (co-processing) and product yields on Cu—Ni/TiO$_2$ are shown in FIGS. 9(a) and 9(b), respectively. HMF conversion to DMF is known to occur through two reaction pathways. In the first pathway, hydrogenolysis of HMF yields methyl furfural (MFF) and then hydrogenation followed by hydrogenolysis of MFF to DMF, as shown in Scheme 2 (FIG. 12). In a second pathway, 2,5 bis(hydroxymethyl) furan (BHMF) is the intermediate product, and further hydrogenation of both C—O groups in BHMF results in DMF formation. The conversion of either BHMF or MFF to DMF typically occurs through methylfurfuryl alcohol (MFOL), per Scheme 2. However, MFOL is highly reactive and immediately converts into DMF by hydrogenolysis.

For HMF conversion over Cu—Ni/TiO$_2$, 95.9% conversion of HMF was observed within 0.5 hour of reaction, with the primary products being DMF (52.2% yield) and MFF (30.7% yield). With increasing reaction times, MFF was converted selectively to DMF to ultimately result in 84.3% yield of DMF at 8 hour reaction time. Small amounts of MFOL were also observed as a rapidly converted intermediate in the production of DMF from MFF.

In the co-processing of HMF and FF over Cu—Ni/TiO$_2$, 0.5 g of FF and 0.250 g of HMF were used as reactants with 0.3 g of catalyst at the same reaction conditions as the HMF and FF cases. Cu—Ni/TiO$_2$ showed similar activity and methylated furan (MF+ DMF) yields as in individual processing of HMF and FF. Moreover, based on the time dependent yields of intermediate products (FOL and MFF, for example), the mechanism of methylated furan production did not change for co-processing of FF and HMF. The maximum yields of MF (88.5%) and DMF (87.5%) were realized after 8 hours of reaction at very similar yields as for the individual processing cases.

Summarizing the reactivity results, the monometallic Cu and Ni catalysts showed FF hydrogenation and HDO reactivity consistent with previous reports, and their reactivity exhibited minimal sensitivity to support composition. However, the bimetallic Cu—Ni catalysts showed significant support effects for FF HDO. On $Al_2O_3$, the bimetallic catalyst acted similarly to Ni alone, while on $TiO_2$, the Cu—Ni bimetallic catalyst enhanced rates and MF selectivity compared to Cu alone. The Cu—Ni/$TiO_2$ catalyst showed good stability, regenerability, reactivity, and MF selectivity and outperformed monometallic Cu catalysts in all performance metrics at similar conditions. Finally, Cu—Ni/$TiO_2$ showed excellent selectivity toward methylated furans in HMF and FF/HMF co-processing reactions.

The significant support effect observed for bimetallic Cu—Ni catalysts can be explained and rationalized through the catalyst characterization studies. Cu—Ni/$Al_2O_3$ reactivity studies suggested that the behaviour of the catalyst significantly resembled pure Ni catalysts, where ring hydrogenation was prevalent. Both TPR and XPS showed evidence of equal amounts of Cu and Ni exposed at the catalyst surfaces, while the TEM images suggested that all catalytic particles contained Ni and Cu. On Ni, the primary $\eta^2(C=O)$ FF adsorption geometry brings the aromatic ring close to the surface, enabling ring hydrogenation (FIG. 10). Because the ring-surface interaction is only expected at Ni surface domains that have Ni ensemble sizes large enough to coordinate to the furan ring, or at Cu—Ni alloy surface structures with electronic structures significantly resembling monometallic Ni, it can be concluded that Ni-rich domains at the surface of bimetallic Cu—Ni particles were responsible for a majority of the reactivity of the Cu—Ni/$Al_2O_3$ catalyst. The proposed Cu—Ni bimetallic particle structure on $Al_2O_3$ based on the XPS measurements and reactivity results is shown schematically in FIG. 10.

The Cu—Ni/$TiO_2$ catalyst reactivity significantly resembled that of Cu alone, albeit with enhanced reaction rates and MF selectivity. This result can be explained based on the depth profiling XPS, TPR, and TEM results, which together suggest that $TiO_2$ supported bimetallic Cu—Ni particles segregate into core-shell geometries that preferentially expose Cu at their surface, as shown schematically in FIG. 10. On Cu surfaces, the FF ring is repelled from the surface due to the full valance d-band, forming the $\eta^1(O)$ FF adsorption geometry and thus, as opposed to Ni surfaces, carbonyl hydrogenation is favored on Cu over ring hydrogenation. The enhanced reactivity and MF selectivity on Cu—Ni/$TiO_2$ compared to monometallic Cu catalysts, with no additional ring hydrogenation or decarbonylation, is primarily attributed to increased rates of $H_2$ dissociation. The enhanced rates of $H_2$ dissociation but retained Cu selectivity characteristics could occur at so called single atom surface alloys, where small collections (1-3, essentially small enough so they cannot coordinate to a furan ring) of Ni atoms are exposed at the Cu surface to allow for enhanced $H_2$ dissociation rates but not the $\eta^2(C=O)$ FF adsorption geometry. These reactivity characteristics could also be consistent with a low relative Ni concentration near surface alloy that electronically or sterically modifies the exposed surface Cu atoms and enables enhanced $H_2$ dissociation rates. Although we cannot differentiate these two mechanisms, it is clear that Cu was significantly enriched at the surface in Cu—Ni/$TiO_2$ catalysts, yet still modified by Ni in a manner that enhanced $H_2$ dissociation rates without changes in the inherent preference of Cu for carbonyl hydrogenolysis over ring hydrogenation (see FIG. 10).

The above discussion, combined with the weak influence of the support composition on the reactivity of the monometallic catalysts, strongly suggest that the primary role of $TiO_2$ in promoting the catalytic properties of the Cu—Ni catalyst is indirect, with Ni driven to the $TiO_2$ interface and Cu preferentially exposed at the surface. Thus, $TiO_2$ controls the bimetallic Cu—Ni catalyst surface composition but does not directly participate in the catalytic process. A well-known behaviour on $TiO_2$ supported Ptgroup metal catalysts is strong metal support interactions (SMSI), where support reduction (oxygen vacancy formation) drives $TiO_2$ encapsulation of the active metal particle. While a metal selective SMSI encapsulation state that preferentially encapsulates Ni could be imagined, the TPR data oppose this interpretation. SMSI encapsulation states with $TiO_2$ are typically observed following greater than (>) 500° C. reduction treatment. Because minimal Ni reduction peaks were observed for the Cu—Ni/$TiO_2$ catalysts despite Ni reduction peaks being clearly observable in the Ni—$TiO_2$ catalyst, Ni is likely buried subsurface in the bimetallic particles prior to SMSI encapsulation layer formation. This mechanism is further supported by the XPS analysis of surface composition in the pre-reduced and pre-oxidized Cu—Ni/$TiO_2$ catalysts that show identical Cu/Ni surface concentration ratios in Table 1 (FIG. 13). Thus, preferential interactions between Ni and $TiO_2$ are believed to drive formation of core-shell like particles where Cu is primarily exposed at the catalyst surface, see proposed structures in FIG. 10. In accordance with an exemplary embodiment, support induced bimetallic particle segregation may be quite general for reducible oxide supported bimetallic catalysts, given known metal specific interactions with reducible supports.

The structural properties of Cu—Ni alloys have been extensively studied for their potential application to a range of reactions. Bulk Cu—Ni alloys are miscible and equilibrated into alloy phases when heated above approximately 400° C. In bulk systems (polycrystaline films, single crystaline films, and other structures), Cu surface segregation has been reported to be due to the lower surface energy of Cu in vacuum compared to Ni. It has further been demonstrated that the surface segregation is a facet dependent phenomenon that occurs more predominantly on (100) surface facets compared to (111) surface facets. Insights into the structure of bulk Cu—Ni alloys have not translated into a complete understanding of the structure of supported Cu—Ni alloy nanoparticles, where multiple surface facets are simultaneously exposed, and the distribution of Cu and Ni is also influenced by interfacial interactions with the support and environment.

Previous reports of 50%-50% Cu—Ni alloy nanoparticles supported on irreducible supports ($SiO_2$ and $Al_2O_3$) have found that as-synthesized particles show no evidence of Cu surface segregation. However, reports of Cu—Ni alloy nanoparticles on reducible supports ($CeO_2$, $ZrO_2$, MgO), or supports with significant surface defect concentrations (SBA-15), have shown evidence of Cu enriched surfaces, in agreement with our findings. Thus, while bulk Cu—Ni alloys exhibit Cu surface segregation due to the decreased surface energy of Cu in vacuum, it seems that for supported Cu—Ni alloy nanoparticles preferential Ni-support interactions on reducible or defective supports is the primary driving force for Cu surface segregation. In accordance with an exemplary embodiment, reconstruction of the as-synthesized catalytic structure under reaction conditions may be expected when significant adsorbate-metal specific interactions exist, for example in a CO atmosphere. However based on the lack of ring hydrogenation observed in our studies for the Cu—Ni/$TiO_2$ catalyst, it can be concluded that migration of Ni to the catalyst surface is minimal under reaction conditions.

It is worth comparing our results to recent reports that examined the influence of modification of Cu catalysts with Ni on reactivity in FF HDO. A surface science approach was used to compare pure Cu (111) and Ni (111) surfaces with a Ni surface layer on Cu (111) and a Cu surface layer on Ni (111) for FF hydrogenation. It was clearly seen that in both surface layer configurations, bimetallics enhanced selectivity towards MF formation compared to monometallics. However, even in the case of Cu monolayers on Ni(111), significant nonselective decomposition of FF was observed. This result suggests that for the Cu—Ni/$TiO_2$ catalysts examined here, the Ni concentration in the near surface region is much lower than for the prior surface science study. A separate study of the influence of Ni addition at various concentrations to Cu/$Al_2O_3$ on FF hydrogenation reactivity and selectivity showed that increasing the Ni loading increased the rate of FF conversion, but also increased the selectivity towards ring hydrogenation, decarbonylation, and ring opening products. The introduction of self-assembled organic monolayers to the catalyst lowered the Ni surface content in Cu—Ni/$Al_2O_3$, thereby boosting selectivity and reaction rate for hydrogenation products (FOL was the main product in these studies, which is likely caused by the reactions being performed in the gas phase). In this case, it seems that the use of self-assembled monolayers to control the exposed surface concentration of Ni in bimetallic Cu—Ni catalysts bears some resemblance to our reported use of $TiO_2$ to control the Ni surface concentration in bimetallic Cu—Ni catalysts. Although, the Cu—Ni/$TiO_2$ catalysts reported here enable complete conversion and high yields to MF and are expected to have enhanced stability compared to the organic functionalized Cu—Ni catalysts reported previously, thus creating a more scalable approach for controlling Cu surface chemistry for selective hydrogenation reactions. In addition, it was very recently reported that increasing the Ni content in Cu—Ni/MgAlO catalysts enhanced FF conversion (>99%), however, FOL and THFOL were only selective products observed.

In addition to considering how $TiO_2$ induced segregation of Cu—Ni catalyst particles influenced reactivity and selectivity, it is also interesting to explore how this factor may have influenced stability and catalyst regeneration. In the recycling-regeneration experiments shown in FIG. 8, it was observed that the Cu/$TiO_2$ and Cu/$Al_2O_3$ catalysts exhibited similar performance degradation that is ascribed to carbonaceous deposits on the metal and Cu sintering. The improved stability of Cu—Ni/$TiO_2$ compared to the monometallic catalysts during recycle experiments (R1-R4) is likely due to decreased carbon deposition on the catalysts driven by increased $H_2$ dissociation rates. Increased stability of the Cu—Ni/$TiO_2$ catalyst compared to the monometallic Cu catalysts when considering R1 and R5 is likely due to reduced sintering of the active Cu metal. This suggests that Ni serves as an anchoring site for Cu on $TiO_2$, which enhances catalyst stability and provides a stable platform for regeneration of the core-shell Cu—Ni structure to that for high MF selectivity and reactivity. Further reduction of the Ni loading in Cu—Ni/$TiO_2$ catalysts may allow for similar enhanced reactivity and stability as observed here while also minimizing the surface exposure of Ni observed with increased time under reaction conditions.

Recently, it has been shown that co-solvent-enhanced lignocellulosic fractionation (CELF) of raw biomass enables the production of HMF and FF with extremely high yields. Separation of HMF and FF in a liquid stream from the remaining lignin can be effectively achieved through various approaches to yield a combined stream of HMF and FF that is typically rich in FF. In accordance with an exemplary embodiment, a high yield, single pot conversion of FF and HMF over stable and regenerable Cu—Ni/$TiO_2$ catalysts is disclosed, which opens new possibilities for an efficient and high yield biomass to fuels conversion process with only a few required process steps. It is expected that coupling of CELF pre-treatment of cellulosic biomass with FF/HMF catalytic co-processing will enable an effective approach for conversion of raw biomass to high quality fuels.

In accordance with an exemplary embodiment, Cu—Ni/$TiO_2$ is a unique catalytic material that enabled high yield (~90%) conversion of FF and HMF to methylated furans in either single or co-processing schemes, results not possible with monometallic Cu and Ni, or Cu—Ni/$Al_2O_3$. The reactivity of Cu—Ni/$TiO_2$ is proposed to result from strong and selective Ni—$TiO_2$ interactions that favored in formation of Cu-shell and Ni-core structure, allowing for high selectivity in HDO and enhanced reactivity compared to monometallic Cu catalysts. Furthermore, the strong Ni—$TiO_2$ interactions effectively anchored the bimetallic particles to the $TiO_2$ support, thereby reducing catalyst degradation via sintering and enabling effective regeneration. Finally, it is envisioned that a potentially economical biomass to fuel conversion process can be achieved by coupling CELF pre-treatment of raw biomass to produce high yield liquid streams of HMF and FF with catalytic co-processing using Cu—Ni/$TiO_2$ to high yields of methylated furans.

Optimizing Composition and Support Effects in Cu—Ni Bimetallic Catalysts for Maximizing Activity, Selectivity and Stability in Furfural Conversion to 2-methyfuran In accordance with an exemplary embodiment, supported bimetallic catalysts have been demonstrated to enhance catalytic activity, product selectivity, and catalyst stability over supported monometallic catalysts for a range of catalytic reactions. However, the surface structure and composition of bimetallic particles can differ significantly from the bulk due to variations in surface energies and interactions with adsorbates, making the design of bimetallic catalysts with targeted properties and reactivities challenging. In accordance with an exemplary embodiment, the influence of catalyst support ($Al_2O_3$ and $TiO_2$) on the surface composition and structure of bimetallic Cu—Ni nanoparticles is disclosed with varying Ni weight loading (0, 0.5, 1.5, 3, 5, &10 wt %) at a Cu loading of 5 wt % and a correlation to catalytic reactivity and stability in furfural (FF) hydrodeoxygenation (HDO). Analysis via depth-profiling X-Ray Photoelectron Spectroscopy suggested that over a range of Ni compositions in Cu—Ni/$Al_2O_3$ catalysts, Cu and Ni were distributed evenly within bimetallic particles, although Cu and Ni segregated into contiguous monometallic domains at the particle surfaces. In contrast, on Cu—Ni/$TiO_2$ catalysts near surface alloys formed, which were enriched in Cu at the particle surfaces and exposed only dispersed Ni species. The difference in compositional structure of the Cu—Ni particles on $TiO_2$ and $Al_2O_3$ was attributed to strong and specific interactions between Ni and $TiO_2$. On both supports the addition of Ni to Cu catalysts resulted in significant enhancements in the rate of FF HDO, although $Al_2O_3$ supported bimetallic catalysts promoted hydrogenation of the furan ring, forming mostly furfural alcohol and tetrahydrofurfuryl alcohol, while $TiO_2$ supported catalysts mostly resulted in carbonyl hydrogenolysis to form methyl furan (MF). Through optimization of support and bimetallic compositions, low cost bimetallic catalysts were developed that demonstrated >90% MF yields in FF HDO with good stability and regenerability.

Oxide-supported bimetallic heterogeneous catalysts consisting of late-transition and noble metals can play a significant role in multifunctional chemical transformations, with demonstrated enhancements in catalytic activity, product selectivity, and catalyst stability compared to supported monometallic catalysts. For example, bimetallic catalysts have been shown to exhibit improvements over monometallic catalysts in various catalytic performance metrics for applications including petrochemical processing, ammonia synthesis, three-way catalysis, among many others. While the idea of exploiting the properties of multiple catalytic materials to optimize performance is appealing, bimetallic catalyst design is complicated by the phase space of physical effects that control the relative geometries and organization of the constituent elements at the surface of bimetallic nanoparticles.

Based on the composition, mixing enthalpy, and size of bimetallic particles, various bulk structures can form, including solid solutions, ideal solutions, intermetallic compounds, and biphasic compounds. It is also known that the composition and compositional ordering at bimetallic surfaces may vary from the bulk due to differences in surface energies of the metals. For example, the lower surface free energy of noble metals (e.g., Pd, Pt, and Au) compared to base metals (e.g., Fe, Co, Cu, and Ni) has been demonstrated to induce surface enrichment of the noble metals, forming structures known as near surface alloys. In addition to inherent interactions between the metals controlling the exposed surface structure and composition, it has also been shown that adsorbates can drive segregation of metals in bimetallic particles based on preferential interactions with one of the metals. The demonstrated importance of bimetallic supported catalysts, combined with the inherent complexity associated with structure and reactivity of these catalytic materials, has motivated efforts to develop approaches that allow control of bimetallic surface structures and reactivity in predictable fashions.

The conversion of biomass-derived molecules into fuels and chemicals provides a potentially viable alternative to petroleum based fuels and chemicals, although catalysts that exhibit excellent specificity in the conversion of multifunctional molecules are required to achieve economically viable process yields. Furfural (FF) is a renewable platform chemical that can be produced at high yields from pentose sugars in lignocellulosic biomass by acid hydrolysis of lignocellulosic biomass. Hydrodeoxygenation (HDO) of FF to produce methyl furan (MF) has gained interest due to the potential use of MF as an octane booster to gasoline or as a precursor for diesel or jet fuel range branched alkanes. Achieving high yields in FF conversion to MF requires catalysts that readily dissociate $H_2$ to enable hydrogenolysis of the aldehyde moiety and have concurrent specificity to interact with the aldehyde moiety rather than coordination to the furan ring to minimize unwanted decarbonylation, ring hydrogenation, and ring opening. Achieving this reactivity and specificity requires development of bimetallic or bifunctional catalysts, as monometallic surfaces that enable facile $H_2$ dissociation (e.g., Pt, Pd, Ni etc.) also preferentially coordinate the furan ring, while metal surfaces that selectively interact with the aldehyde (e.g., Cu or Ag) exhibit relatively low rates of $H_2$ dissociation.

Various strategies have been developed to achieve this type of catalytic behavior. For example, single atom alloys with noble metals atoms, such as Pt or Pd, dispersed on Cu surfaces enable $H_2$ dissociation at the noble metal active site and spillover of atomic H onto the Cu surface such that the catalyst can readily dissociate $H_2$ while exploiting the inherent catalytic properties of Cu surfaces. A critical consideration in the design of these materials is whether the relative stoichiometry and organization of the two metal components will remain optimal at the catalytic surface over the catalyst lifetime. For the case of Cu—Ni bimetallic catalytic particles supported on $TiO_2$, support-induced bimetallic particle segregation was disclosed, which occurred where Ni preferentially localized at the $TiO_2$ interface and Cu preferentially localized at the bimetallic particle surface. The existence of a low relative concentration of Ni at the catalytic surface allowed for enhanced rates of FF conversion to MF, as compared to a pure Cu catalyst, while maintaining excellent selectivity typical of pure Cu catalysts. In addition, it was observed that having Ni segregated at the $TiO_2$ interface promoted catalytic stability against particle sintering. These results are promising in terms of the development of low cost, stable, and efficient catalysts for FF conversion to MF. However, because the previous report only considered a single bimetallic composition, a more thorough analysis of the influence of composition on reactivity and stability is required for performance optimization.

In accordance with an exemplary embodiment, a detailed analysis of Cu—Ni bimetallic catalysts is disclosed, relating the influence of metal (with variation in Ni weight loading of 0-10 wt %, at a Cu loading of 5 wt %) and support composition (comparing $TiO_2$ and $Al_2O_3$) to metal particle structure, catalytic reactivity for FF HDO, and catalyst stability. In accordance with an exemplary embodiment, it was observed via depth profiling X-Ray Photoelectron Spectroscopy (DP-XPS) that across a broad range of Ni weight loadings consistent distributions of Cu and Ni were present throughout bimetallic particles when $Al_2O_3$ was used as a support, whereas when $TiO_2$ was used as a support, the bimetallic particle surface was enriched in Cu as compared to the bulk composition. The addition of Ni to Cu(5 wt %)/$Al_2O_3$ catalysts, even at a low 0.5 wt %, resulted in FF ring hydrogenation and reduced MF yields. In contrast, the addition of Ni to Cu/$TiO_2$ at 0-5 wt % promoted FF HDO reactivity while maintaining high MF yields (~85-90%), although the addition of Ni at >5 wt % resulted in reduced MF yields due to ring hydrogenation of MF. Both the stability and regenerability of the Cu/$TiO_2$ catalyst were promoted by the addition of Ni at all tested weight loadings (0-5%), showing quantitative regenerability of the catalytic behavior of the as-synthesized material. In accordance with an exemplary embodiment, by controlling metal composition and importantly metal-support interactions in Cu—Ni bimetallic catalysts, catalytic activity, selectivity, and stability for FF conversion to MF can be optimized. In accordance with an exemplary embodiment, this approach for controlling the surface composition of bimetallic particles can be broadly applicable to catalytic systems that require a balance of reactivity and selectivity.

Materials and Methods:

Synthesis of Monometallic Cu Catalysts

In a typical synthesis, copper (II) nitrate trihydrate (Cu$(NO_3)_2 \cdot 3H_2O$, purity 99%, CAS: 10031-43-3, Aldrich, N.J., USA) was dissolved in 50 mL deionized (DI)-water and added to 5 g of θ-$Al_2O_3$(Catalogue no: 26R-0804UPG, Inframat Advanced Materials, Manchester CT 06042, USA) or $TiO_2$ (P25, Batch No. 4161060398, NIPPON AEROSIL Co., LTD, Evonik, Degussa GmbH) contained in a round bottom flask to obtain a 5 wt % loading of Cu. The solution was mixed and dried at 80° C. in a rotary evaporator. The resulting solids were dried at 100° C. for 12 hours in an oven and calcined at 450° C. for 5 hours in air. Prior to reactivity experiments, catalysts were reduced by pure $H_2$ at a flow rate of 50 mL min$^{-1}$ at 450° C. for 3 hours and cooled to 25° C. under the same environment.

Synthesis of Bimetallic Cu(5 wt %)-Ni(0.5, 1.5, 3, 5, and 10 wt %) Catalysts

Catalysts were prepared by adding the required amounts of Cu(NO$_3$)$_2$·3H$_2$O and Ni(NO$_3$)$_2$·6H$_2$O, (Aldrich, purity 99.99%, Louis, Mo. 63103, USA) precursors simultaneously to achieve 5 wt % of Cu and 0.5, 1.5, 3, 5, and 10 wt % of Ni in 50 ml of DI-water. This solution was added to 5 g of TiO$_2$ (P25) or δ-Al$_2$O$_3$ in a round bottom flask. It was thoroughly mixed and dried at 80° C. using rotary evaporator. The obtained material was dried in a vacuum oven at 100° C. for 12 hours followed by calcination at 450° C. for 5 hours. Prior to reactivity experiments, catalysts were reduced by pure $H_2$ at a flow rate of 50 mLmin$^{-1}$ at 450° C. for 3 hours and cooled to 25° C. under the same environment.

Catalyst Characterization

Transmission Electron Microscopy (TEM):

Transmission electron microscope (TEM) images were obtained using a FEI-Tecnai 12 TEM operating at an accelerating voltage of 120 kV.

X-Ray Photoelectron Spectroscopy (XPS):

XPS experiments were carried out using a Kratos AXIS ULTRADLD XPS system equipped with an Al Kα monochromated X-ray source and a 165-mm mean radius electron energy hemispherical analyzer. Vacuum pressure was kept below 3×10$^{-9}$ torr during analysis. Binding energy calibrations were done with reference to the carbon is peak by adjusting spectra to 284.8 eV. Depth profiling experiments were conducted by Argon sputtering samples for 0, 1, 5, 10, 30, and 60 min with beam voltage of 4 kV, current of 2.35 A, spot size of 3×3 mm$^2$ and vacuum pressure of 3×10$^{-9}$ Torr during acquisition. The surface composition of bimetallic Cu/Ni catalysts was calculated using sensitivity factors of 5.321 and 4.044 for Cu and Ni, respectively.

X-Ray Diffraction (XRD):

XRD spectra of reduced Cu(5%) and Cu(5%)-Ni(3%) on TiO$_2$ and Al$_2$O$_3$ catalysts were recorded in the 2θ range of 20 to 900 using an X'pert Pro PANalytical diffractometer equipped with a Nickel filtered Cu Kα radiation source.

Dispersion Measurements:

Chemisorption studies were carried out on a Micromeritics AutoChem 2920 instrument. In each experiment, 0.1 g of catalyst was placed in a U-tube quartz funnel and purged with Ar gas at 50 mL min$^{-1}$ at 100° C. for 1 h. A gas mixture of $H_2$ (10%)/Ar was passed through the quartz funnel at 25° C. for 1 h with a 50 mL min$^{-1}$ flow rate. The temperature was raised to 350° C. at a heating rate of 10° C. min$^{-1}$ and then temperature was reduced to 50° C. under Ar (50 mL min$^{-1}$) for chemisorption studies. At 50° C., catalysts were treated with 1000 ppm $N_2$O/He with 30 mL min$^{-1}$ flow rate for 1 hour followed by purging with Ar flow (50 mL min$^{-1}$) for 1 hour at constant temperature. Then the temperature was raised to 350° C. at a heating rate of 10° C. min$^{-1}$ with 50 mL min$^{-1}$ flow of $H_2$(10%)/Ar gas and the amount of $H_2$ consumption was measured. Repeated $N_2$O oxidation followed by $H_2$-TPR experiments were conducted and the average hydrogen consumption of 4 sequential experiments was used to calculate dispersion by using a 2:1 Cu/$H_2$ ratio.

Reactivity Measurements

Prior to each reaction, Cu and Cu—Ni catalysts were reduced at 450° C. for 3 hours. Without exposure to air, 0.3 g of reduced catalysts were transferred into a 100 mL stainless-steel Parr micro bench-top reactor (4590 Series, Parr instruments Co., Moline, Ill.) containing 1 g of FF (99.9% pure, Sigma Aldrich) with 25 ml of 1,4-dioxane (HPLC Grade, Fisher Chemicals) as a solvent. The reactor was initially flushed with $H_2$ and then pressurized with $H_2$ gas. Next, the reactor temperature was raised to 200° C., and reactions were conducted for 0.5-8 hours.

Product Analysis

Liquid products were analyzed on an Agilent gas chromatograph (7890A, Agilent Technologies). A DB-WAX Ultra Inert column (Agilent Technologies) that was 30 m long×0.320 mm internal diameter×0.5 micron was used to quantify FF, Furfuryl alcohol (FOL), and tetrahydrofurfuryl alcohol (THFOL) using a flame ionization detector (FID) during the following program: hold for 1 min at 30° C., increase from 30 to 100° C. at a ramp rate of 10° C. min, hold for 2 min at 100° C., increase from 100 to 250° C. at a ramp rate of 10° C. min$^{-1}$. MF and methyl tetrahydrofuran (MTHF) were analyzed using an Hp-5 column that was 30 m long×0.320 mm internal diameter×0.25 micron via FID using the following program: 1 min hold at 30° C., increase from 30-100° C. at a ramp rate of 10° C./min, 2 min hold, increase from 100-325° C. at a ramp rate of 25° C./min and hold for 1 min. Molar yields of the final product were quantified by using calibration curves of standard samples in the gas chromatograph. Mass balances accounting for greater than (>) 95% of the carbon content were obtained in all experiments. Reactant conversion and product yield were calculated as follows:

$$FF \text{ conversion } \% = \left(1 - \frac{\text{Moles of unreacted } FF}{\text{Moles of } FF \text{ before reaction}}\right) \times 100 \quad (1)$$

$$\text{Yields (mol \%)} = \frac{\text{Moles of the product formed}}{\text{Initial mole of } FF} \times 100 \quad (2)$$

Catalyst Recyclability

In accordance with an exemplary embodiment, 0.3 g of freshly reduced catalyst was transferred into a 100 mL stainless-steel Parr reactor containing 1 g of FF and 25 mL of 1,4-dioxane. The reactor was flushed with $H_2$ and then pressurized with $H_2$ to 35 bar. Each reaction was conducted for 2 hours at 200° C. After completion of the reaction, the reactor was cooled by quickly lowering it into a room temperature water bath (25° C.) and depressurizing in the fume hood. Then the catalyst was separated from the liquid by filtration and dried at 105° C. for 3 hours and then reused in four recycle experiments without washing (or) regeneration. Regeneration of the used catalysts was performed via calcination at 450° C. for 5 hours followed by reduction with pure $H_2$ at 450° C. for 3 hours.

Results

Catalyst Characterization

Figures 25A, 25B, 25C:
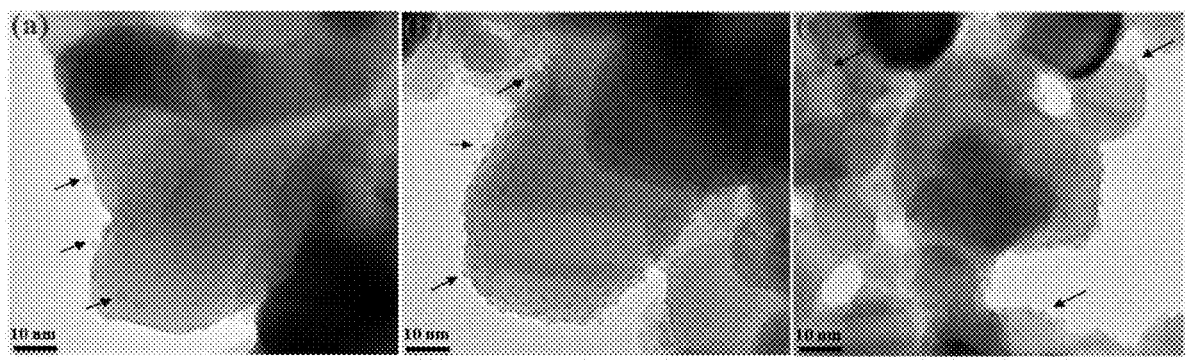
FIGS. 25(a)-25(c) are representative TEM images of bimetallic Cu—Ni/$TiO_2$ catalysts: (a) Cu(5%)-Ni(0.5%)/$TiO_2$, (b) Cu(5%)-Ni(1.5%)/$TiO_2$, and (c) Cu(5%)-Ni(3%)/$TiO_2$. The black arrows point to bimetallic Cu—Ni particles.
Figure 33:
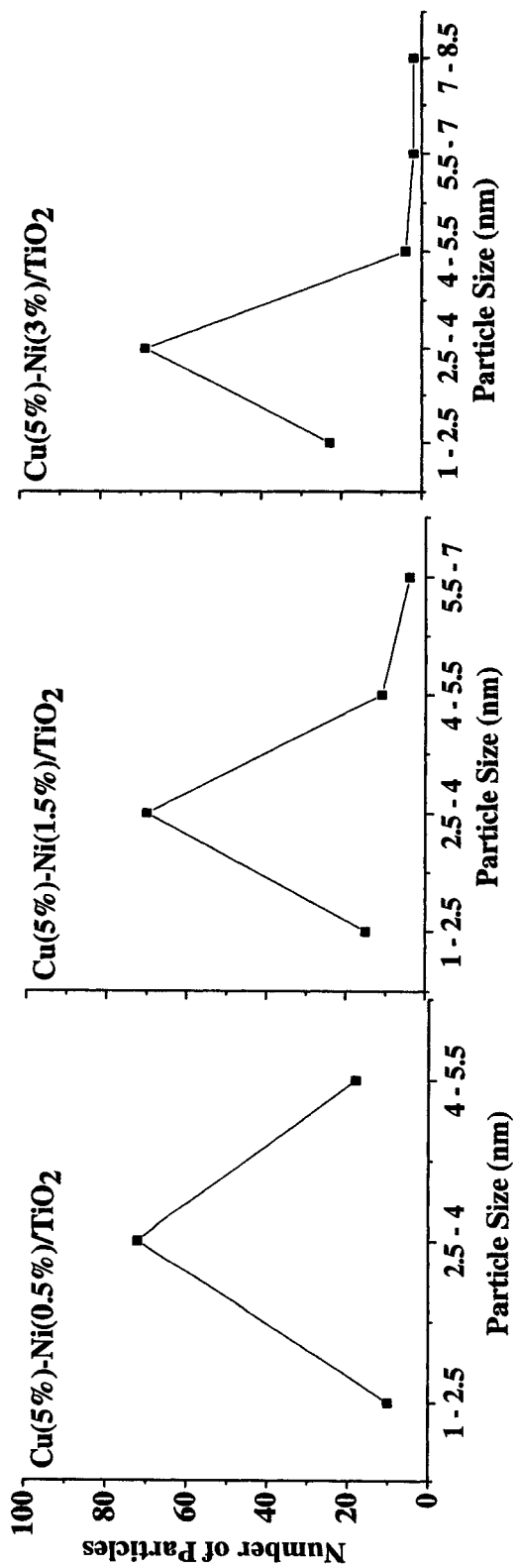
FIG. 33 illustrates particle size distributions from TEM images of bimetallic Cu—Ni on $TiO_2$ catalysts
Figure 34:
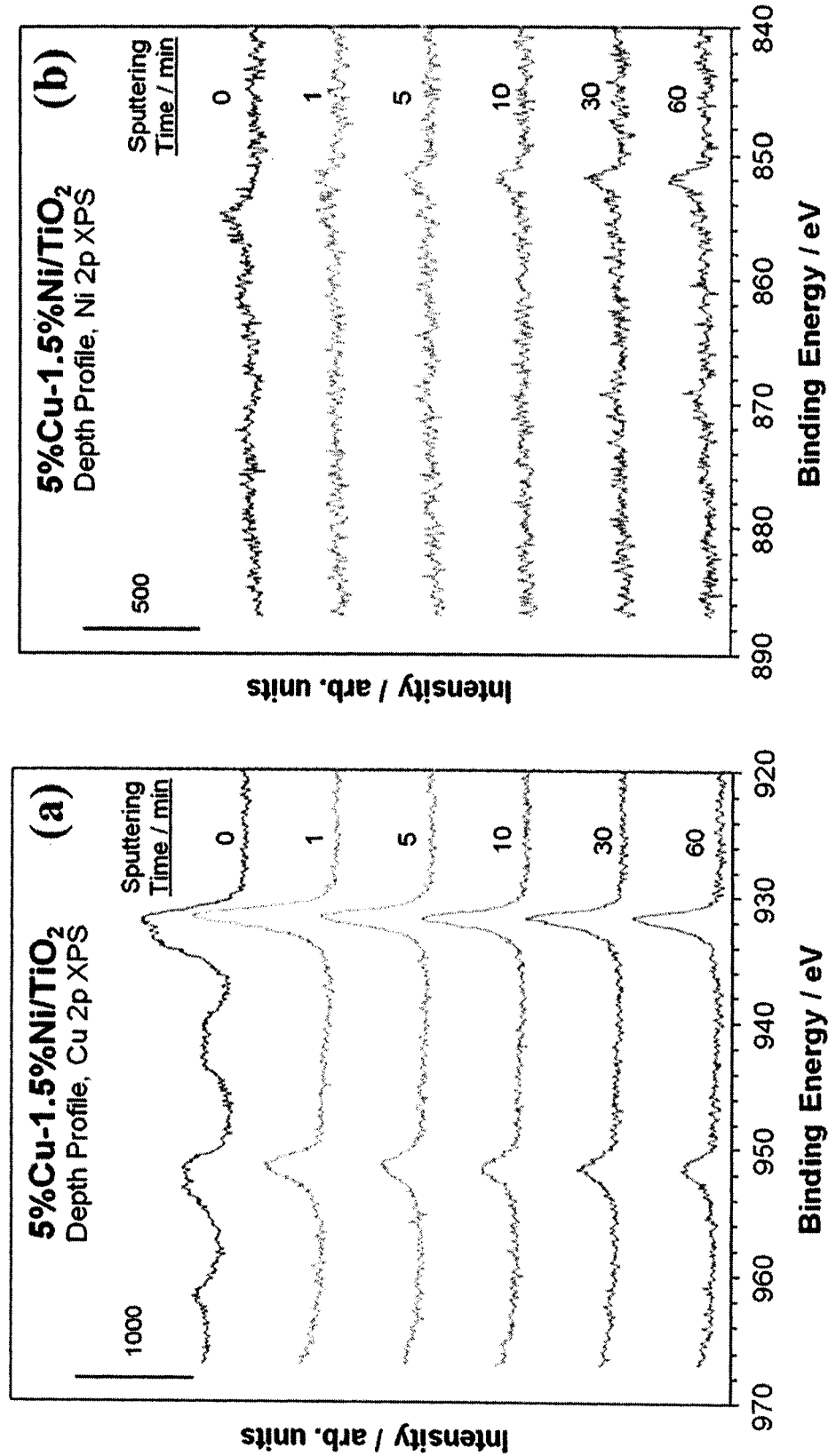
FIG. 34 illustrates XPS depth profiling of Cu(5%)-Ni(1.5%)/$TiO_2$ catalyst. Data derived by Argon sputtering at different time intervals such as 0, 1, 5, 10, 30 and 60 min.
Figure 35:
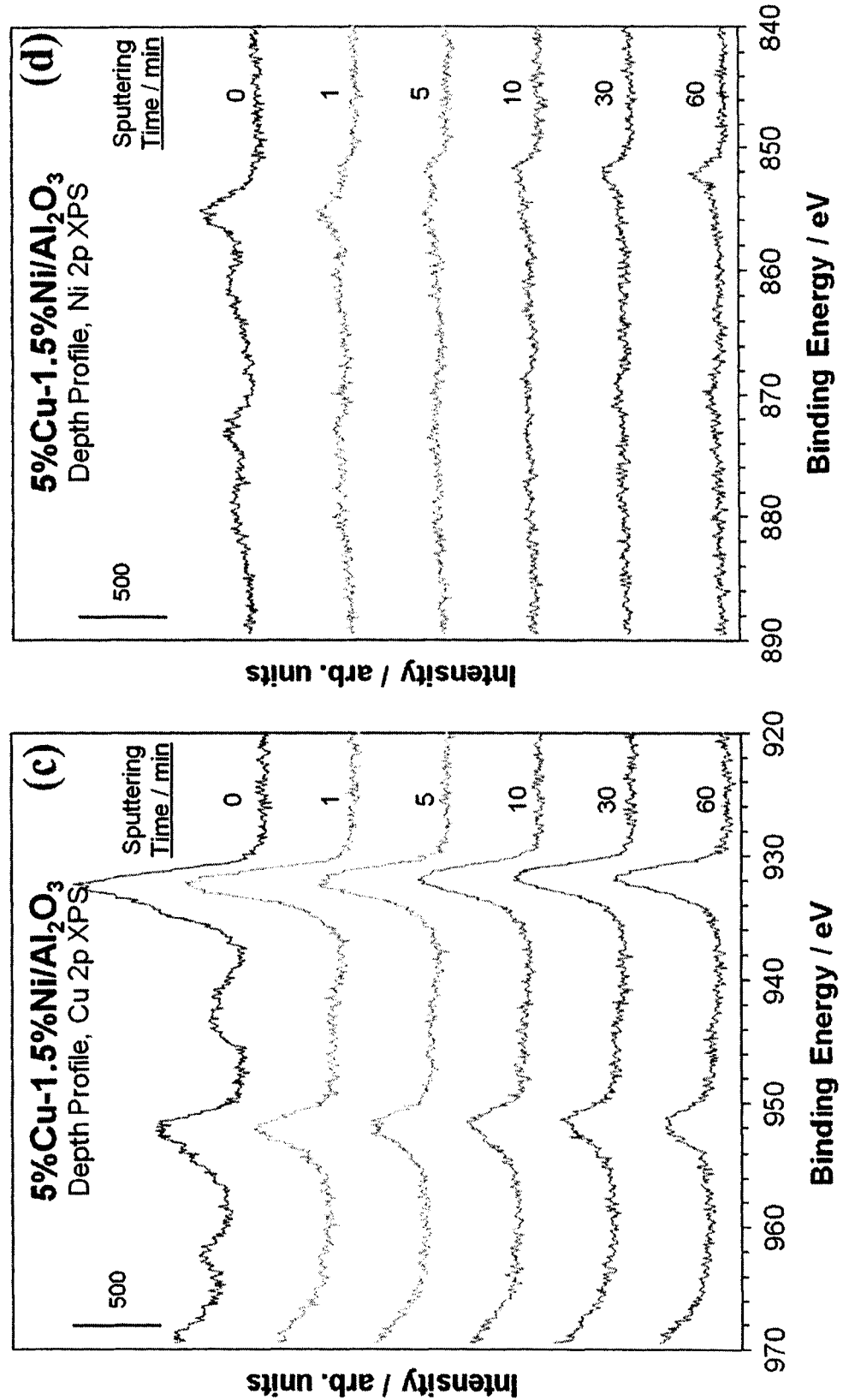
FIG. 35 illustrates XPS depth profiling of Cu(5%)-Ni(1.5%)/$Al_2O_3$ catalyst. Data derived by Argon sputtering at different time intervals such as 0, 1, 5, 10, 30 and 60 min.
Figure 36:
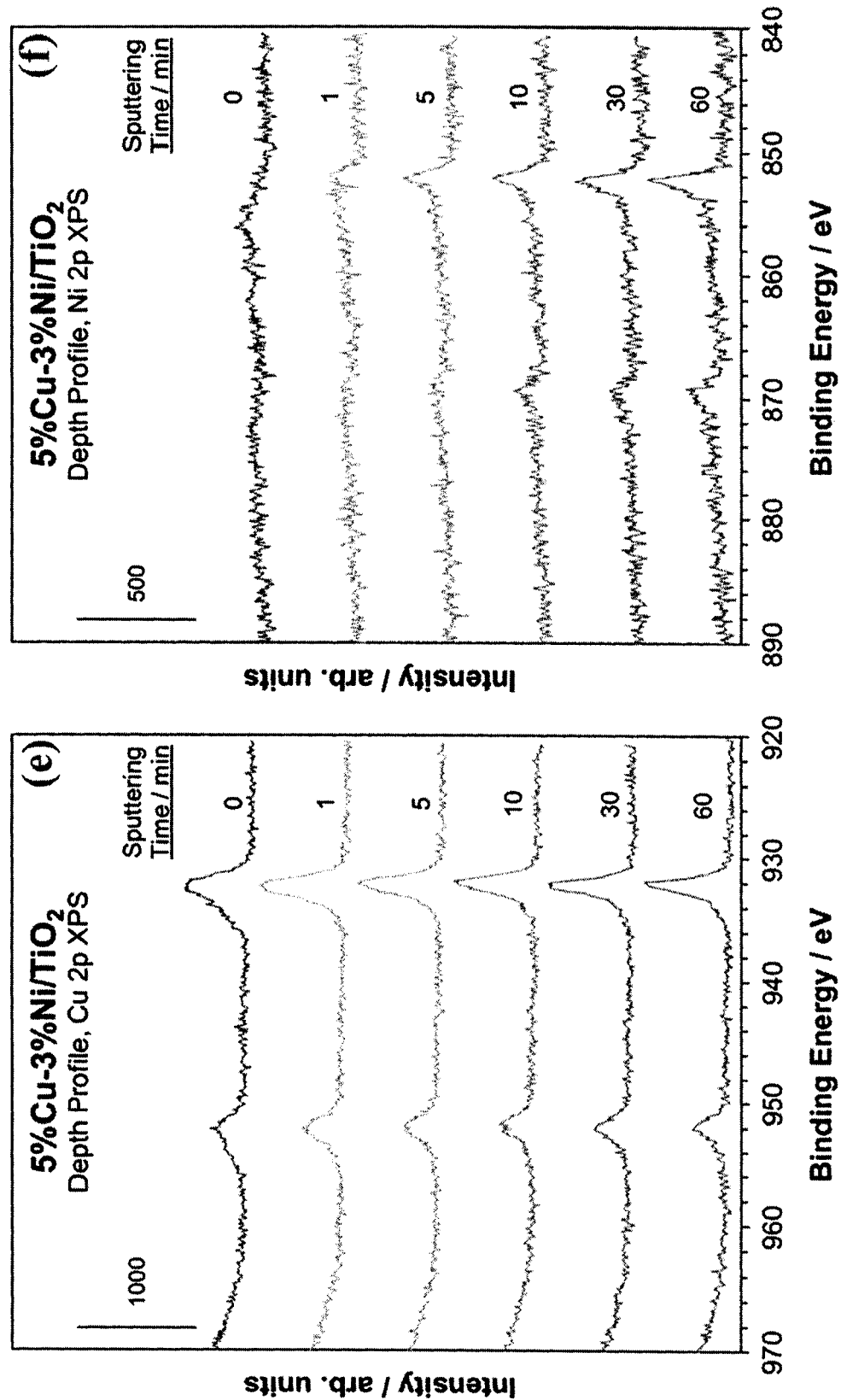
FIG. 36 illustrates XPS depth profiling of Cu(5%)-Ni(3%)/$TiO_2$ catalyst. Data derived by Argon sputtering at different time intervals such as 0, 1, 5, 10, 30 and 60 min.
Figure 38:
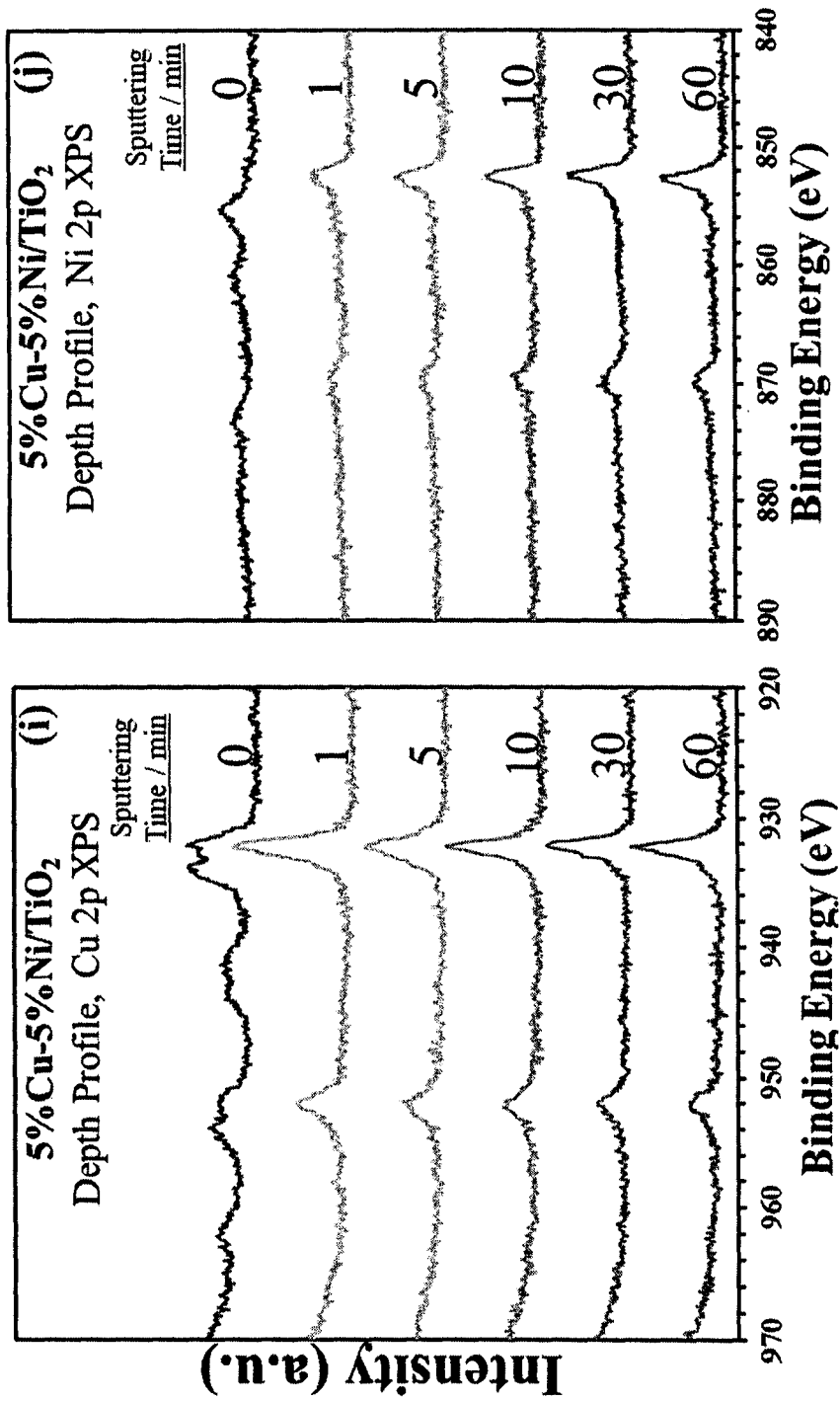
FIG. 38 illustrates XPS depth profiling of Cu(5%)-Ni(5%)/$TiO_2$ catalyst. Data derived by Argon sputtering at different time intervals such as 0, 1, 5, 10, 30 and 60 min.
Figure 39:
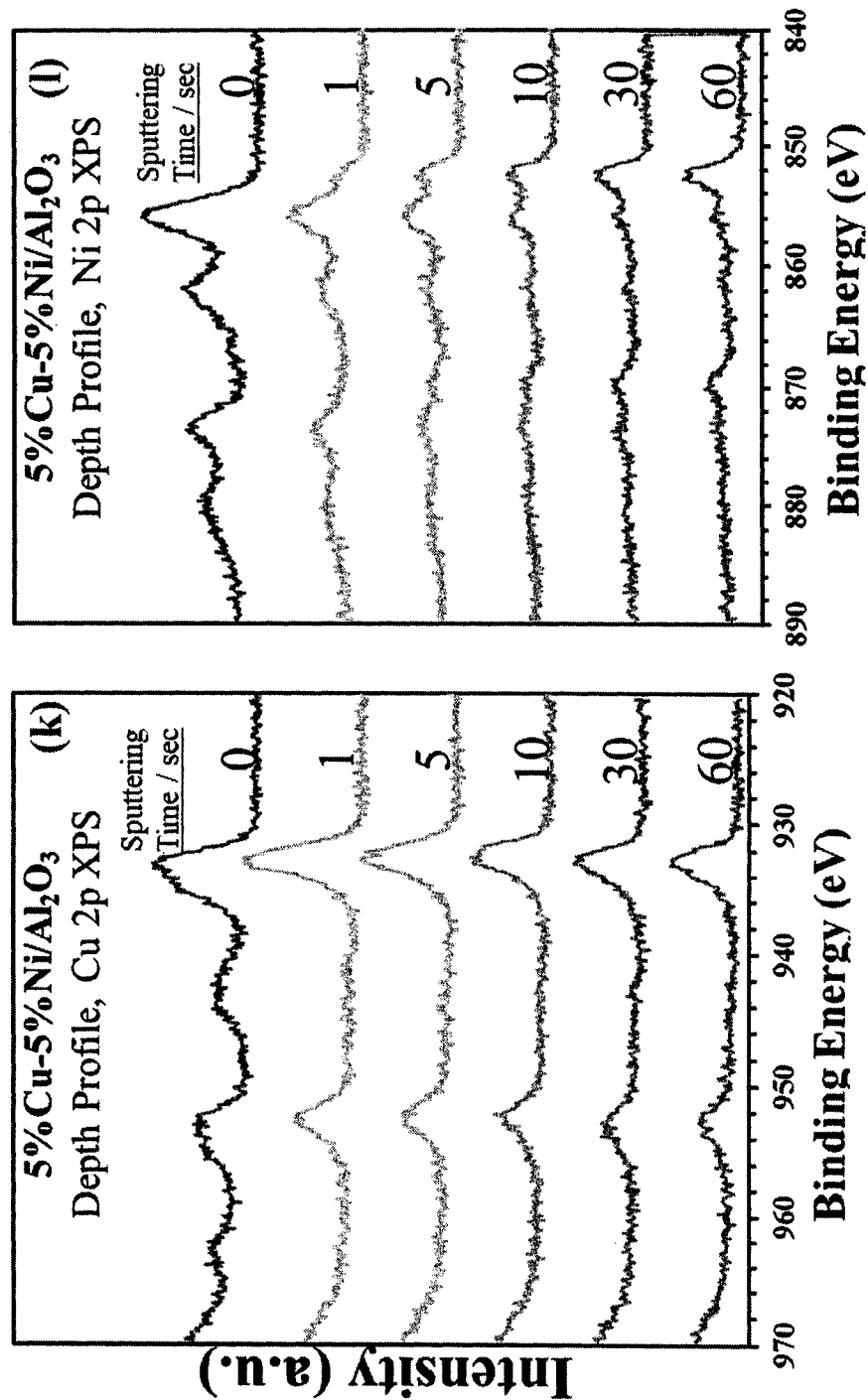
FIG. 39 illustrates XPS depth profiling of Cu(5%)-Ni(5%)/$Al_2O_3$ catalyst. Data derived by Argon sputtering at different time intervals such as 0, 1, 5, 10, 30 and 60 min.

A series of catalysts with varied Ni loading and support were synthesized, consisting of Cu(5 wt %)-Ni(0, 0.5, 1.5, 3, 5, and 10 wt %)/TiO$_2$ and Cu(5 wt %)-Ni(0, 0.5, 1.5, 3, and 5 wt %)/Al$_2$O$_3$. Prior examination of Cu(5 wt %)-Ni(5 wt %) catalysts on TiO$_2$ and Al$_2$O$_3$ with TEM-based energy dispersive spectroscopy revealed that all observed metal particles contained both Cu and Ni, suggesting consistent formation of bimetallic particles. The analysis was consistent with the characterization using temperature-programmed reduction and X-ray diffraction, which both showed evidence of the formation of bimetallic particles. Based on this previous analysis, we focused here on analyzing the influence of Ni loading on the structure (both geometric and spatially varying composition) of the Cu—Ni bimetallic particles. Representative TEM images of Cu(5 wt %)-Ni(X wt %)/TiO$_2$ catalysts with Ni loadings of 0.5, 1.5, and 3.0 wt % are shown in FIGS. 25(*a*)-25(*c*). The average Cu—Ni particle diameter, standard deviation, and size distribution (FIG. 33) was measured by characterizing greater than (>) 100 particles from corresponding TEM images of each sample. The average Cu—Ni particle size was statistically similar in these three representative materials: Cu(5 wt %)-Ni(0.5 wt %) approximately 3.3±0.7 nm>Cu(5 wt %)-Ni(1.5 wt %) approximately 3.1±0.8 nm>Cu(5 wt %)-Ni(3 wt %) approximately 3.0±1.0 nm. The particle size distributions were relatively tight in all cases examined, with only a few metallic particles with diameters>5 nm for the catalysts containing 1.5 and 3 wt % Ni. The particle sizes are in reasonable agreement with dispersions of 15.9% and 27.1% that give estimated average Cu particle diameters of 6.3 nm and 3.8 nm measured by N$_2$O titration for Cu(5%)/TiO$_2$ and Cu(5%)/Al$_2$O$_3$, respectively. In accordance with an exemplary embodiment, previous conclusion that observed support effects on FF HDO reaction selectivity were not significantly influenced by differences in metal particle size of the same magnitude of variation observed, focused on analyzing the spatial distribution of Cu and Ni in bimetallic particles as a function of metal and support composition was the focus. In accordance with an exemplary embodiment, differences in metal particle sizes as a function of support influenced the inherent reactivity of the catalysts were noted.

To analyze the spatial distribution of Cu and Ni in the bimetallic particles of varying composition on Al$_2$O$_3$ and TiO$_2$ supports, DP-XPS spectra were collected for the Cu—Ni catalysts as a function of Ar ion sputtering time. Because these are supported catalysts, relationships between sputtering time and sputtering depth are difficult to interpret. Thus, the data is simply reported as a function of Ar sputtering time, which is assumed to be proportional to depth into the Cu—Ni particles. The relative Cu and Ni concentration were calculated by summing all contributions to the Cu 2p3/2 and Ni 2p3/2 peaks and normalizing by their relative cross-sections (sensitivity factors).

Binding energy values for the Cu$^0$ and Ni$^0$ components of the 2p3/2 peaks were in the range of 931.8 to 932.3 and 851.8 to 852.9 eV, respectively, consistent with values reported in the literature. Increasing the Ni loading from 1.5 to 5% increased the binding energy for the Ni$^0$ 2p3/2 peak by ~0.4-0.5 eV for both the TiO$_2$ and Al$_2$O$_3$ supports (FIG. 42—Table S1). However, when TiO$_2$ was used as a support, the Cu$^0$ 2p3/2 peak position shifted up in binding energy by ~0.5 eV as the Ni loading increased, while the Cu$^0$ 2p3/2 peak position stayed essentially constant as Ni loading was varied on the Al$_2$O$_3$ supported catalysts. These results suggest that when Al$_2$O$_3$ was used as a support, Ni had minimal influence on the electronic environment of Cu, whereas when TiO$_2$ was used as a support, Ni addition significantly modified the local environment of Cu.

Figures 2, 16:
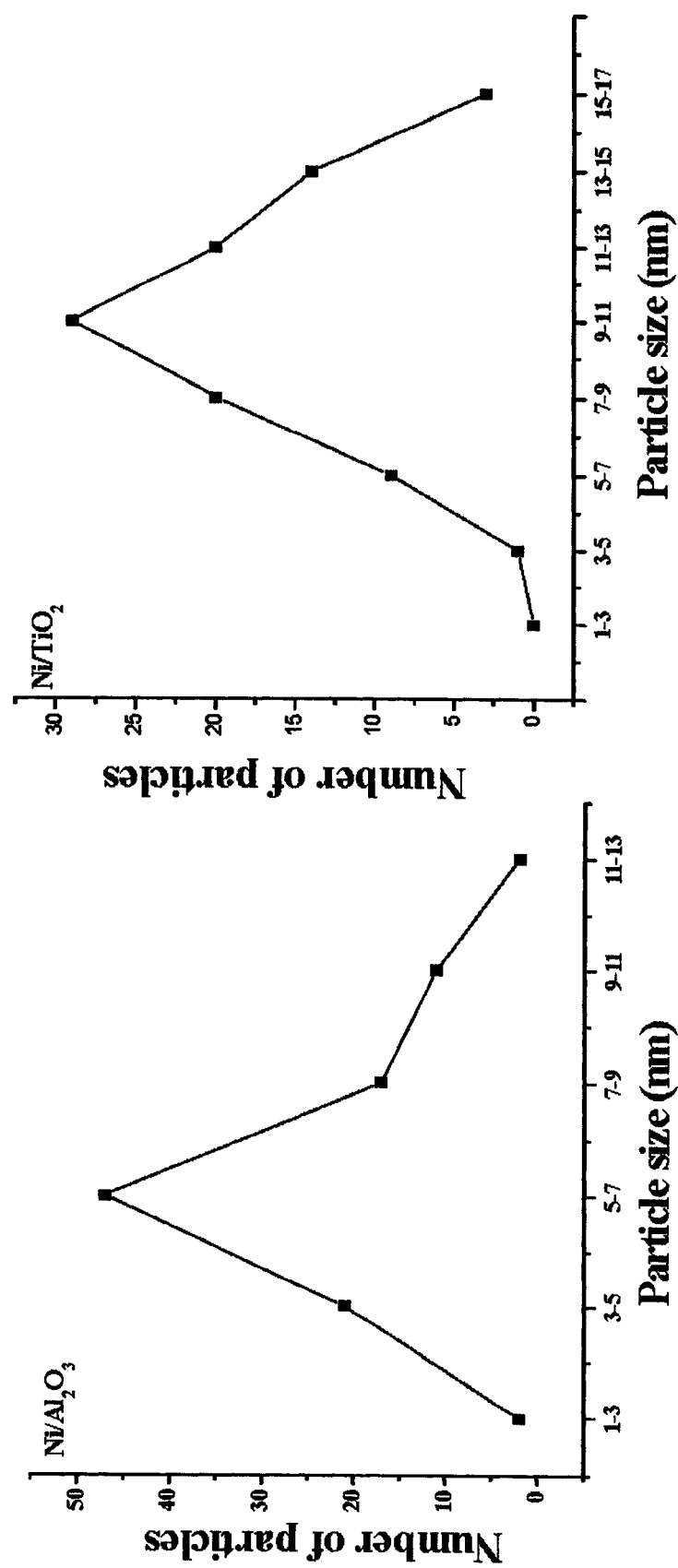
Figures 3, 16:
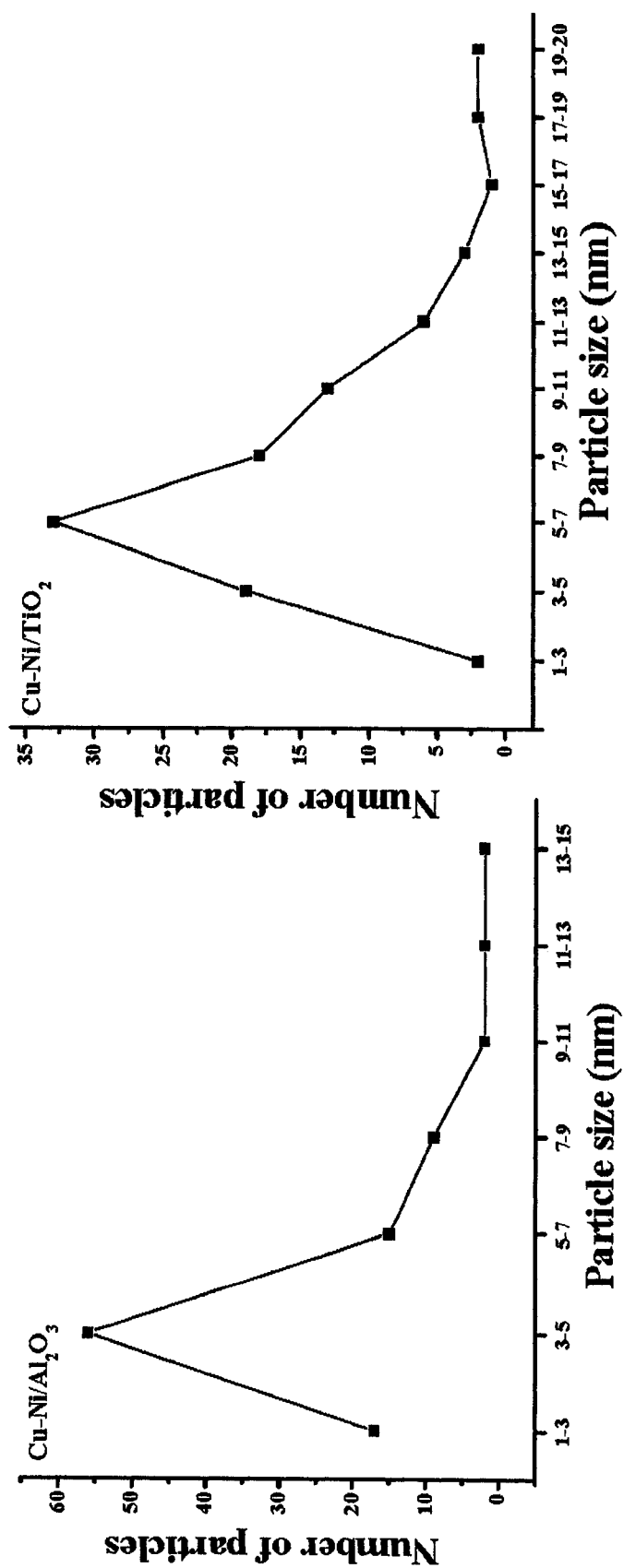

The DP-XPS composition profiles for Cu(5%)-Ni(1.5%, 3%, & 5%) on TiO$_2$ and Al$_2$O$_3$ are shown in FIG. 2, with the corresponding spectra in FIGS. 34-39. In each case, Ar sputtering was applied for approximately 60 minutes, which was found to be sufficient for the relative Cu and Ni concentrations to converge toward a bulk value. FIG. 26(*a*) shows the DP-XPS profiles for Cu(5%)-Ni(1.5%) on TiO$_2$ and Al$_2$O$_3$, plotted in terms of the relative percent of Cu and Ni at each sputtering time. Given the nominal weight loadings, a Cu:Ni ratio of 77%:23% would be expected if the metals were evenly distributed throughout the bimetallic particles. For the Al$_2$O$_3$ support, an almost constant 72-76% nominal Cu % was observed at Ar sputtering times between 0-30 minutes, with a slight increase to approximately 81% Cu at 60 min Ar sputtering. This result suggests that the Cu and Ni were distributed virtually homogeneously in the samples at close to the nominally expected relative concentrations. However, for the TiO$_2$ supported catalyst, an 88% Cu relative concentration was measured prior to Ar sputtering and then steadily converged toward 82% at 60 minutes of Ar sputtering time.

The Cu(5%)-Ni(3%) and Cu(5%)-Ni(5%) catalysts showed similar behavior as the Cu(5%)-Ni(1.5%) catalysts, where the Cu concentration was enhanced at the bimetallic particle surfaces as compared to the bulk for a TiO$_2$ support, FIGS. 26(*b*) and 26(*c*). For the Cu(5%)-Ni(3%) catalyst, the relative Cu surface concentration (Ar sputtering time=0) was ~25% greater when TiO$_2$ was used as a support as compared to Al$_2$O$_3$(85% for TiO$_2$ versus 60% for Al$_2$O$_3$), whereas this difference increased to 30% for the Cu(5%)-Ni(5%) catalyst (80% for TiO$_2$ versus 50% for Al$_2$O$_3$). In addition, for the Cu(5%)-Ni(3%) and Cu(5%)-Ni(5%) catalysts as Ar sputtering time increased to 60 minutes, the Cu and Ni relative concentrations converged towards the expected nominal loadings on the TiO$_2$ and Al$_2$O$_3$ supported catalysts. In contrast, the Cu and Ni relative concentrations varied only slightly as a function of Ar sputtering time and from the expected nominal concentrations when Al$_2$O$_3$ was used as a support.

In all analyzed cases, we observed evidence of a significant influence of the support on the composition structure of the bimetallic Cu—Ni particles, where when TiO$_2$ was used as a support Cu was enriched at the catalyst surface, while on Al$_2$O$_3$, Cu and Ni were present in close to the nominal concentration throughout the catalyst particles. Comparing the TiO$_2$ supported catalysts, the Cu surface loading (at Ar sputtering time=0) decreased from 88% to 80% as the Ni loading increased from 1.5% to 5%. However, for the Al$_2$O$_3$ supported catalysts the Cu surface loading varied more significantly, from 72% to 51% as Ni loading was increased, which is consistent with the expected decrease from 77% to 50% based on nominal metal loadings. From this analysis, it is clear that at all explored Ni loadings, TiO$_2$ induces Cu segregation to the bimetallic particle surfaces, while maintaining a small 10-20% Ni surface concentration.

Catalytic Activity Studies

Figure 27:
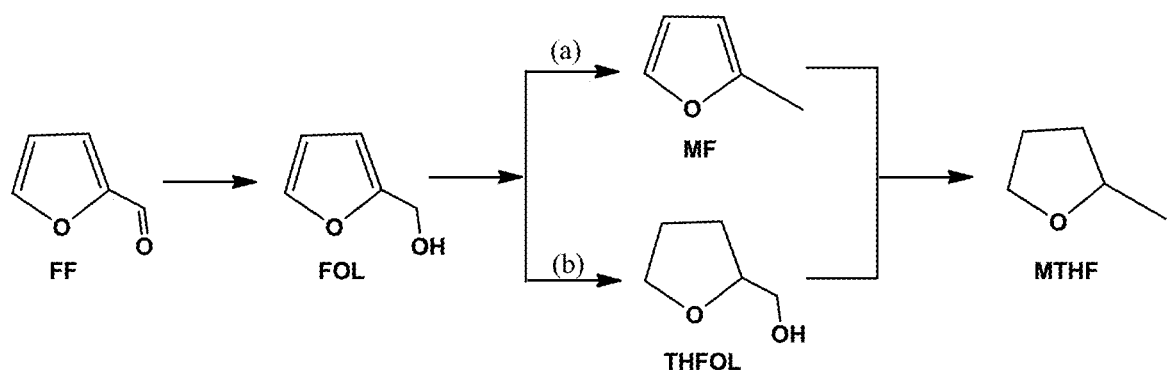
FIG. 27 is a scheme (Scheme 1) illustrating FF hydrogenation reaction pathways. Path (a) represents the hydrogenolysis of FOL to MF followed by ring hydrogenation of MF to form MTHF, and wherein Path (b) represents furan ring hydrogenation in FOL to form THFOL followed by further hydrogenolysis THFOL to form MTHF.

HDO of FF to MF occurs through sequential steps, where initial hydrogenation of the FF carbonyl group forms FOL and further hydrogenolysis of FOL produces MF, Scheme 1 (FIG. 27). An unwanted side product, THFOL, can form from ring hydrogenation of FOL and is commonly observed on catalysts that promote coordination with the furan ring. Another unwanted side product, MTHF, could form from either furan ring hydrogenation of MF, or hydrogenolysis of THFOL, Scheme 1 (FIG. 27). Thus, to maximize reactivity and selectivity for MF formation, a catalyst must be able to drive H$_2$ dissociation facilely, while minimizing coordination to the furan ring.

Figure 40:
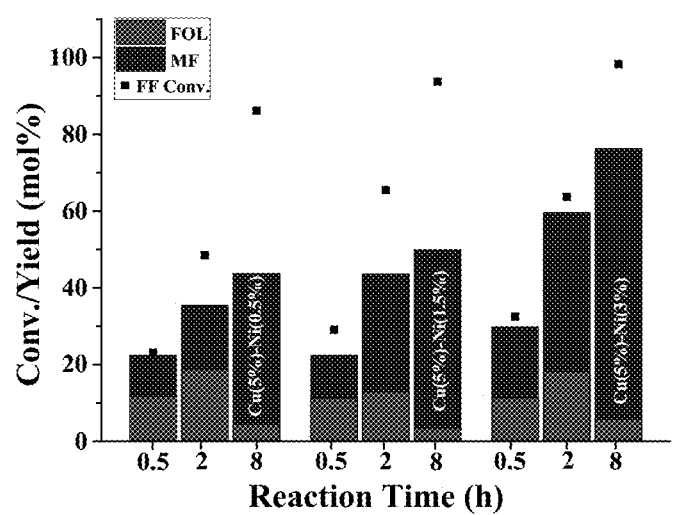
FIG. 40 illustrates FF conversion as a function of time over supported bimetallic Cu—Ni on $TiO_2$ catalysts. Reaction conditions: 1 g of FF, 0.3 g of catalyst, 25 ml of 1,4-dioxane, 200° C. reaction temperature and 25 bar of $H_2$ at room temperature.

In order to explore how the bimetallic Cu—Ni composition and support influences reactivity, selectivity, and stability in the FF HDO reaction, preliminary experiments were conducted over Cu(5%)-Ni(0.5, 1.5, and 3%)/TiO$_2$ catalysts at reaction times between 0.5-8 hours, H$_2$ pressure between 25-45 bar, with 25 ml of 1,4-dioxane as a solvent, 30 wt % catalyst to FF loading, and a temperature of 200° C. FIG. 40 shows the FF conversion, MF yield, and FOL yield (the 2 major identified products) over Cu(5%)-Ni (0.5, 1.5, & 3%)/TiO$_2$ catalysts as a function of reaction time. FF conversion increased with reaction time and MF was the major product for all catalysts. However, at 8 hours reaction time the total yields of identified products were between 50% and 75%, while greater than 85% FF conversion was observed for all catalysts. It is proposed that the unquantified products derived from FF degradation, which is known to occur when low loadings of catalysts with minimal ability for $H_2$ dissociation are used. To overcome this, the influence of $H_2$ pressure was examined by measuring the FF HDO reaction at 25, 35, and 45 bar over the Cu(5%)-Ni(0.5%)/$TiO_2$ catalyst, see FIG. 43 (Table S2). At 35 bar $H_2$ pressure, MF yields increased to >90% at 100% FF conversions and no further increase was seen at 45 bar $H_2$ pressure. Therefore, further studies comparing the influence of catalyst composition on FF HDO activity, selectivity, and stability were executed at 35 bar $H_2$ pressure, with all other conditions held constant.

Figure 28:
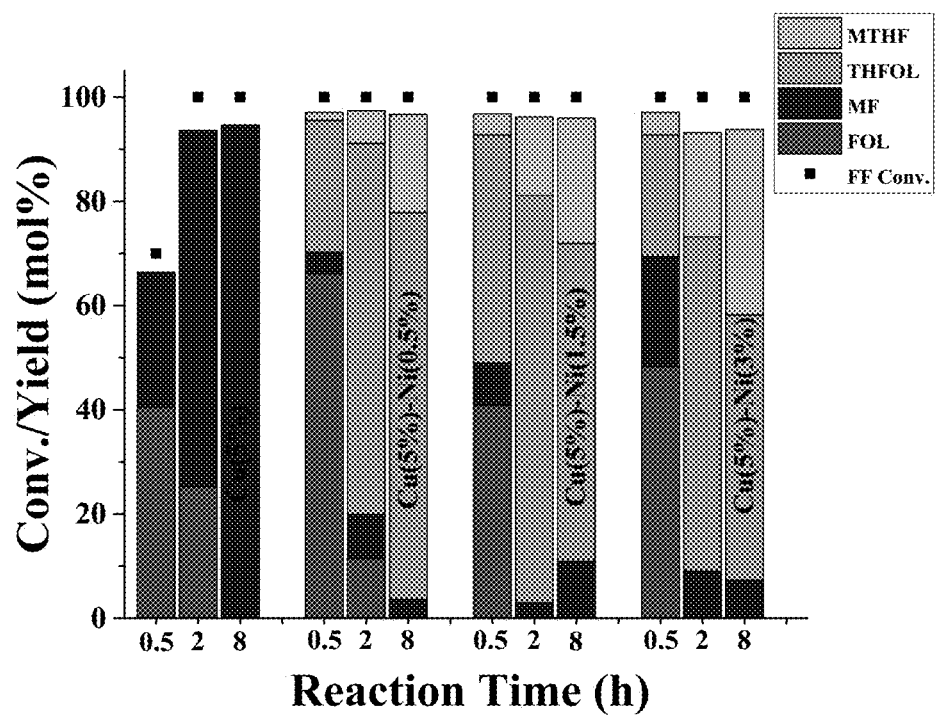
FIG. 28 is an illustration of FF conversion and product yields as a function of reaction time on Cu/$Al_2O_3$ and Cu—Ni/$Al_2O_3$ catalysts. The catalyst composition is noted in the 8 hours reaction time bar. All reactions were conducted at FF loading of 1 g, catalyst loading of 0.3 g, 25 ml of 1,4-dioxane as a solvent, and at a temperature of 200° C. The reactor was pressurized with 35 bar $H_2$ gas at 25° C.

FIG. 28 shows FF conversion and product yields over monometallic Cu(5%) and bimetallic Cu(5%)-Ni(0.5, 1.5, and 3%)/$Al_2O_3$ catalysts as a function of reaction time. On Cu(5%)/$Al_2O_3$, FF conversions were 70% and 100% at 0.5 and 2 hours reaction time, respectively, and a maximum of 94.6% MF yield was obtained at 8 hours reaction time. The addition of 0.5% Ni caused an increase in catalytic reactivity, where complete FF conversion was observed within 0.5 hour. However, the dominant products were FOL and THFOL at all explored reaction times, with 74.2% and 18.9% yields of THFOL and MTHF observed, respectively, at 8 hours reaction time.

The product distribution as a function of time was similar for the Cu(5%)-Ni(1.5 and 3%)/$Al_2O_3$ catalysts as compared to Cu(5%)-Ni(0.5%)/$Al_2O_3$, with THFOL and MTHF being the dominant products. Consistently across the Cu(5%)-Ni (0.5, 1.5 and 3%)/$Al_2O_3$ catalysts, it was observed that FOL was the most favored product at short times, followed by THFOL at intermediate times and increasing MTHF at longer times. Thus, for the $Al_2O_3$ supported bimetallic Cu—Ni catalysts a dominant reaction pathway exists where FF is first hydrogenated to FOL, followed by ring hydrogenation to THFOL and finally hydrogenolysis to MTHF (Scheme 1, Path b). Clearly, Ni enhanced the reactivity of the Cu/$Al_2O_3$ catalyst; however, the selectivity to MF was significantly diminished at all explored Ni loadings.

Figure 29:
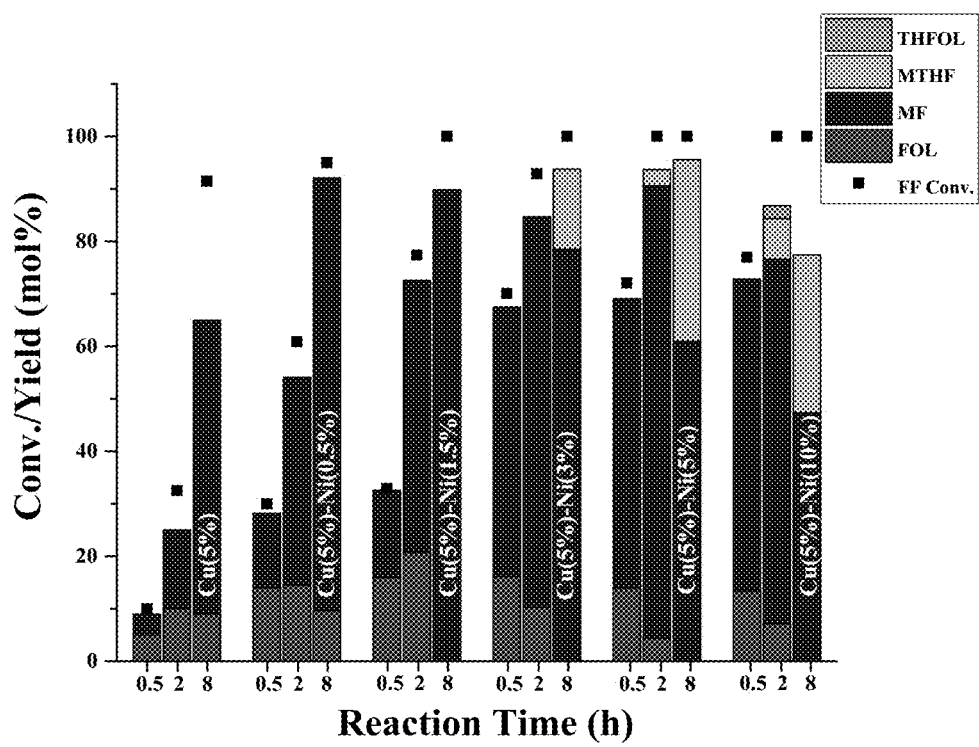
FIG. 29 is an illustration of FF conversion and product yields as a function of time on Cu/$TiO_2$ and Cu—Ni/$TiO_2$ catalysts. The catalyst composition is noted in the 8 hours reaction time bar. All reactions were conducted at FF loading of 1 g, catalyst loading of 0.3 g, 25 ml of 1,4-dioxane as a solvent, and at a temperature of 200° C. The reactor was pressurized with 35 bar $H_2$ gas at 25° C.

On the monometallic Cu(5%)/$TiO_2$ catalyst, FOL and MF were observed as the primary products, with a maximum MF yield of 53% and FF conversion of 91.5% at 8 hours reaction time, FIG. 29. As was observed for reactions run at lower $H_2$ pressures, FIG. 40, the low rates of dissociative $H_2$ adsorption on the Cu(5%)/$TiO_2$ catalysts led to FF degradation instead of hydrogenation. The observation of higher reactivity for monometallic Cu catalysts on $Al_2O_3$ compared to $TiO_2$ is consistent with the differences in measured Cu dispersion for these catalysts of 27.1% for Cu(5%)/$Al_2O_3$ and 15.7% for Cu(5%)/$TiO_2$. Previous study demonstrated that apart from the difference in reactivity of Cu on $Al_2O_3$ and $TiO_2$, which can be explained by the different in dispersion, differences in surface acidity of the support seemed to not contribute to differences in reactivity of the catalysts. Based on this, any differences in reactivity or selectivity of Cu—Ni catalysts on $Al_2O_3$ and $TiO_2$ can be attributed strictly to differences in metal concentration and arrangements at the catalytic surface.

The influence of Ni addition to the supported Cu catalysts was observed to be different for the $TiO_2$ supported catalysts, as compared to the $Al_2O_3$ supported catalysts. The addition of 0.5 and 1.5% Ni loadings, to form bimetallic Cu—Ni catalysts on $TiO_2$, enhanced FF conversion and MF yields, as compared to the Cu(5%)/$TiO_2$ catalyst. FF conversion increased approximately 3× on Cu(5%)-Ni(0.5 and 1.5%)/$TiO_2$ as compared to Cu(5%)/$TiO_2$ catalyst at 0.5 and 2 hours reaction time. Furthermore, MF yield was enhanced due to the addition of 0.5% and 1.5% Ni, where at 8 hours reaction time 83% and 90% MF yields were observed, respectively. When the Ni loading was further increased, to form Cu(5%)-Ni(3 and 5%)/$TiO_2$ catalysts, FF conversion at 0.5 hours reaction time increased 2× compared to the Cu(5%)-Ni(0.5 and 1.5)/$TiO_2$ catalysts. Maximum MF yields of 74.4 and 86.2% were observed at 2 hours reaction time on Cu(5%)-Ni(3%)/$TiO_2$ and Cu(5%)-Ni(5%)/$TiO_2$ catalysts, respectively. MF yields were diminished at longer reaction times for the Cu(5%)-Ni(3 and 5%)/$TiO_2$ catalysts due to the formation of MTHF. Further increasing the Ni loadings to 10% showed minimal influence on the FF HDO reactivity compared to lower Ni loadings, and diminished MF selectivity due to an increased rate of MTHF formation and the apparent degradation of FF or hydrogenation products.

Figure 30:
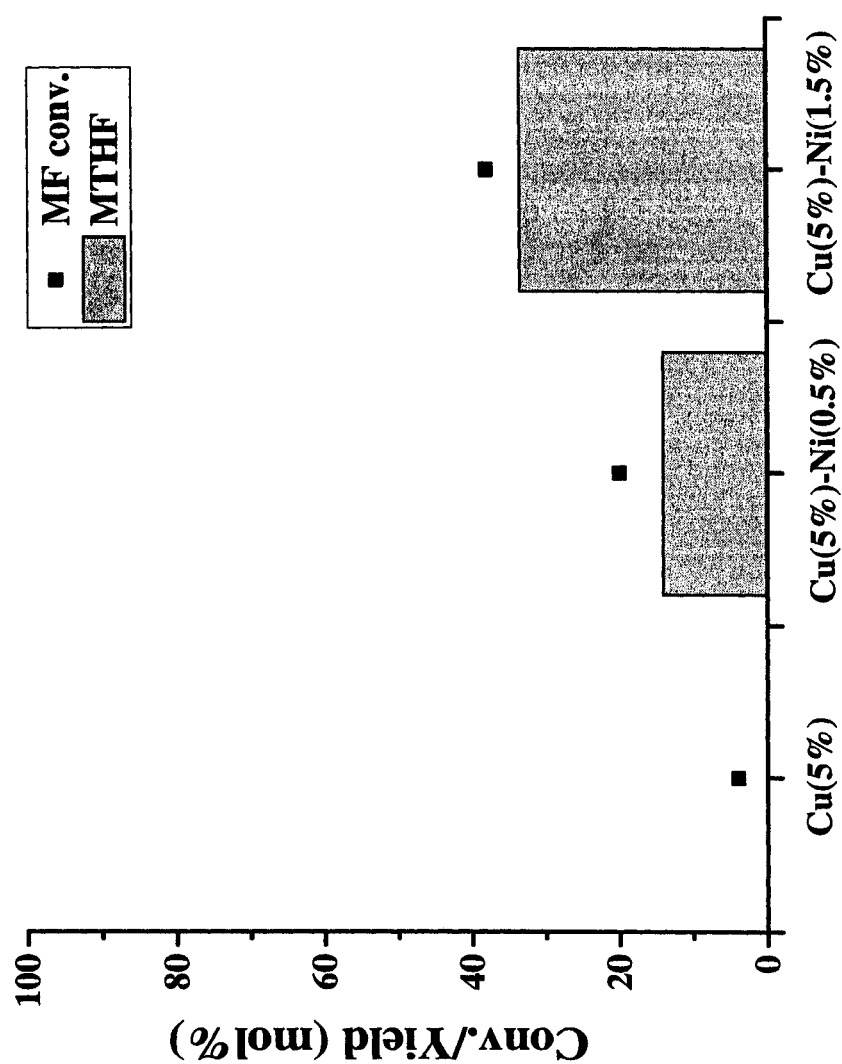
FIG. 30 is an illustration of MF conversion and MTHF yield over Cu(5%)/$TiO_2$ and Cu(5%)-Ni(0.5 & 1.5%)/$TiO_2$ catalysts. Reactions were conducted at MF loading of 1 g, catalyst loading of 0.3 g, 25 ml of 1,4-dioxane as a solvent, temperature of 200° C., 35 bar of $H_2$ (at 25° C.), and 4 hours reaction time.

Interestingly, as compared to the bimetallic Cu—Ni/$Al_2O_3$ catalysts where MTHF was formed through the hydrogenolysis of THFOL, the time-dependent reactivity measurements on bimetallic Cu—Ni/$TiO_2$ catalysts suggested that MTHF forms from ring hydrogenation of MF (Scheme 1, Path a). To verify this, pure MF hydrogenation was executed over monometallic Cu(5%)/$TiO_2$ and bimetallic Cu(5%)-Ni(0.5 & 1.5%)/$TiO_2$ catalysts using 4 hours reaction time, under similar conditions as the FF HDO experiments. As shown in FIG. 30, essentially no conversion of MF was observed over the Cu(5%)/$TiO_2$ catalyst, which is consistent with the minimal expected interaction between the furan ring of MF and the pure Cu surface. On the Cu(5%)-Ni(0.5%)/$TiO_2$ and Cu(5%)-Ni(1.5%)/$TiO_2$ catalysts, 14.1 and 33.5% yields of MTHF were formed, respectively, with minimal side product formation. This demonstrates that Ni addition to Cu/$TiO_2$ catalysts promotes selective ring hydrogenation of MF to MTHF, and together with the time dependent FF HDO reactivity of these catalysts suggests that MTHF forms on $TiO_2$ supported bimetallic Cu—Ni catalysts through ring hydrogenation of MF.

To summarize the reactivity results, it was observed for both $Al_2O_3$ and $TiO_2$ supported catalysts that the addition of only 0.5% Ni to Cu catalysts significantly promotes FF HDO reactivity, which is postulated to occur by enhanced rates of $H_2$ dissociation on exposed Ni sites. However, the addition of even a small amount of Ni (0.5%) to Cu(5%)/$Al_2O_3$ catalysts induced ring hydrogenation of FOL to form THFOL, rather than hydrogenolysis to produce MF. Alternatively, when $TiO_2$ is used as a support, even at 10% Ni loading, FOL hydrogenolysis to MF is the favored pathway over ring hydrogenation to form THFOL. As a result of this difference in behavior, the ultimate production of MTHF occurs through different reaction pathways when the Cu—Ni bimetallic catalyst is supported on $TiO_2$ or $Al_2O_3$, where on $TiO_2$ MF is the intermediate, while on $Al_2O_3$ THFOL is the intermediate.

The reactivity results suggest that MF yields on Cu(5%)-Ni(X %)/$TiO_2$ catalysts are optimized at 1.5-5% Ni loading depending on the reaction time. It is worth noting that the monometallic Cu/$Al_2O_3$ catalyst showed comparable MF yields to the optimized Cu—Ni/$TiO_2$ catalyst, although it has been shown previously that Cu/$Al_2O_3$ is unstable under FF HDO reaction conditions due to carbon deposition and Cu sintering. To compare catalytic stability of the $TiO_2$ supported catalysts, recycle experiments were performed where catalysts were recycled sequentially for 4 reactivity experiments (R1-R4) followed by regeneration through calcination and reduction and a final reactivity test (R5). R1 through R4 probe the change in catalytic reactivity due to carbon deposition and Cu sintering or leaching into solution, while R5 allows analysis of only the influence of Cu sintering or leaching as regeneration removes all carbon deposits. FF conversion was kept below 100% in all experiments.

Figure 31:
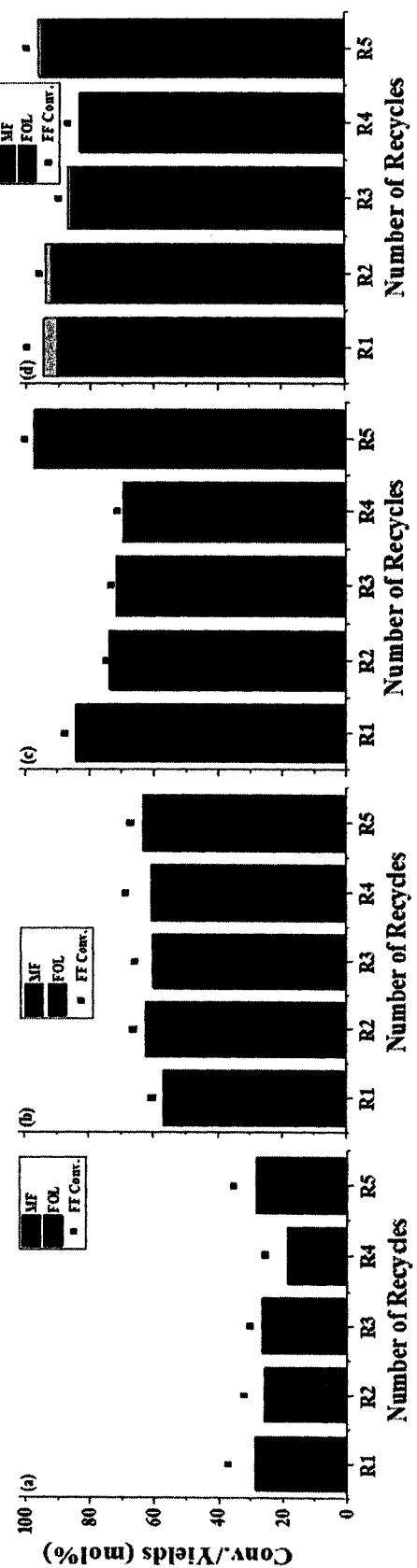
FIG. 31 is an illustration of FF conversion and product yields as a function of recycles, R, for (a) Cu(5%)/$TiO_2$, (b) Cu(5%)-Ni(0.5%)/$TiO_2$, (c) Cu(5%)-Ni(3%)/$TiO_2$, and (d) Cu(5%)-Ni(5%)/$TiO_2$ catalysts. Prior to regeneration (before R5), each catalyst was calcined at 450° C. for 5 hours and reduced at 450° C. for 3 hours under $H_2$ flow (50 ml/min). Reaction conditions were a FF loading of 1 g, catalyst loading of 0.3 g, 25 mL of 1,4-Dioxane as solvent, temperature of 200° C., $H_2$ pressure of 35 bar (at 25° C.), and 2 hour reaction time.

FIG. 31(a) shows that for the monometallic Cu(5%)/TiO$_2$ catalyst, FF conversion and MF yields decreased from 37.3% (in R1) to 25.5% (in R4) and 16.8 (R1) to 4.2% (R4), respectively, showing a significant loss of performance. Regeneration of the catalyst promoted the FF conversion and MF selectivity in R5 to a similar FF conversion and MF yield as observed in R1. FIG. 31(b) shows that the addition of 0.5% Ni to the Cu(5%)/TiO$_2$ catalyst improved the stability of the catalytic activity during R1-R4, with an essentially constant FF conversion of ~61-68%, although MF yield decreased from 37% to 11%. Following regeneration, the Cu(5%)-Ni(0.5%)/TiO$_2$ catalyst showed very similar reactivity as in R1, but with slightly decreased MF yields. Further increase in Ni loading continued to improve the stability of the catalysts. This behavior is most notable for the Cu(5%)-Ni(5%)/TiO$_2$ catalyst in FIG. 31(d), where FF conversion decreased only slightly from 99% to 88% from R1 to R4, and MF yields decreased from 87 to 60% comparing R1 to R4. Similar to the other catalyst, the behavior of the Cu(5%)-Ni(5%)/TiO$_2$ following regeneration, R5, was almost identical to R1 with 87% MF yields.

Figure 32:
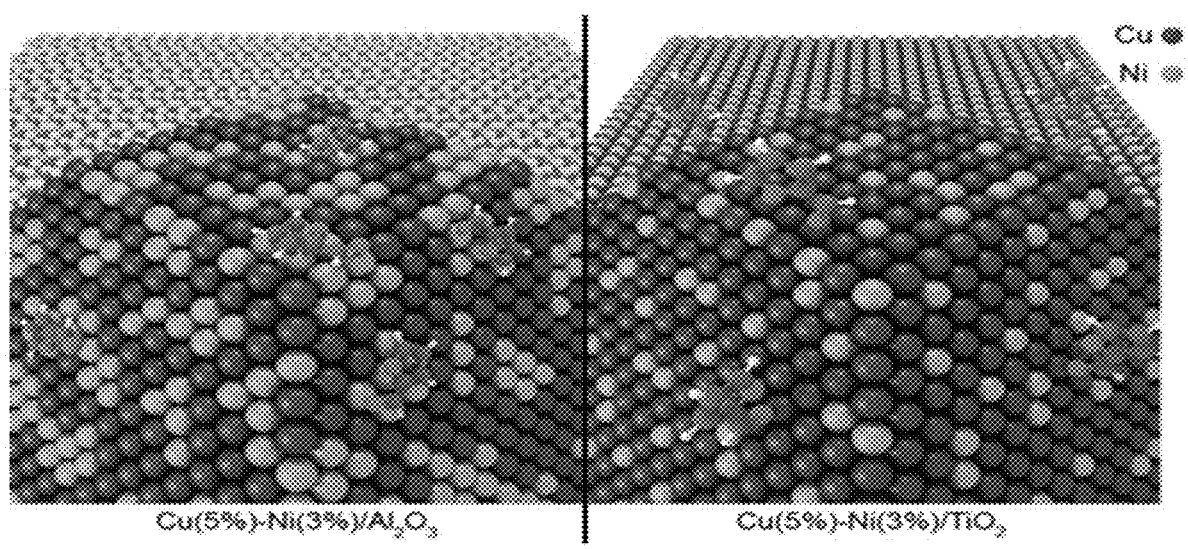
FIG. 32 is an illustration of a schematic diagram of the proposed surface composition and structure of bimetallic particles Cu—Ni on $Al_2O_3$ and $TiO_2$ supports for Cu(5%)-Ni(3%). In the case of Cu(5%)-Ni(3%)/$Al_2O_3$, significant contiguous surface Ni domains enabled more facile oxidation of the Ni and preferred FF adsorption through furan ring coordination. Alternatively, for Cu(5%)-Ni(3%)/$TiO_2$ catalysts, the catalyst surface is rich with Cu, containing mostly dispersed Ni species, which favored FF adsorption through carbonyl coordination.

The recycle and regeneration results in FIG. 32 demonstrated that the Cu(5%)/TiO$_2$ catalyst stability—in terms of activity, selectivity and regenerability—are all promoted by Ni addition, and that catalyst stability is optimized at the highest Ni loadings. It is also important to point out that in the bimetallic Cu—Ni/TiO$_2$ catalysts, throughout the explored recycle and regeneration the catalyst retained a preference to drive first FF hydrogenation to FOL followed by FOL hydrogenolysis to MF, which is in stark contrast to the Cu—Ni/Al$_2$O$_3$ catalyst. Thus, by optimizing Cu—Ni bimetallic concentration, support composition and reaction time, the activity, MF selectivity, and catalytic stability could be optimized.

In accordance with an exemplary embodiment, the composition of the support influences the structure of bimetallic Cu—Ni nanoparticles is disclosed. In previous works for Cu(5%)-Ni(5%) catalysts, a significant Cu surface segregation within the bimetallic particles was observed when TiO$_2$ was used as a support, whereas a homogeneous distribution of the metals throughout the bimetallic particles was observed when Al$_2$O$_3$ was used a support. It was argued that this result was due to strong, specific interactions between Ni and TiO$_2$ that induced Ni segregation at the TiO$_2$ interface and Cu at the catalytic surface to minimize the energy of the supported particle. In contrast, the relatively similar interaction energy between Cu or Ni and Al$_2$O$_3$ caused the formation of bimetallic particles with homogeneous Ni and Cu distributions to be energetically favorably. In accordance with an exemplary embodiment, it was noted that on both supports, enough Ni still existed at the bimetallic particle surfaces to significantly promote hydrogenation reactivity over the monometallic Cu catalysts. However, the amount of Ni at the surface controlled reactivity selectivity. The studies presented here extended insights to include understanding how support-induced segregation is influenced by Ni weight loading, and postulating how Cu and Ni are spatially organized (relative to each other) at the bimetallic nanoparticle surfaces.

Figures 26A, 26B, 26C:
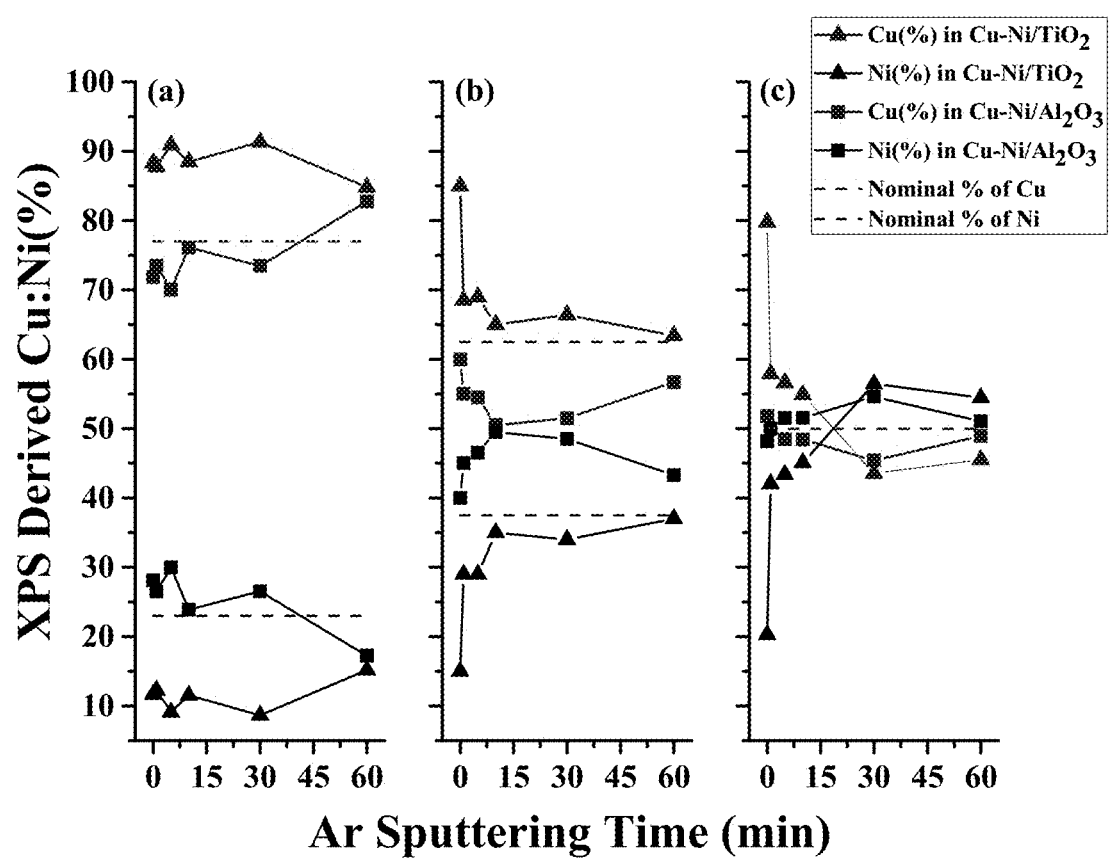
FIGS. 26(a)-26(c) are relative Cu and Ni concentration derived from deconvolution of the DP-XPS spectra as a function of Argon sputtering time where (a), (b), and (c) show the data for Cu(5%)-Ni(0.5%)/$TiO_2$ and $Al_2O_3$, Cu(5%)-Ni(3%)/$TiO_2$ and $Al_2O_3$, and Cu(5%)-Ni(5%)/$TiO_2$ and $Al_2O_3$ catalysts, respectively. The data in FIG. 2(c) is adapted from. The relative Ni concentrations are shown in black and Cu concentrations are shown in blue. Data for $Al_2O_3$ supported catalysts are depicted in squares, whereas $TiO_2$ are in triangles. The dotted lines are the expected Ni and Cu concentrations based on nominal bulk compositions.

FIGS. 26(a)-26(c) shows that regardless of the Ni loading considered (1.5, 3, and 5%), the composition of Cu at the bimetallic particles surfaces is greater than 80% when TiO$_2$ was used as a support. However, in the case of 3 and 5% Ni loadings, the relative Cu concentration dropped significantly in the first few cycles of Ar sputtering. This result suggests that for TiO$_2$ supported Cu—Ni bimetallic catalysts, a relatively thin near-surface alloy is enriched in Cu and that this behavior is consistent across various Ni loadings. Although DP-XPS analysis was not applied to the Cu(5%)-Ni(10%)/TiO$_2$ catalyst, dominant MF and FOL production at short reaction times and a lack of THFOL formation at longer times, as typically seen for monometallic Ni catalysts, strongly suggest that the near surface region is still enriched in Cu even when bulk Ni concentrations are twice that of Cu. The Cu surface segregation for bimetallic Cu—Ni catalysts on TiO$_2$ as measured by both DP-XPS and reactivity is in stark contrast with observations for the Al$_2$O$_3$ supported catalysts. It is well known that catalyst pretreatment and exposure to reaction conditions can modify the structure of bimetallic particles.[46-50] However, the consistent evidence of support induced Cu surface segregation observed here suggests that the influence of the support in controlling the compositional structure of the bimetallic particles is stronger than the influence of the pretreatment or reaction conditions on the structures. These results also suggest that the TiO$_2$ induced driving force for Cu surface segregation in bimetallic Cu—Ni particles is quite strong, even inducing this behavior when the Ni content is twice that of Cu.

In addition to the strong support-induced surface segregation of Cu in bimetallic Cu—Ni particles, combined DP-XPS and reactivity analysis also provides evidence of Cu and Ni organization at the surface. XPS analysis of the binding energy of the Cu$^0$ 2p3/2 states (see FIG. 42, Table S1) demonstrates that when Al$_2$O$_3$ is used as a support, the electronic environment of Cu is not significantly modified by increasing Ni loadings (the binding energy of Cu$^0$ 2p3/2 is essentially constant). However, when TiO$_2$ is used as a support, the Cu$^0$ 2p3/2 states shift up in energy by ~0.5 eV as the Ni loading was increased from 1.5 to 5%. This suggests that when Al$_2$O$_3$ is used as a support the interactions between Cu and Ni are relatively small within the bimetallic particles, whereas there is significant charge transfer between Cu and Ni when TiO$_2$ is used as support. Another interesting observation is that when Al$_2$O$_3$ is used as support, Ni exists in a more oxidized state (a large fraction of Ni is not metallic) on the bimetallic particle surfaces, at a given Ni weight loading, compared to TiO$_2$ as a support. Furthermore, in the DP-XPS experiments, it was observed that the existence of oxidized Ni persisted deeper into the Al$_2$O$_3$ supported bimetallic particles as compared to the TiO$_2$ supported particles. Taken together, we propose that Ni at the surface of Al$_2$O$_3$ supported bimetallic Cu—Ni particles exists in contiguous domains that have minimal interaction with Cu and can be easily oxidized, as shown in FIG. 32 (Scheme 2). Alternatively, it is suggested that Ni at the surface of Cu—Ni/TiO$_2$ catalysts is relatively scarce compared to the same Ni content in Cu—Ni/Al$_2$O$_3$ catalysts, and that the dispersion of Ni within Cu induces significant charge transfer between the metals and reduces the propensity for Ni oxidization.

Figure 41:
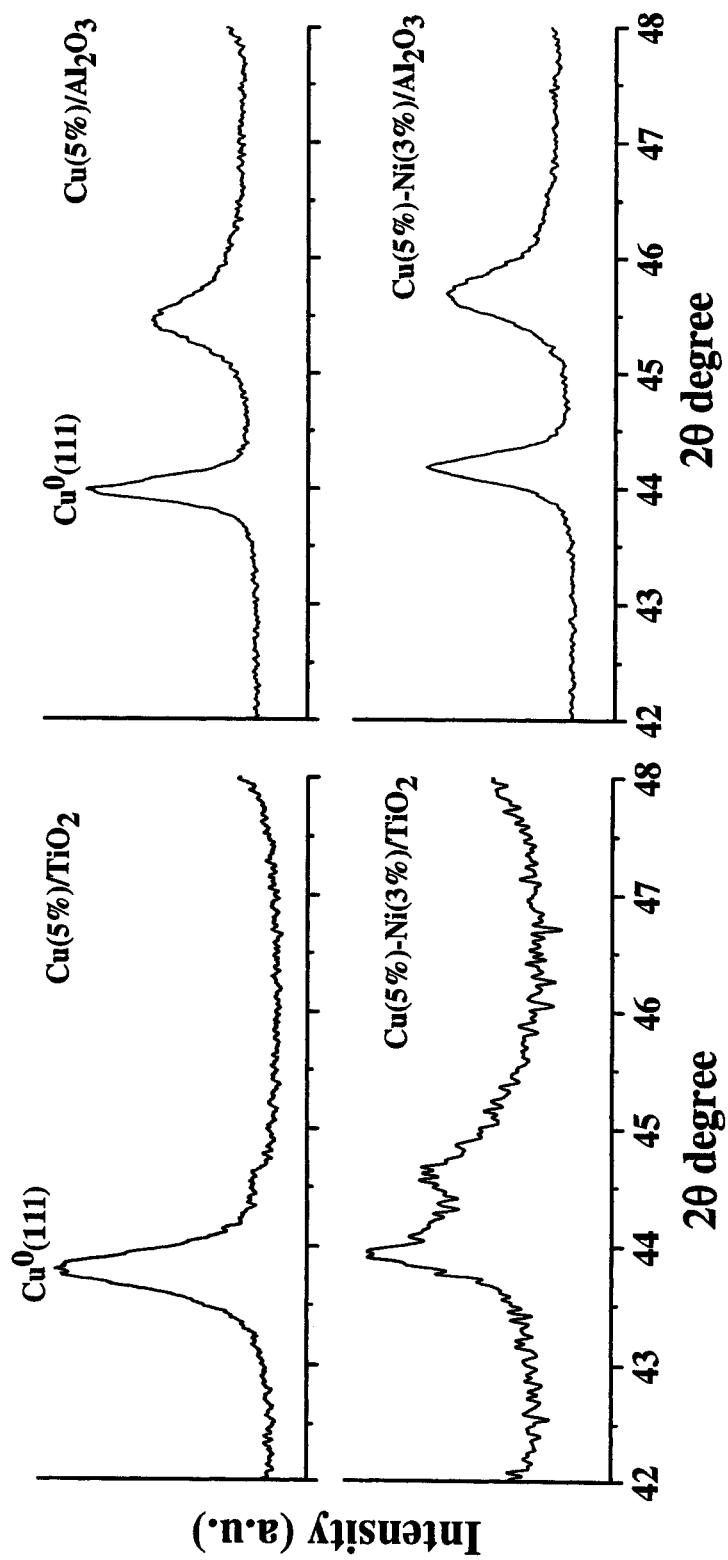
FIG. 41 illustrates XRD of Cu(5%) and Cu(5%)-Ni(3%) on $TiO_2$ and $Al_2O_3$.

The proposed structure based on DP-XPS analysis are further supported by XRD analyses of Cu(5%) and Cu(5%)-Ni(3%) catalysts on TiO$_2$ and Al$_2$O$_3$, as shown in FIG. 41, XRD spectra of Cu(5%)/TiO$_2$ and Cu(5%)/Al$_2$O$_3$ show sharp peaks at 43.7° and 43.9°, respectively, which corresponds to the metallic Cu(111) reflection. The XRD spectrum in the same region for Cu(5%)-Ni(3%)/TiO$_2$ shows two diffraction peaks at 43.9° and 44.6°. The 43.9° peak is assigned to the surface alloy phase where the low Ni concentration existing as dispersed species only slightly expands the Cu lattice, while the 44.6° reflection is assigned to the Cu—Ni alloy phase existing in the bulk of the bimetallic particles. The results agree well with the DP-XPS data that suggest 2 different phases on Cu—Ni alloys. Conversely, for Cu(5%)-Ni(3%)/$Al_2O_3$, the Cu(111) peak position shifted to a >0.2° higher 2θ value compared with Cu/$Al_2O_3$, suggesting that Cu exists in predominantly Cu domains within the bimetallic Cu—Ni particles. In both the bimetallic catalysts, it was difficult to identify peaks associated with metallic Ni due to the lower loadings compared with Cu metal. The agreement of the XRD data with the DP-XPS analysis suggests that bimetallic Cu—Ni particles form a surface segregated domain with low Ni content on $TiO_2$, while bimetallic Cu—Ni particles have significantly increased Ni content at the catalyst surface and segregated Ni and Cu domains within the particles on $Al_2O_3$.

Reactivity studies provided further evidence for the proposed support induced differences in organization of Cu and Ni at the bimetallic surfaces. For $TiO_2$ supported catalysts, there is no evidence of contiguous Ni surface domains at any considered Ni loadings. Ni is known to selectively coordinate to the furan ring in FF or FOL, rather than the carbonyl or alcohol groups. However, at even up to 10% Ni loadings, there was no evidence of preferential ring hydrogenation over alcohol hydrogenolysis, evidenced by MF selectivity rather than THFOL in FIG. 29, suggesting that Ni exists at the bimetallic Cu—Ni/$TiO_2$ surface as dispersed species that cannot coordinate to the furan ring. For the Cu(5%)-Ni (10%)/$TiO_2$ catalyst, ring hydrogenation of MF to form MTHF was observed, but because THFOL was a product, it is evident that alcohol hydrogenolysis was favored over ring hydrogenation even at the highest Ni loadings when $TiO_2$ was used as a support. While these dispersed Ni surface species on Cu—Ni/$TiO_2$ catalysts had no preferential interaction with the furan ring over the alcohol group, the increased catalytic reactivity when Ni was added strongly suggests that the dispersed Ni species could still facilitate $H_2$ dissociation. Alternatively, at all considered Ni loadings on the Cu—Ni/$Al_2O_3$ catalysts, significant evidence for preferential furan ring coordination over alcohol coordination was postulated based on the minimal MF yield and the preferential formation of THFOL. Furan ring coordination that is known to occur at Ni surfaces but not at Cu surfaces strongly suggests that Ni exists in contiguous domains on the nanoparticle surface of Cu—Ni/$Al_2O_3$ catalysts.

In accordance with an exemplary embodiment, controlling metal composition and metal-support interactions in Cu—Ni bimetallic catalysts can simultaneously promote catalytic activity, selectivity, and stability for FF conversion to MF, as compared to monometallic Cu catalysts. Detailed analysis of Cu—Ni bimetallic particles on $TiO_2$ and $Al_2O_3$ supports suggests that over a range of bimetallic compositions, $TiO_2$ promotes formation of near surface alloys rich in Cu that primarily contain dispersed Ni species. Alternatively, when Cu—Ni bimetallic particles are synthesized on $Al_2O_3$ supports, evidence suggests that Cu and Ni are evenly distributed throughout the particles other than segregation of Ni and Cu domains at the particle surface. As a result of the support induced changes in compositional structure of the bimetallic Cu—Ni particle surfaces, FF HDO results primarily in MF formation when $TiO_2$ is used as a support, while FOL and THFOL are the primary products when $Al_2O_3$ is used as a support. These results suggest that control of the surface structure and composition of bimetallic catalysts by choice of supports may be a generally useful strategy to influence reaction results for a range of catalytic processes.

Hybrid Catalytic Biorefining of Hardwood Biomass to Methylated Furans and Depolymerized Technical Lignin In accordance with an exemplary embodiment, a method is needed for all-catalytic conversion of lignocellulosic biomass to transportation fuels at high yields. In accordance with an exemplary embodiment, a method and system is disclosed for a hybrid strategy to co-produce the renewable gasoline blendstocks 2-methylfuran (MF) and 2,5-dimethylfuran (DMF) directly from hardwood poplar by combining homogeneous liquefaction with heterogeneous catalytic dehydration, with a depolymerized technical-grade lignin powder as the major solid byproduct.

In accordance with an exemplary embodiment, in a first step, poplar wood chips are liquefied under a dilute $FeCl_3$-catalyzed aqueous THF environment at a sub-pyrolytic 180° C. to yield 93.5% furfural (FF) and 66.0% 5-hydroxymethylfurfural (HMF) from xylan and glucan, respectively. In the second step, furfurals were extracted from the liquor and hydrodeoxygenated over a non-noble (Cu—Ni over $TiO_2$) catalyst to yield 87.8% of the maximum possible for MF from furfural and 85.6% of the maximum for DMF from HMF in the extract. Concurrently, poplar lignin dissolved in the liquor after the first reaction was precipitated as a crystalline solid via room temperature vacuum distillation to recover low boiling THF. Characterization of this technical lignin showed its molecular weight to be reduced by an order of magnitude from its native state as well as complete removal of its native β-aryl ether linkages without hydrogen input or further heterogeneous catalytic processing. The 60% cumulative yield of MF, DMF, and lignin products from the available carbon (xylan+glucan+lignin) in poplar rivaled cellulosic bioethanol strategies.

Economic conversion of second generation lignocellulosic feedstocks to transportation fuels has been an ongoing quest to alleviate our dependence on petroleum and other fossil resources. Using first generation feedstocks such as corn-derived sugars and cane sugar syrups to produce fuel ethanol poses food, water, and land sufficiency concerns, whereas second generation feedstocks including forestry and agricultural residues and energy crops can provide an abundant, inexpensive resource for sustainable production of renewable transportation fuels. Purely catalytic conversion of second generation feedstocks can produce fungible fuels provided high enough fuel yields can be achieved to be economic. However, most catalytic methods are unable to achieve high yields directly from raw lignocellulosic biomass due to significant catalyst poisoning, mass transport limitations, and the need for complicated separations, and typically require expensive highly purified sugar feedstocks to be compatible with exotic supported noble-metal catalysts.

Almost all advanced biofuel platforms based on biological platforms only convert the carbohydrates to fuels while the lignin (15% to 30% by weight) is used as a low value boiler fuel to generate process heat and power. Furthermore, because lignin-rich residues from biological processes are typically unrefined, their value is limited to well under $50/dry ton, the price of coal. Since nearly half the energy of some biomass varieties, such as hardwoods, is contained in their lignin, higher value uses for lignin can dramatically enhance the economic competitiveness of cellulosic biofuels. Thus, a promising route to improve the economics is development of efficient methods to extract and depolymerize lignin from biomass as a refined "technical" grade product before it is subject to degradation, condensation, and contamination as a byproduct that also interferes with carbohydrates conversion.

In accordance with an exemplary embodiment, a high yield integrated method is disclosed, which is capable of processing raw hardwood poplar chips and converting their sugars directly into fungible fuels while achieving higher total carbon utilization from the production of technical lignin. Specifically, we employed a hybrid catalytic strategy that combines homogeneous and heterogeneous methods, as outlined in FIG. 44, to co-produce 1) the high octane gasoline-range blendstocks MF and DMF at high fuel yields comparable to ethanol fermentation and 2) low molecular-weight technical lignin directly from poplar wood chips. The strategy presented here maintains high molar yields at each step, achieving an overall yield of 60% from the theoretically available xylan, glucan, and acid-insoluble lignin present in the raw material.

Results and Discussion

In the first step, poplar wood chips were solubilized in mixtures of tetrahydrofuran (THF) with water containing dilute $FeCl_3$, representing one variation of the Co-solvent Enhanced Lignocellulosic Fractionation (CELF) process. In this step, C5 and C6 sugars within the hardwood were simultaneously hydrolyzed to monomers and then co-dehydrated to the fuel precursors FF and HMF, respectively. The high performance of the first homogeneous catalytic step was owed to unique THF-water-biomass interactions during CELF reaction that accelerates cellulose and lignin solubilization, whereas the mild Lewis acidity of $FeCl_3$ promoted the kinetically favorable open-chain dehydration of sugar monomers to Furfural (FF) and 5-hydroxymethylfurfural (HMF). Furfural and HMF losses to levulinic acid and formic acid were minimized by optimizing reaction conditions.

Figure 45:
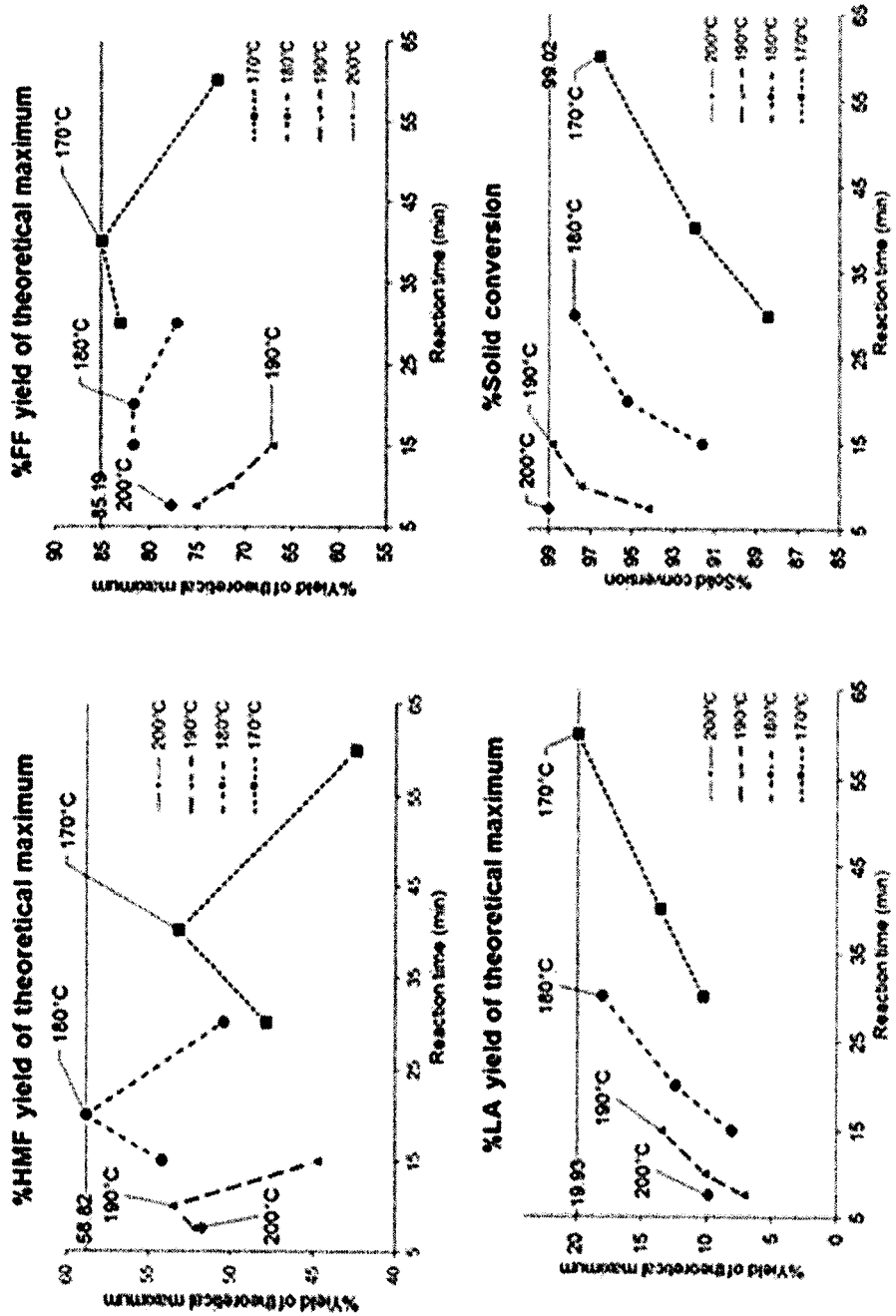
FIG. 45 illustrates optimization of reaction temperature and reaction time for production of HMF, FF, and LA from poplar wood. Reaction conditions: 3:1 THF:water 5 wt % solids loading, and 1 wt % $FeCl_3$.
Figure 46:
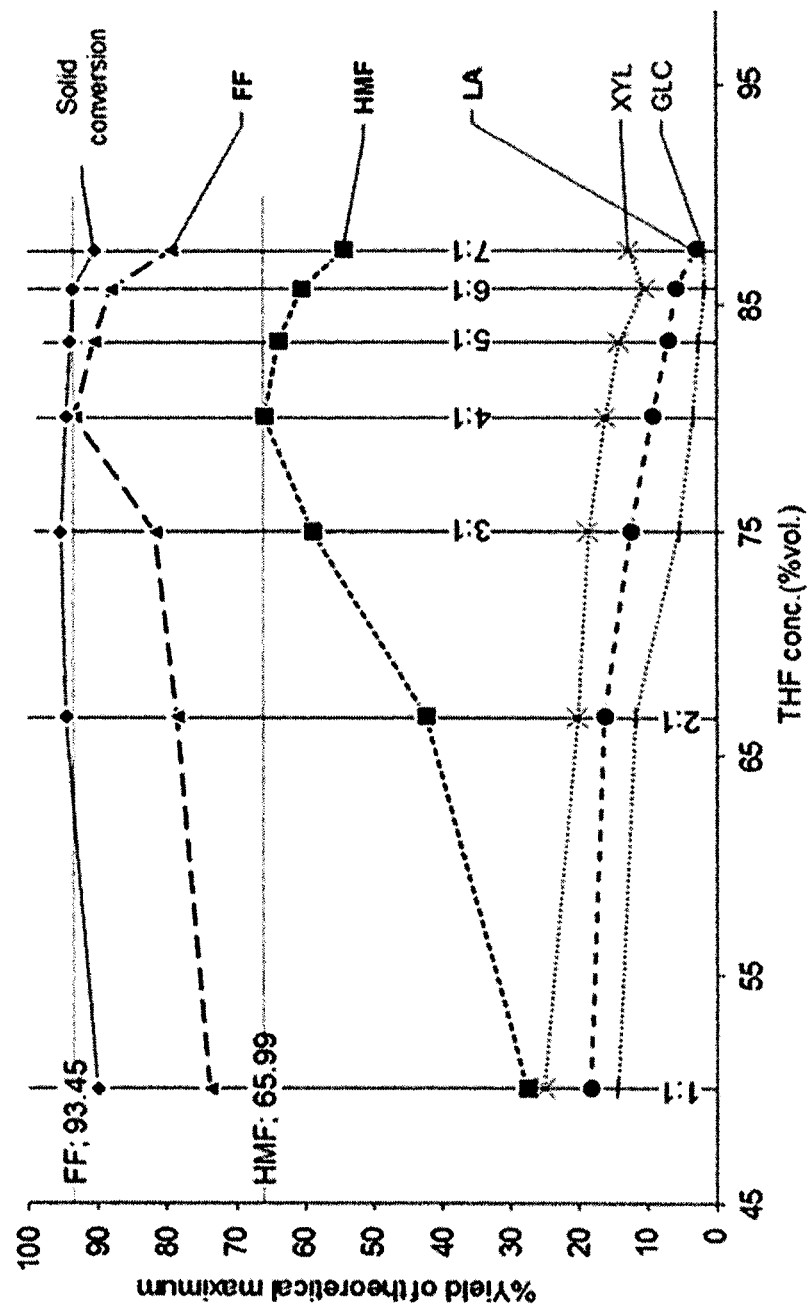
FIG. 46 illustrates dependence of yields of FF and HMF from poplar wood chips and total liquefaction/solids conversion on THF:water (1:1 to 1:7) concentrations. Reaction conditions: 180° C., 20 min, and 1 wt % $FeCl_3$ loading. Legend: FF—furfural, HMF—5-hydroxymethyl furfural, LA—levulinic acid, XYL—xylose and GLC—glucose.

Applying CELF liquefaction reactions over a range of temperatures and times, first with 3:1 THF:water mixtures, determined that 180° C. for a 20 min duration maximized FF/HMF yields and solids liquefaction, while keeping levulinic acid formation low, as shown in FIG. 45. In accordance with an exemplary embodiment, the co-solvent concentration was varied by performing reactions from 1:1 THF:water to 7:1 THF:water ratios, and determined that a 4:1 ratio achieved maximum yields of 93.5% FF and 66.0% HMF at the same time from the CELF liquor, as shown in FIG. 46. These yields are the highest reported to date from biomass in a one-pot process. Simultaneously, the CELF reaction achieved over 94% solubilization of the starting wood chips including extraction of the lignin that was precipitated as a fine solid powder upon removal and recovery of THF from the CELF liquor. This so-called "CELF lignin" yield was similar to that reported in our previous studies. The lower temperatures required for the CELF reaction compared to pyrolysis affords CELF the ability to selectivity produce furanic intermediates that are considered ideal renewable platform chemicals for the production of both fuels and chemicals, while avoiding any solid tar or char formation or gas production.

After CELF reaction at optimized conditions, $Ca(OH)_2$ was added to the CELF liquor to neutralize the acidic moieties and precipitate iron hydroxide ions, as well as a portion of lignin. These species could detrimentally influence FF and HMF extractions from CELF liquor to the organic phase and hurt catalyst stability in downstream processing. Toluene addition followed by THF separation precipitated the lignin and separated inorganic ions into the aqueous phase due to the non-polar nature of toluene. However, HMF (<60%) and FF (<80%) extraction from the aqueous to toluene phase was poor due to the polar nature of HMF. It was identified that addition of 1,4-dioxane to the toluene-aqueous phase system followed by sonication improved FF (approximately 90%) and HMF (approximately 80% to 85%) extraction yields into 1,4-dioxane-toluene phase.

Figure 44:
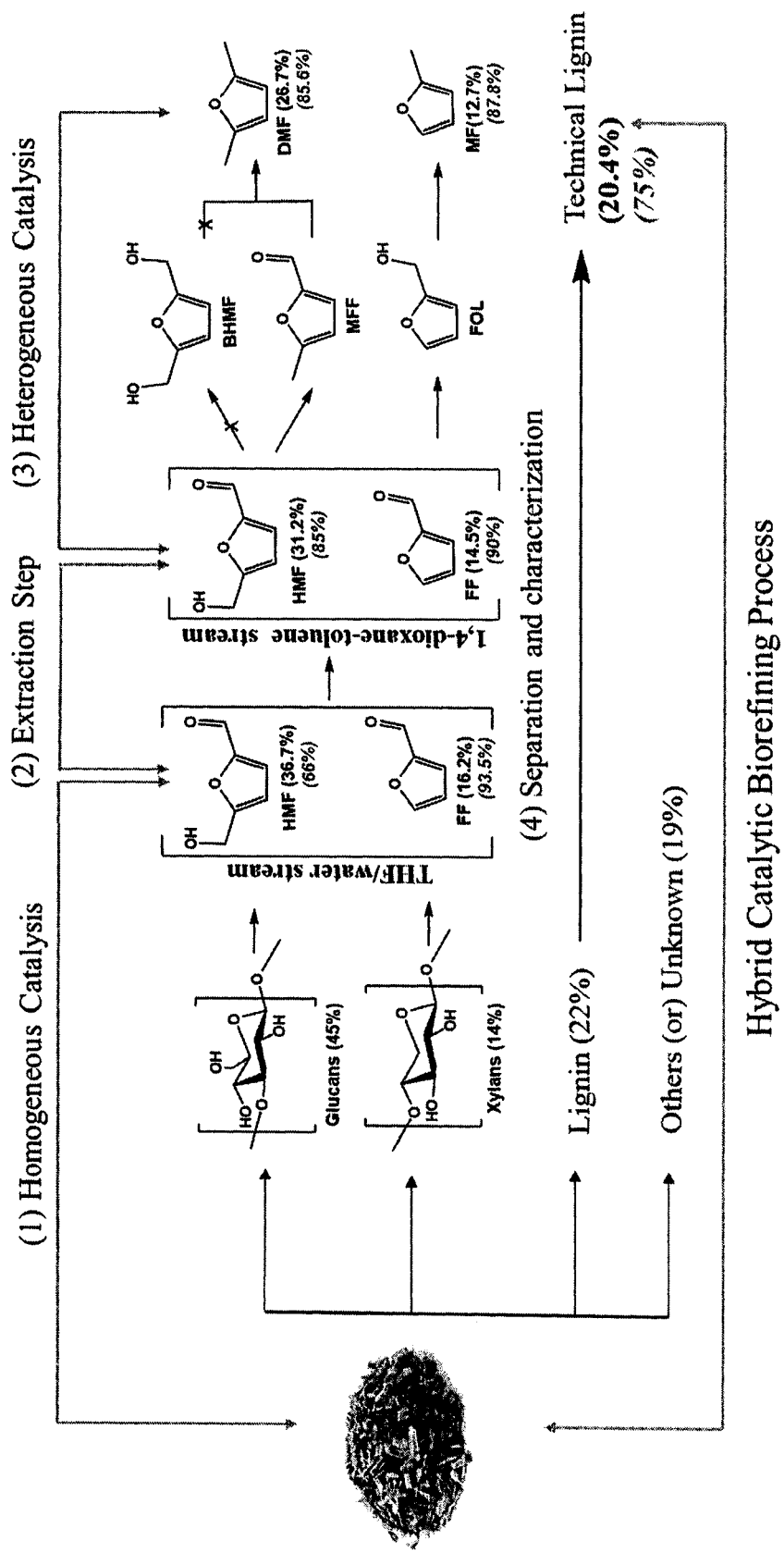
FIG. 44 illustrates a process flow diagram of integrated hybrid catalytic conversion of lignocellulosic biomass to methylated furans and technical lignins. Highlighted yields (mol %) indicate efficiency of staged yields whereas other yields (mol %) (un-highlighted) calculated based on total available carbon [glucans (45%), xylans (14%), and lignin (22%)] from biomass.

While the extraction efficiency of HMF and FF increased with addition of 1,4-dioxane, it is important to note that some $Cl^-$ can also be extracted into 1,4-dioxane due to its polar nature. Without further purification, extracted FF and HMF from CELF liquor was reacted over $Cu$—$Ni/TiO_2$ catalysts under HDO conditions. In our earlier reports, Cu(5 wt %)-Ni(5 wt %)/$TiO_2$ was shown as an active, selective, and stable catalyst for HDO of neat FF and HMF to methylated furans (i.e., MF and DMF). Characterization of the Cu—Ni particles on $TiO_2$ revealed that $TiO_2$ promoted the formation of a near surface alloy containing approximately 80% to 85% of Cu and approximately 15% to 20% of Ni. The low amount of Ni at the catalyst surface enhanced reactivity compared to monometallic Cu by promoting $H_2$ dissociation, while maintaining the inherent selectivity of Cu catalysts. Furthermore, strong Ni—$TiO_2$ interactions promoted stability of the catalysts against performance degradation by metal sintering. Usually, HDO of FF to MF occurs through FOL as an intermediate, whereas HMF to DMF occurs through either MFF or BHMF as an intermediate (FIG. 44). For the Cu—$Ni/TiO_2$ catalyst, HMF conversion to DMF was observed to occur through MFF as an intermediate instead of BHMF. The catalytic HDO of FF and HMF extracted from the CELF liquor was first considered as a function of solvent composition. Following HMF and FF extraction using pure toluene, HDO was executed at 220° C. where 26% of FF and 100% of HMF conversion were observed after 2 hours. However, the total yield of desired products was low: FOL+MF (9.8%) and MFF+DMF (91.2%). It is assumed that the lower catalytic reactivity in toluene, compared to our previous studies in neat 1,4-dioxane, was due to the non-polar nature of toluene. The HDO activity derived from 1,4-dioxane-toluene extracted FF and HMF streams was lower than for toluene alone, where diminished MF yields and HMF conversion were seen in FIG. 46(*a*).

Figure 47:
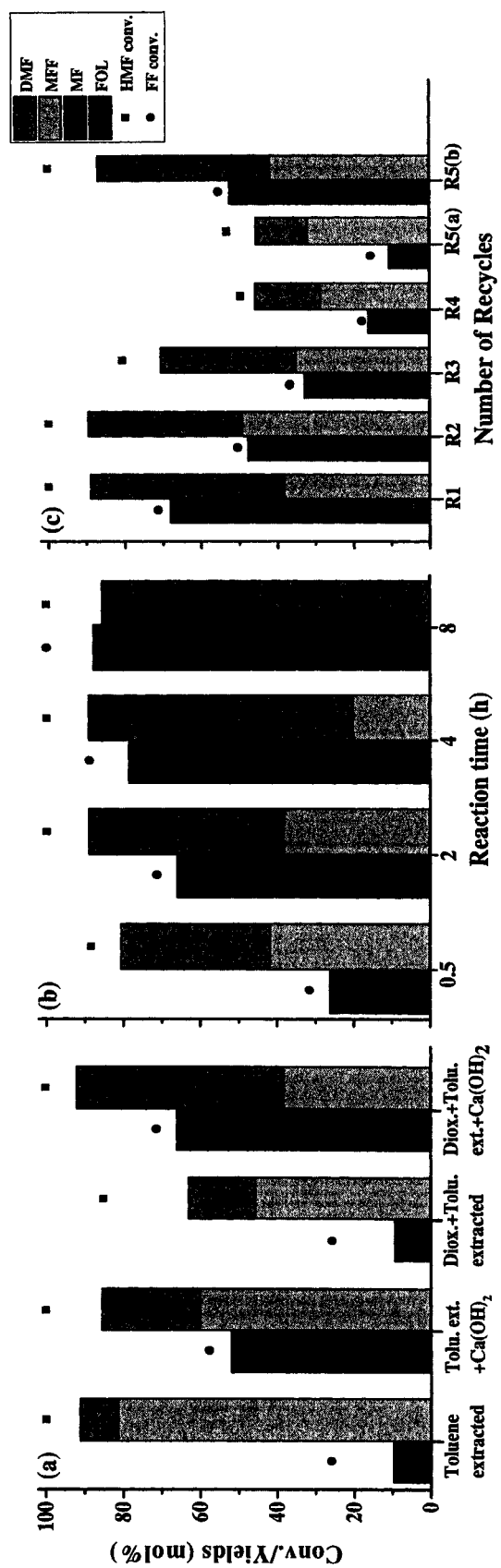
FIGS. 47(a)-47(c) illustrate HDO of toluene and 1,4-dioxane-toluene extracted FF and HMF reactions. Reactions were conducted with 25 ml of toluene (or) 1,4-dioxane-toluene extracted FF(0.5 g) and HMF(0.25 g) stream with 0.3 g of catalyst [Cu(5%)-Ni(5%)/$TiO_2$] loadings, 0.1 of $Ca(OH)_2$=0.1 g, temperature of 220° C., $H_2$-pressure of 35 bar and at 2 h. (b) As a function of time FF and HMF conversions over Cu—Ni/$TiO_2$ catalysts. Reactions were conducted at 25 ml of 1,4-dioxane-toluene extracted FF(0.5 g) and HMF(0.25 g), 0.1 g of $Ca(OH)_2$, 0.3 g of catalyst loading, and $H_2$ pressure of 35 bar (at 25° C.). (c) 1,4-dioxane-toluene extracted FF and HMF conversion and product yields as a function of recycles, R, over Cu(5%)-Ni(5%)/$TiO_2$ catalysts. Prior to regeneration (before R5), each catalyst was calcined at 450° C. for 5 hours and reduced at 450° C. for 3 hours under $H_2$ flow (50 ml/min). Reaction conditions were a 25 ml of 1,4-dioxane-toluene extracted FF(0.5 g) and HMF(0.25 g) stream, catalyst loading of 0.3 g, temperature of 220° C., $H_2$ pressure of 35 bar (at 25° C.), and 2 hour reaction time.
Figure 48:
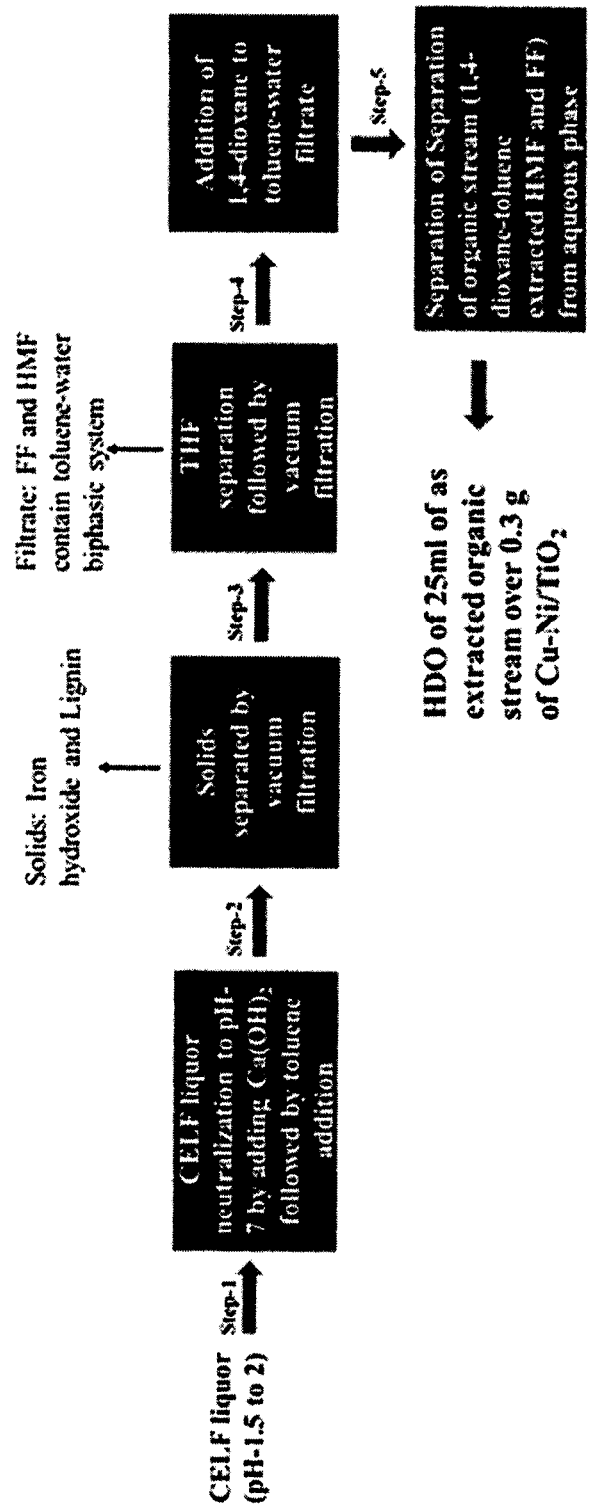
FIG. 48 illustrates FF and HMF extractions from CELF stream to 1,4-dioxane-toluene phase
Figure 49:
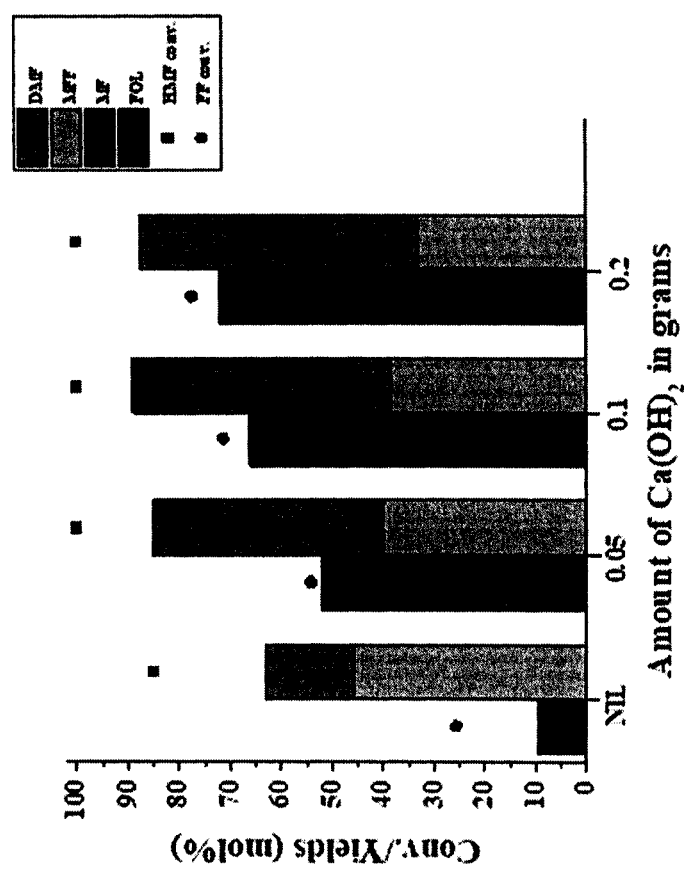
FIG. 49 illustrates Influence of $Ca(OH)_2$ addition on HDO of 1,4-dioxane-toluene extracted FF and HMF stream. All reactions were performed with 25 ml of dioxane-toluene extracted FF (0.5 g) and HMF (0.25 g), catalyst [Cu(5%)-Ni(5%)/$TiO_2$] loading of 0.3 g, 220° C. reaction temperature, $H_2$ pressure of 35 bar (at 25° C.) and 2 h reaction time.

It was hypothesized that the diminished catalytic performance observed using 1,4-dioxane-toluene extraction, as compared to toluene alone, was due to 1,4-dioxane driven extraction of trace $Cl^-$ ions from $FeCl_3$ originating from the prior pretreatment step. To neutralize acidic species and minimize $Cl^-$ extraction by the organic phase, acidic species in the 1,4-dioxane-toluene extracted FF and HMF stream were neutralized by $Ca(OH)_2$. The addition of 0.1 g of $Ca(OH)_2$ to 25 mL of extracted liquid was identified as the optimum to promote catalytic activity and selectivity in FF and HMF HDO, as seen in FIG. 49 and FIG. 47(*a*), where 70% and 100% conversion of FF and HMF and 41% and 51% MF and DMF yields were achieved, respectively. Adding the same amount of $Ca(OH)_2$ to the toluene extracted stream also promoted catalytic reactivity and selectivity, although FIG. 47(*a*) shows that the influence of $Ca(OH)_2$ was not as significant as it was on the 1,4-dioxane-toluene extracted stream.

Figure 50:
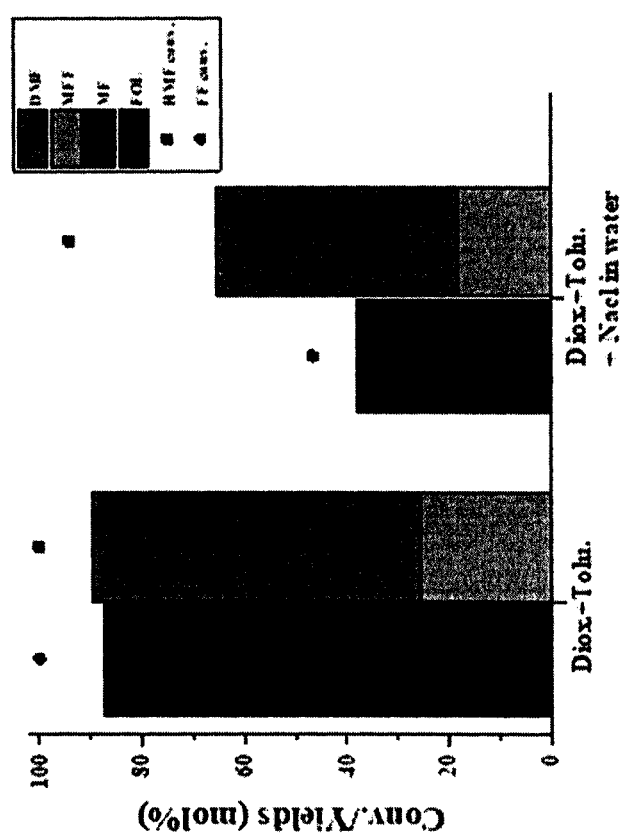
FIG. 50 illustrates chloride ions influence on neat FF and HMF HDO reactions over Cu—Ni/$TiO_2$ catalysts. Reaction were conducted at 0.5 g of FF, 0.25 g of HMF, 25 ml of 1:1 ratio of 1,4-dioxane-toluene as solvent, 0.3 g of catalyst [Cu(5%)-Ni(5%)/$TiO_2$] loading, temperature of 220° C. and $H_2$-pressure of 35 bar and 2 h reaction time. 0.250 mg of NaCl in 2 ml water was added to other reaction.

To demonstrate that $Ca(OH)_2$ likely promoted reactivity by neutralizing the influence of $Cl^-$ ions, NaCl solution was added to a neat 1,4-dioxane-toluene solution containing FF and HMF followed by executing the HDO reaction (FIG. 50). A significant drop in catalytic activity was observed in the presence of NaCl, which is consistent with the hypothesis that Ca(OH)$_2$ addition was necessary to neutralize Cl$^-$. Thus, it is seen that 1,4-dioxane and toluene are needed to maximize HMF and FF extraction efficiency from the CELF liquor, while Ca(OH)$_2$ neutralization minimized the influence of extracted Cl$^-$ on the catalytic process.

Figure 51:
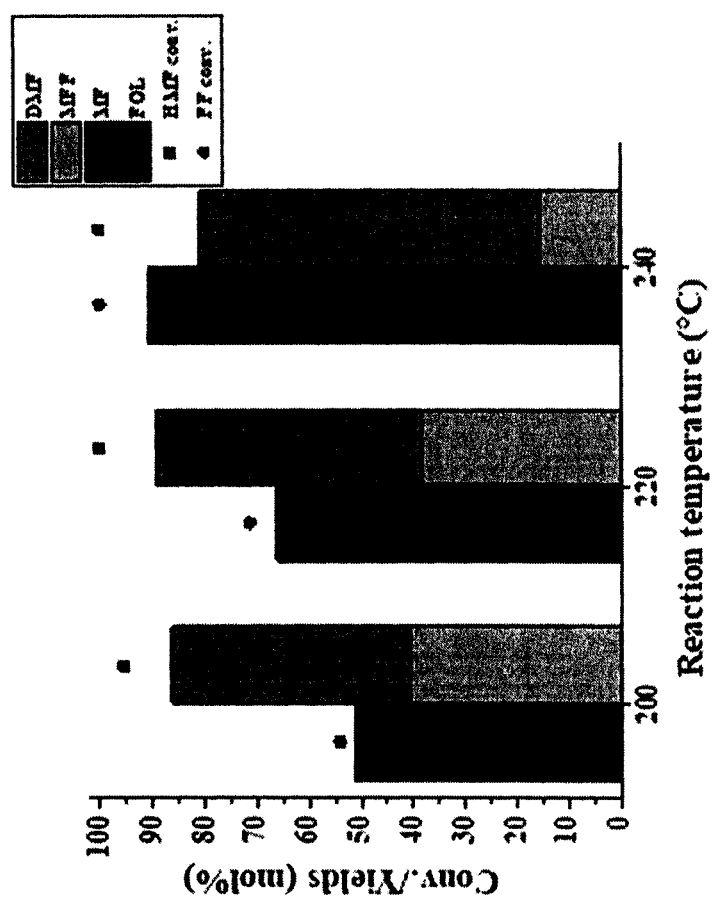
FIG. 51 illustrates temperature effect on HDO of 1,4-dioxane-toluene extracted FF and HMF. Reaction were conducted with 25 ml of dioxane-toluene extracted FF(0.5 g) and HMF(0.25) stream, 0.1 g of $Ca(OH)_2$ and catalyst [Cu(5%)-Ni(5%)/$TiO_2$] was loaded to 0.3 g and $H_2$ pressure of 35 bar (at 25° C.) and for 2 hours.

HDO of 1,4-dioxane-toluene extracted FF and HMF was conducted as a function of temperature and time to optimize MF and DMF yields, see FIG. 51 and FIG. 47(*b*). While it was observed that MF and DMF yields were maximized at 240° C., a significant loss of HMF to unwanted byproducts (not MFF or DMF) was observed, suggesting that operating at lower temperature and longer time would optimize DMF and MF yields. FIG. 47(*b*) shows the conversion and product yields from HDO of 1,4-dioxane-toluene extracted FF and HMF at 220° C. with the addition of 0.1 g of Ca(OH)$_2$ as a function of time. It was observed that at 8 hours reaction time, MF yields of 87.8% and DMF yields of 85.6% could be achieved.

To examine the stability of the catalyst, recycle experiments were conducted where reactions were executed for 2 hours, followed by separation of the catalyst and introduction of freshly separated HMF and FF. 4 sequential recycles (R1-R4) were executed without additional treatment of the catalyst or Ca(OH)$_2$ addition, followed by regeneration of the catalyst via calcination and reduction before a 5$^{th}$ recycle (R5a) and the addition of 0.1 g Ca(OH)$_2$ during a 6$^{th}$ recycle (R5b). From R1 to R4, FF conversion dropped by approximately (~) 20% in each cycle, whereas HMF conversions were similar in R1 to R2 case but dropped for the R3 and R4 cycles. To identify whether the decay in reactivity was caused by Cl$^-$ ions or more tradition mechanisms such as coking or sintering, FIG. 47(*c*) shows results for R5(a), where the catalyst was regenerated, compared with R5(b), where additional Ca(OH)$_2$ was added. It clearly observed that the loss in activity is caused by presence of Cl$^-$ ions in the 1,4-dioxane-toluene stream instead of carbon deposition or metal sintering and that this could be addressed simply by adding Ca(OH)$_2$ in each recycle.

The lignin was then precipitated from the CELF hydrolyzate prepared at the conditions optimized for producing FF and HMF (180° C., 20 min, 4:1 THF/water, 1% FeCl$_3$) by boiling the hydrolyzate to remove THF. The molecular weight, relative abundance of the lignin interunit linkage (e.g., β-O-4) and monolignol compositions (e.g., S/G ratio), and the contents of free hydroxyl groups in lignin were determined by Gel Permeation Chromatography (GPC), Heteronuclear Single Quantum Coherence (HSQC), and $^1$P Nuclear Magnetic Resonance (NMR) techniques, respectively. The functionality and molecular weight of the CELF lignin were then compared to native-like cellulolytic enzyme lignin (CEL) isolated from poplar wood, with the results presented in Table 1.

Figure 52:
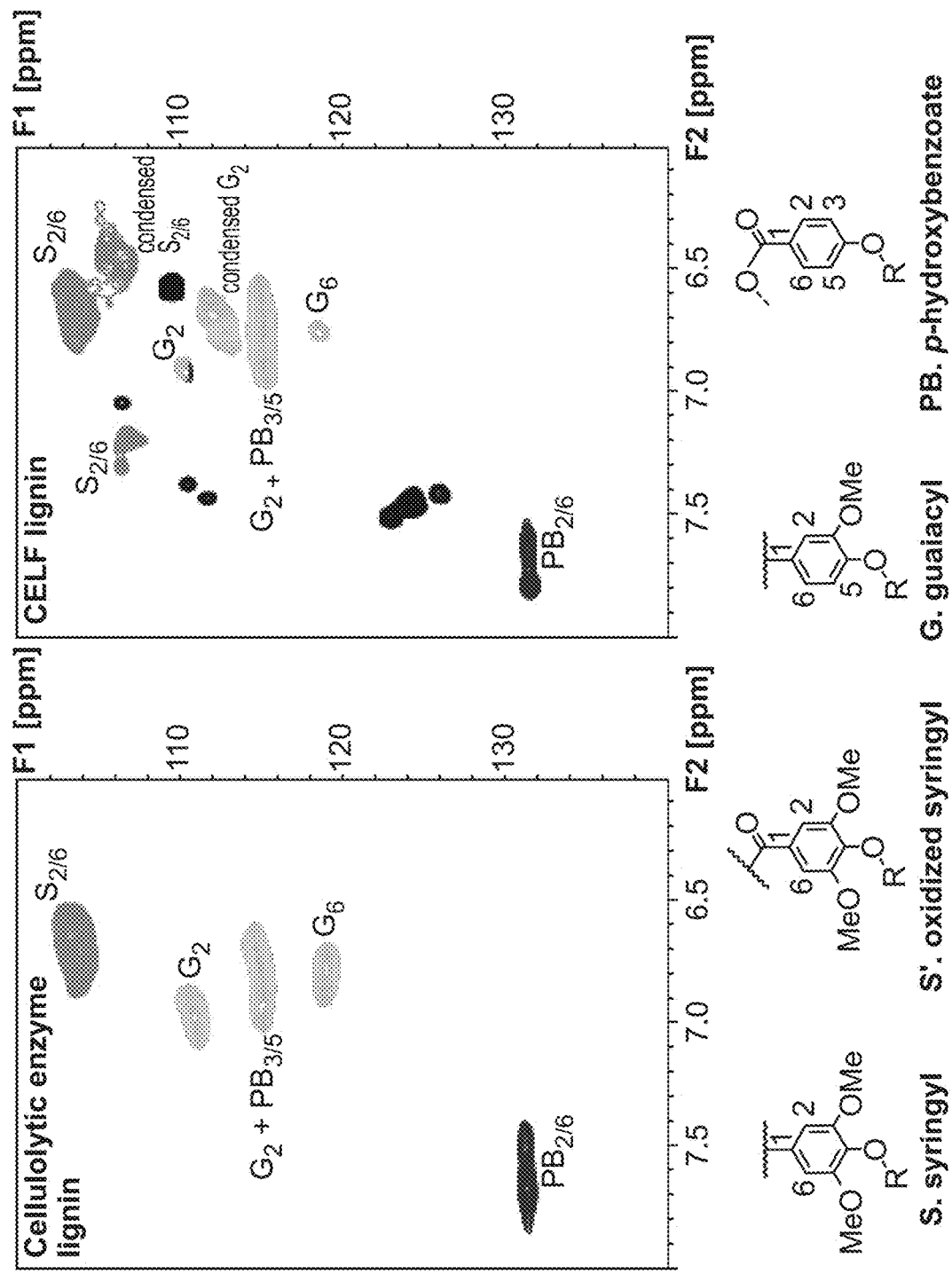
FIG. 52 illustrates aromatic regions of 2D HSQC NMR spectra of CEL and CELF lignin.
Figure 53:
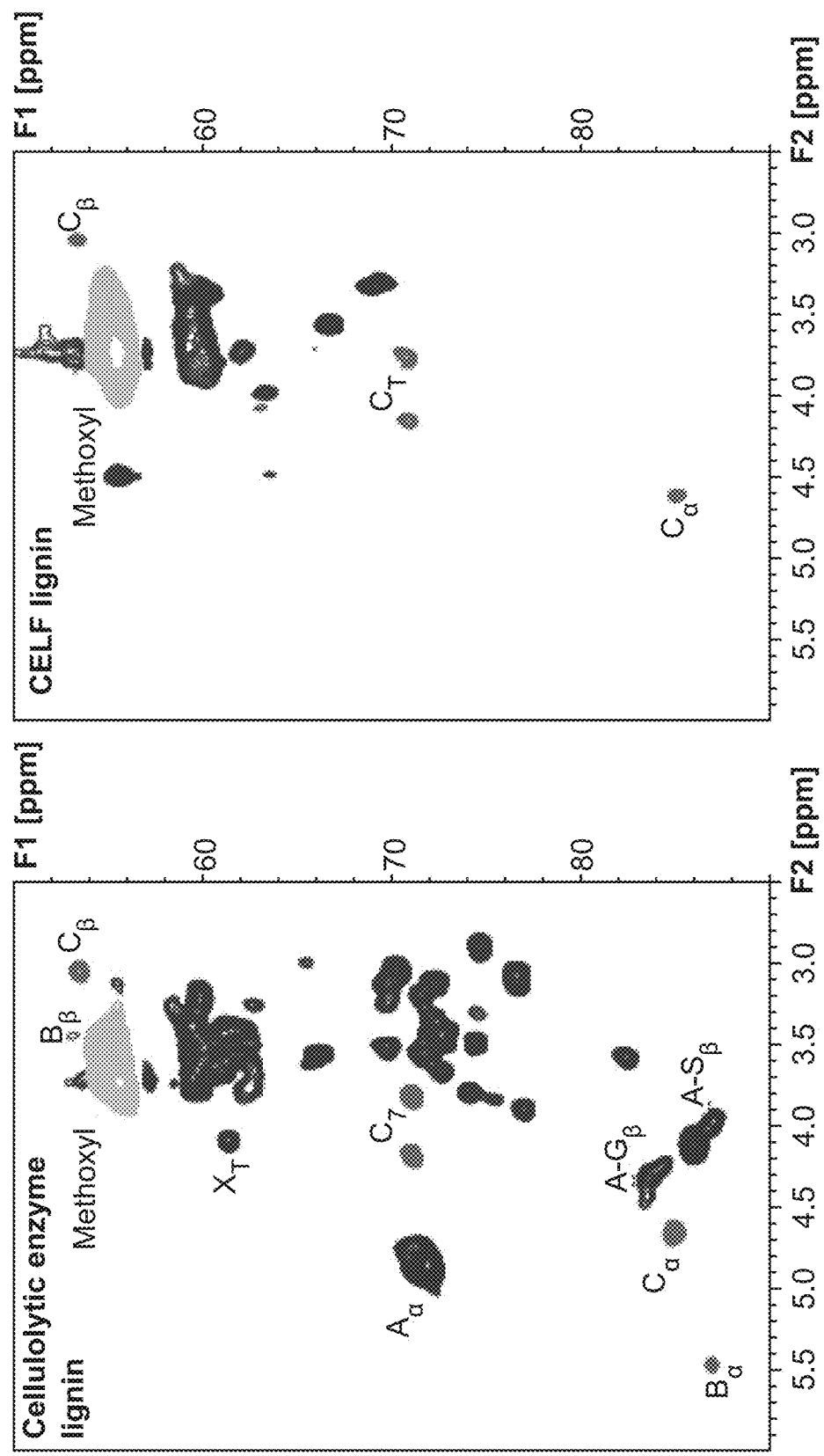
FIG. 53 illustrates aliphatic regions of 2D HSQC NMR spectra of CEL and CELF lignin.

FIGS. 52 and 53 present the aromatic and aliphatic regions of HSQC NMR spectra of CEL and CELF lignin, respectively. In the aliphatic regions, β-aryl ether (β-O-4) were the dominant interunit linkages in poplar CEL along with minor amounts of phenylcoumaran (β-5) and resinols (β-β). However, only peaks associated β-β bonds were barely detected above the noise level while the remaining peaks for β-O-4 and β-5 were not apparent in CELF lignin. This result was further reinforced by the semi-quantitative analysis of HSQC spectra shown in Table 7 that probably provides the most important insights into the current lignin characterization. The cleavage of β-O-4 linkages in lignin is usually accompanied with repolymerization reactions under acid conditions. Sannigrahi et al. reported the depolymerization by fragmentation of β-O-4 structures through a benzyl carbocation intermediate and polymerization by acid-catalyzed condensation between electron-rich carbon atoms such as aromatic $C_6/C_5$ and the benzyl carbocation as the predominant reactions in acid-catalyzed pretreatments. Meanwhile, β-5 units could be converted to stilbenes through loss of the γ-methylol group as formaldehyde. However, none of these studies ever reported the total disappearance of β-O-4 and β-5 inter-linkages in lignin after organosolv pretreatments even at much harsher pretreatment conditions such as higher temperature (e.g., 195° C.) or longer pretreatment times (e.g., 60 min). To the best of our knowledge, this is the first demonstration of complete removal of β-O-4 interlinkages in lignin by a homogeneous acid-catalyzed system at relatively mild sub-pyrolytic conditions. A very recent study by Smith et al. found that THF could preferentially solvate lignin and the THF/water co-solvent mixture could act as a "theta" solvent to prevent lignin aggregation or repolymerization and thus facilitate lignin solubilization.

GPC results indicated that CELF lignin had much lower weight-average molecular weight ($M_w$) and number-average molecular weight ($M_n$) compared to CEL, suggesting significant lignin depolymerization during CELF pretreatment. The polydispersity index (PDI) that indicates the distribution of molecular mass in lignin suggested that CELF lignin had a much higher uniformity or narrower molecular weight distribution than CEL. The P NMR technique was applied to determine the proportion of different types of hydroxyl groups in CELF lignin after appropriate phosphitylation. As shown in Table 1, the dominant aliphatic hydroxyl group signal in CEL was significantly reduced by approximately (~) 73% after CELF pretreatment; on the other hand, the contents of phenolic OH, and especially the $C_5$ substituted OH, were much higher in CELF lignin compared to CEL. The drop in aliphatic OH could be due to the above mentioned loss of γ-methylol group as formaldehyde. In addition, the oxidation of aliphatic hydroxyl groups might have occurred as evident by the dramatic increase in the carboxylic OH content. The increase in total phenolic OH supports the HSQC NMR data indicating significant cleavage of lignin interunit linkages during CELF pretreatment. The relatively low content of aliphatic OH and high content of phenolic OH are desired features for potentially using CELF lignin as good antioxidant.

TABLE 7

Molecular weight, relative abundance of lignin subunits and inter-unit linkages, and free hydroxyl groups in CEL (native) and CELF lignin.

| Lignin Characteristics | CEL (native) | CELF lignin |
|---|---|---|
| Lignin sub-units and inter-unit linkages | | |
| Syringyl (S) | 61.0 | 54.9 |
| Guaiacyl (G) | 39.0 | 45.1 |
| p-Hydroxybenzoate | 15.7 | 12.6 |
| S/G ratio | 1.56 | 1.22 |
| β-aryl ether (β-O-4) | 55.5 | 0 |
| Resinols (β-β) | 6.2 | 1.47 |
| Phenylcoumaran (β-5) | 4.9 | 0 |
| Lignin molecular weights | | |
| Weight-average molecular weight (g/mol) | 11451 | 1245 |
| Number-average molecular weight (g/mol) | 2701 | 770 |
| Polydispersity index | 4.2 | 1.62 |
| Hydroxyl groups (mmol/g lignin) | | |
| Aliphatic OH | 6.25 | 1.68 |

TABLE 7-continued

Molecular weight, relative abundance of lignin subunits and inter-unit linkages, and free hydroxyl groups in CEL (native) and CELF lignin.

| Lignin Characteristics | CEL (native) | CELF lignin |
| --- | --- | --- |
| $C_5$ substituted OH | 0.21 | 1.96 |
| Guaiacyl OH | 0.35 | 0.70 |
| p-Hydroxyphenyl OH | 0.32 | 0.23 |
| Carboxylic acid OH | 0.12 | 0.42 |

High yields of furan compounds and methylated furans from poplar wood chips are reported here for a two-step process of homogenous catalysis followed by heterogeneous catalysis, respectively. In the first homogenous CELF step, application of 4:1 ratios of THF with water containing 1 wt % $FeCl_3$ at 180° C. for 20 min achieved the highest yields of FF (93.5%) and HMF (66.0%) from poplar. The unique interactions among biomass, THF, and water enabled enhanced solubilization of cellulose and lignin in the THF-water system followed by dehydration of sugars to furan compounds. The resulting furan compounds were efficiently partitioned into a 1,4-dioxane-toluene stream for HDO over Cu—Ni/$TiO_2$ catalysts. Surface rich Cu in Cu—Ni bimetallic particles promoted selective HDO of FF and HMF to 87.8% of MF and 85.6% of DMF at 220° C. Compared to poplar CEL, CELF lignin had significantly lower molecular weight and higher phenolic OH contents. The cleavage of β-O-4 inter-linkages under acid conditions, along with the unique interactions between lignin and THF-water system are the major mechanisms of lignin breakdown during CELF pretreatment.

Materials and Methods

Poplar wood was provided by the National Renewable Energy Laboratory (NREL, Golden, Colo.) and was milled to obtain less than a 1 mm particle size using a laboratory mill (Model 4, Arthur H. Thomas Company, Philadelphia, Pa.). The composition of poplar wood was measured to be 45±0.5% glucan, 14±0.3% xylan and 22±0.2% K-lignin using NREL laboratory analytical procedure in triplicates. Other materials needed for biomass composition to total 100% were not characterized in this study as small amounts were difficult to quantify using HPLC. All the pentosans were grouped together as xylan and all hexosans as glucan. THF (>99% purity, Fischer Scientific, N.J.) was used in all the CELF pretreatment reactions. Hydrated ferric chloride catalyst was purchased from Sigma Aldrich (St. Louis, Mo., US). 1,4-dioxane and toluene (HPLC Grade, Fisher Chemicals) were used as solvents for FF and HMF extraction from CELF stream and further for HDO reactions. FF (99.9% pure, Sigma Aldrich) and HMF (99.9% pure, Sigma Aldrich) were used as starting materials for HDO reactions. $Cu(NO_3)_2 \cdot 3H_2O$ (purity 99%, CAS: 10031-43-3, Aldrich, N.J., USA), $Ni(NO_3)_2 \cdot 6H_2O$ (purity 99.99%, Aldrich, Louis, Mo. 63103, USA) and $TiO_2$ (P25, Batch No. 4161060398, NIPPON AEROSIL Co., LTD, Evonik, Degussa GmbH) materials were used as precursors for synthesizing the Cu(5%)-Ni(5%)/$TiO_2$ catalysts. Detailed catalysts synthesis procedure and characterization techniques were reported in our earlier publications.

Poplar Wood Pretreatment

All pretreatment reactions were performed in a 1 L Hastelloy Parr reactor (236HC Series, Parr instruments Co., Moline, Ill.) equipped with a double-stacked pitch blade impeller rotated at 200 rpm. The THF co-solvent mixture for each reaction was prepared by volume addition of THF to water starting from 1:1 (THF 50% v/v) to 7:1 (THF 87.5% v/v). Biomass solid loadings were 5 wt. % (40 g) based on dry weight and were calculated based on the total mass of the reaction mixture. A 1 wt. % loading of $FeCl_3 \cdot 6H_2O$ catalyst was added based on its equivalent anhydrous mass in the THF-water co-solvent. Then, the contents of the reaction were soaked overnight at 4° C. All the pretreatment reactions were heated using a 4 kW fluidized sand bath (Model SBL-2D, Techne Princeton, N.J.), and temperature was controlled to within ±1° C. measured by an in-line thermocouple (Omega, K-type). The sand bath was preheated to 380° C. to maintain heat-up time less than four minutes. At the end of each reaction, the reactor was quenched in a large water bath at room temperature. The solids were then separated from the hydrolyzate using vacuum filtration through a glass fiber filter paper (Fischer Scientific, Pittsburgh, Pa.). The final mass and density of liquid fractions were measured for mass balance and yield calculations. The liquid fractions were analyzed by HPLC.

HMF and FF Extraction from CELF Stream to Toluene-1,4-Dioxane Phase

After homogeneous CELF reaction, CELF liquor was neutralized to pH-7 by adding $Ca(OH)_2$. Toluene was added at 1:5 ratio to the neutralized CELF liquor and sonicated for 30 minutes. Solids were separated from the CELF stream by vacuum filtration and then THF was removed by distillation into rotavap. Additional 1,4-dioxane added to induce phase separation and liquids were sonicated for 10 minutes to improve extraction. In this step, more than 90% of FF and approximately 80% to 85% of HMF were extracted from CELF stream to 1,4-dioxane-toluene (1:1 ratio) organic phase. Organic phase (1,4-dioxane-toluene) was separated from aqueous phase and used for HDO reaction over Cu(5%)-Ni(5%)/$TiO_2$ catalysts. For better reactivity comparisons, FF and HMF concentration in 1,4-dioxane-toluene (or) toluene stream were concentrated to 0.5 g and 0.25 g in 25 ml respectively, in each reaction by adding additional FF and HMF. Prior to HDO reaction, Cu(5%)-Ni(5%)/$TiO_2$ catalysts were reduced at 450° C. for 3 hours. Without exposure to air, 0.3 g of reduced catalysts were transferred into a 100 mL stainless-steel Parr micro bench-top reactor (4590 Series, Parr instruments Co., Moline, Ill.) containing 1,4-dioxane-toluene(1:1) and (or) toluene extracted FF and HMF stream. The reactor was initially flushed with $H_2$ and then pressurized with $H_2$ gas. Next, the reactor temperature was raised to set values (200 to 240° C.), and reactions were conducted for 0.5-8 hours.

Catalyst Recyclability Study 1,4-dioxane-toluene organic layer containing extracted FF and HMF was reacted in a 100 mL stainless-steel Parr reactor with 0.3 g of freshly reduced catalyst at 450° C. for 3 hours. In all recycle studies, required amounts of pure FF and HMF were added to as extracted 1,4-dioxane-toluene stream to maintain the same concentrations to 0.5 g and 0.250 g in 25 ml, respectively. The reactor was flushed with $H_2$ and then pressurized with $H_2$ to 35 bar. Each reaction was conducted for 2 hours at 220° C. After completion of the reaction, the reactor was cooled by quickly lowering it into a room temperature water bath (25° C.) and depressurizing in the fume hood. Then the catalyst was separated from the liquid by filtration and dried at 105° C. for 3 hours and then reused in four recycle experiments without washing (or) regeneration. Regeneration of the used catalysts was performed via calcination at 450° C. for 5 hours followed by reduction with pure $H_2$ at 450° C. for 3 hours.

Analytical Procedures

After pretreatment, obtained liquid samples containing C6, C5 sugars, HMF, FF, Levulinic acid and formic acid were analyzed by an Agilent 1200 HPLC system with a Bio-Rad Aminex HPX-87H column and RI detector along with appropriate calibration standards and with an 5 mM sulfuric acid as an eluent flow rate of 0.6 ml min$^{-1}$. The chromatograms were integrated using Empower 2 software package.

After HDO reactions, solid catalysts were separated and the liquid portion was analyzed by gas chromatography (Agilent Technologies 7890A; column: DB-WAX Ultra Inert, 30 m long×0.320 mm internal diameter×0.5 micron) equipped with FID detector using the following program: hold at 30° C. for 1 min, increase from 30 to 100° C. at a ramp rate of 10° C. min$^{-1}$, hold at 100° C. for 2 min, increase from 100 to 250° C. at a ramp rate of 25° C./min, 0 min hold, increase from 250 to 325° C. at a ramp rate of 25° C. min$^{-1}$, and 1 min hold at 325° C. Yields of the final product were quantified by using calibration curves of standard samples in the gas chromatograph. Mass balances accounting for >95% of the carbon content were obtained in all experiments. Reactant conversion and product yield were calculated as follows:

$$FF \text{ (or) } HMF \text{ conversion } \% = \left(1 - \frac{\text{moles of unreacted substrate } (FF \text{ or } HMF)}{\text{moles of substrate before reaction}}\right) \times 100$$

$$\text{Yields} = \frac{\text{moles of the product produced}}{\text{moles of } HMF \text{ (or) } FF \text{ before reaction}} \times 100$$

To prove loss of HDO activity caused by chloride ions, two reactions were conducted with pure FF and HMF as starting substrates, with and without NaCl solution addition to 1,4-dioxane-toluene stream (FIG. S4). Significant differences were observed in conversions and product yields. Addition of NaCl solution suppressed the catalytic activity, FF conversion, and total HMF yields while complete conversion and more than 85% HDO products were observed from FF and HMF without NaCl solution. These results clearly demonstrated that chloride ions can react with active sites and form their metal chlorides, thereby reducing H$_2$ adsorption and dissociation on metal active sites that could cause loss of activity.

Materials and Methods. Lignin Characterization.
Lignin Molecular Weight Analysis The molecular weight distribution of lignin samples was measured as previously described. In brief, lignin samples (approximately 20 mg) were acetylated in 2.0 mL of acetic anhydride/pyridine mixture (v/v, 1:1) at 25° C. for 24 h. ~25 mL of ethanol was then added to the reaction to quench the reaction and left for 30 min. The solvent was then removed by a rotary evaporation under reduced pressure. Samples were then dried at 45° C. overnight in a vacuum oven followed by dissolving in THF at a concentration of ~1 mg/mL prior to the GPC analysis. The molecular weight of lignin samples was analyzed on a GPC SECurity 1200 system operated on Agilent HPLC 1200 with four Waters Styragel columns (HR1, HR2, HR4, and HR6) and an UV detector (270 nm). Polystyrene narrow standards were used to prepare the calibration curve. THF was used as the mobile phase with a flow rate 1.0 mL/min.

HSQC NMR Analysis

HSQC NMR spectra of lignin samples were acquired with a Bruker Avance 400 MHz spectrometer as previously described. A standard Bruker heteronuclear single quantum coherence pulse sequence was used with the following conditions: 210 ppm spectral width in F1 ($^{13}$C) dimension with 256 data points and 13 ppm spectral width in F2 ($^1$H) dimension with 1024 data points, a 90° pulse, a $^1J_{C-H}$ of 145 Hz, a 1.5 s pulse delay, and 32 scans. Approximately 50 mg of dry lignin samples was dissolved in deuterated DMSO. The relative lignin monomer compositions and interunit linkage abundance were estimated semi-quantitatively using volume integration of contours in HSQC spectra. For monolignol compositions of S, G, and PB measurements, the S$_{2/6}$, G$_2$, and PB$_{2/6}$ contours were used. The C$_\alpha$ signals were used for contour integration for the estimation of interunit linkages such as β-O-4, β-β, and β-5. Data processing was performed using Top Spin 2.1 software (Bruker BioSpin).

P NMR Analysis

P NMR experiments were also conducted on the Bruker Avance 400 MHz spectrometer as previously described. Lignin samples were dissolved in a solvent mixture of pyridine and deuterated chloroform. The lignin solution was then further derivatized with 2-chloro-4,4,5,5-tetramethyl-1,3,2-dioxaphospholane (TMDP). Endo-N-hydroxyl-5-norbornene-2,3-dicarhoximide (NHND) and chromium acetylacetonate were added to the solution as the internal standard and relaxation agent, respectively. The spectra were acquired at a frequency of 161.93 MHz over 32K data points with an acquisition time of 1.29 s using an inverse gated decoupling pulse sequence with a 25 s pulse delay and 128 scans. Data processing was performed suing Top Spin 2.1 software (Bruker BioSpin).

It will be apparent to those skilled in the art that various modifications and variation can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A catalyst for hydrodeoxygenating (HDO) furfural (FF) and 5-hydroxymethylfurfural (HMF) to methylated furans, the catalyst comprising:
   copper-nickel (Cu—Ni) particles supported on titanium dioxide (TiO$_2$), and wherein the copper-nickel particles form core-shell structures on the titanium dioxide (TiO$_2$) in which copper (Cu) is enriched at a surface of the catalyst; and
   a weight ratio between copper (Cu) particles and nickel (Ni) particles in the catalyst is 3:1 to 1:1.

2. The catalyst according to claim 1, wherein the Cu—Ni particles are between 2.5 wt % Cu to 20 wt % Cu and between 0.5 wt % Ni to 20 wt % Ni.

3. The catalyst according to claim 1, wherein the Cu—Ni particles are 2.5 wt % Cu-1.5 wt % Ni, 5 wt % Cu-3 wt % Ni, 5 wt % Cu-5 wt % Ni, 10 wt % Cu -5 wt % Ni, 10 wt % Cu-10 wt % Ni, 15 wt % Cu-5 wt % Ni, 15 wt % Cu-10 wt % Ni, 15 wt % Cu-15 wt % Ni, 20 wt % Cu-15 wt % Ni or 20 wt % Cu-20 wt % Ni.

4. The catalyst according to claim 1, wherein the wt % of Cu and the wt % of Ni in the catalyst is approximately equal.

5. The catalyst according to claim 1, wherein the copper-nickel particles form core-shell structures on the titanium dioxide that are segregated into two or more core-shell structures and wherein a concentration of nickel (Ni) at the surface of the catalyst is reduced, thereby allowing the Ni to promote Cu reactivity without compromising selectivity.

6. The catalyst according to claim 1, wherein the catalyst is used for co-processing a biomass containing furfural (FF) and 5-hydroxymethylfurfural (HMF) by hydrodeoxygenation to methylated furans.

7. A method of synthesizing a catalyst for hydrodeoxygenating furfural (FF) and 5-hydroxymethylfurfural (HMF) to methylated furans, the method comprising:
synthesizing monometallic copper (Cu) catalysts and monometallic nickel (Ni) catalysts;
mixing the monometallic Cu and Ni catalysts in deionized water (DI-water) to form a bimetallic Cu—Ni catalyst;
drying the mixture of the bimetallic Cu—Ni catalyst;
calcining the dried mixture of the bimetallic Cu—Ni catalyst; and
synthesizing the bimetallic Cu—Ni catalyst onto titanium dioxide ($TiO_2$) to form a Cu-Ni/$TiO_2$ catalyst, and wherein the copper-nickel particles form core-shell structures in which copper (Cu) is enriched at a surface of the catalyst, and wherein a weight ratio between copper (Cu) particles and nickel (Ni) particles in the catalyst is 3:1 to 1:1.

8. The method according to claim 7, wherein a concentration of nickel (Ni) at the surface of the catalyst is reduced, thereby allowing the Ni to promote Cu reactivity without compromising selectivity.

9. The method according to claim 7, wherein the Cu—Ni particles are between 2.5 wt % Cu to 20 wt % Cu and between 0.5 wt % Ni to 20 wt % Ni.

10. The method according to claim 7, wherein the Cu—Ni particles are 2.5 wt % Cu-1.5 wt % Ni, 5 wt % Cu-3 wt % Ni, 5 wt % Cu-5 wt % Ni, 10 wt % Cu -5 wt % Ni, 10 wt % Cu-10 wt % Ni, 15 wt % Cu-5 wt % Ni, 15 wt % Cu-10 wt % Ni, 15 wt % Cu-15 wt % Ni, 20 wt % Cu-15 wt % Ni or 20 wt % Cu-20 wt % Ni.

11. The method according to claim 7, wherein the method of synthesizing the catalyst is a wet-impregnation method.

12. The method according to claim 7, wherein the wt % of Cu and the wt % of Ni in the catalyst is approximately equal.

13. The method according to claim 7, wherein the copper-nickel particles form core-shell structures on the titanium dioxide that are segregated into two or more core-shell structures.

14. A catalyst comprising:
copper-nickel (Cu—Ni) particles supported on titanium dioxide ($TiO_2$), wherein the copper-nickel particles form core-shell structures on the titanium dioxide ($TiO_2$) in which the concentration of copper at a surface of the catalyst is greater than 80%; and having a weight ratio between copper (Cu) particles and nickel (Ni) particles in the catalyst is 3:1 to 1:1.

* * * * *